(12) United States Patent
Suzuki et al.

(10) Patent No.: US 11,420,997 B2
(45) Date of Patent: Aug. 23, 2022

(54) PEPTIDE SYNTHESIS METHOD

(71) Applicant: JITSUBO Co., Ltd., Kanagawa (JP)

(72) Inventors: Hideaki Suzuki, Kanagawa (JP); Susumu Muto, Kanagawa (JP); Shuji Fujita, Kanagawa (JP); Daisuke Kubo, Kanagawa (JP)

(73) Assignee: Jitsubo Co., Ltd.

( * ) Notice: Subject to any disclaimer, the term of this patent is extended or adjusted under 35 U.S.C. 154(b) by 0 days.

(21) Appl. No.: 17/046,682

(22) PCT Filed: Apr. 13, 2019

(86) PCT No.: PCT/JP2019/016068
§ 371 (c)(1),
(2) Date: Oct. 9, 2020

(87) PCT Pub. No.: WO2019/198833
PCT Pub. Date: Oct. 17, 2019

(65) Prior Publication Data
US 2021/0139532 A1    May 13, 2021

(30) Foreign Application Priority Data
Apr. 13, 2018 (JP) .............................. JP2018-077501

(51) Int. Cl.
| | | |
|---|---|---|
| C07K 1/02 | (2006.01) | |
| C07K 1/06 | (2006.01) | |
| C07K 1/107 | (2006.01) | |
| C07K 1/14 | (2006.01) | |
| C07K 7/06 | (2006.01) | |
| C07K 1/04 | (2006.01) | |

(52) U.S. Cl.
CPC ............... *C07K 1/02* (2013.01); *C07K 1/042* (2013.01); *C07K 1/061* (2013.01); *C07K 1/063* (2013.01); *C07K 1/1077* (2013.01); *C07K 1/145* (2013.01); *C07K 7/06* (2013.01)

(58) Field of Classification Search
CPC .......... C07K 1/02; C07K 1/042; C07K 1/063; C07K 1/1077; C07K 1/145; C07K 7/06
See application file for complete search history.

(56) References Cited

U.S. PATENT DOCUMENTS

| | | | |
|---|---|---|---|
| 5,516,891 A * | 5/1996 | Siwruk .................. | C07K 1/02 530/330 |
| 8,314,208 B2 | 11/2012 | Collins | |
| 8,859,732 B2 | 10/2014 | Takahashi | |
| 2003/0018164 A1 | 1/2003 | Eggen et al. | |
| 2004/0214989 A1 | 10/2004 | Chiba et al. | |
| 2009/0069538 A1 | 3/2009 | Murao et al. | |
| 2009/0299103 A1 | 12/2009 | Chiba et al. | |
| 2010/0029904 A1 | 2/2010 | Chiba et al. | |
| 2010/0240867 A1 | 9/2010 | Takahashi | |
| 2010/0249374 A1 | 9/2010 | Takahashi | |
| 2011/0160433 A1 | 6/2011 | Takahashi | |
| 2011/0190475 A1 | 8/2011 | Nishiuchi et al. | |
| 2012/0059149 A1 | 3/2012 | Takahashi | |
| 2014/0088291 A1 | 3/2014 | Takahashi | |
| 2014/0296483 A1 | 10/2014 | Takahashi | |
| 2018/0215782 A1 | 8/2018 | Kono et al. | |
| 2019/0023726 A1 | 1/2019 | Yano et al. | |
| 2019/0225631 A1 | 7/2019 | Yano et al. | |

FOREIGN PATENT DOCUMENTS

| | | |
|---|---|---|
| EP | 3266792 A1 | 1/2018 |
| JP | 2003-055396 A | 2/2003 |
| JP | 2003-183298 A | 7/2003 |
| JP | 2004-059509 A | 2/2004 |
| JP | 6283774 B1 | 2/2018 |
| WO | 2007/034812 A1 | 3/2001 |
| WO | 2007/122847 A1 | 11/2001 |

(Continued)

OTHER PUBLICATIONS

International Search Report dated Jun. 11, 2019 in International Application No. PCT/JP2019/016068.
Sheppeck, et al., "A convenient and scaleable procedure for removing the Fmoc group in solution," Tetrahedron Letters, May 25, 2000, pp. 5329-5333, vol. 41.
Carpino, et al. "Rapid, Continuous Solution-Phase Peptide Synthesis: Application to Peptides of Pharmaceutical Interest", Organic Process Research and Development, 2003, pp. 28-37, vol. 7, issue 1.
Extended European Search Report dated Jun. 2, 2021 in EP Application No. 19785772.5.

\* cited by examiner

*Primary Examiner* — Jeffrey E. Russel
(74) *Attorney, Agent, or Firm* — Kim IP Law Group LLC

(57) ABSTRACT

The present invention has an object of shortening the process time and reducing use of a poor solvent for solidifying a carrier (Tag)-peptide component, by removing impurities without conducting solid-liquid separation (condensation, solid-liquid separation and drying operation) of a Tag-peptide component, in an Fmoc method using a Tag for liquid phase peptide synthesis. Provided is the peptide synthesis method that includes the following steps a-d: step a: a carrier-protected amino acid, carrier-protected peptide, or a carrier-protected amino acid amide, and an N-Fmoc-protected amino acid or an N-Fmoc-protected peptide are condensed in an organic solvent or a mixed solution of organic solvents, to obtain an N-Fmoc-carrier-protected peptide, step b: a water-soluble amine is added to the reaction solution after the condensation reaction, step c: the Fmoc group is deprotected from the protected amino group in the presence of a water-soluble amine, and step d: the reaction solution is neutralized by adding an acid, and further, by adding and washing with an acidic aqueous solution, then, by liquid-liquid separation an aqueous layer is removed to obtain an organic layer.

18 Claims, No Drawings
Specification includes a Sequence Listing.

(56) References Cited

FOREIGN PATENT DOCUMENTS

| | | |
|---|---|---|
| WO | 2003/018188 A1 | 3/2003 |
| WO | 2007/099656 A1 | 9/2007 |
| WO | 2010/016551 A1 | 2/2010 |
| WO | 2010/104169 A1 | 9/2010 |
| WO | 2010/113939 A1 | 10/2010 |
| WO | 2011/078295 A1 | 6/2011 |
| WO | 2012/029794 A1 | 3/2012 |
| WO | 2012/165546 A1 | 12/2012 |
| WO | 2013/089421 A1 | 6/2013 |
| WO | 2016/140232 A1 | 9/2016 |
| WO | 2017/038650 A1 | 3/2017 |
| WO | 2017/221889 A1 | 12/2017 |

PEPTIDE SYNTHESIS METHOD

CROSS-REFERENCE TO RELATED APPLICATIONS

This application is a U.S. national phase application under 35 U.S.C. § 371 of International Application No. PCT/JP2019/016068, filed on Apr. 13, 2019, which claims priority to Japanese Patent. Application No. 2018-077501 filed Apr. 13, 2018.

TECHNICAL FIELD

The present invention relates to a method for efficiently removing an amino acid active ester remaining during a condensation reaction and dibenzofulvene (DBF) generated during a deprotection reaction of Fmoc (9-fluorenylmethyloxycarbonyl) group, in liquid phase peptide synthesis, and the like.

BACKGROUND ART

Peptide synthesis techniques include a solid phase peptide synthesis method (SPPS method) and a liquid phase peptide synthesis method (LPPS method). In the solid phase peptide synthesis method, in principle, purification cannot be performed at each step of the amino acid extension reaction. In addition, the synthesis cost is high, hence, it is suitable for small-scale production. In contrast, the liquid phase peptide synthesis method is generally used for mass production, but when the peptide chain becomes long, the peptide extension reaction becomes difficult, and there is a problem in synthesizing a long chain peptide.

Therefore, it has been proposed to perform peptide synthesis using a carrier that can reversibly repeat a dissolved condition and an insolubilized (crystallized) condition. As the carrier that can reversibly repeat a dissolved condition and an insolubilized condition, various compounds have been proposed. Examples thereof include benzyl compounds obtained by introducing a long-chain fatty acid proposed by the present inventors (Patent Documents 1 to 4: (1) JP-A 2003-183298, (2) JP-A 2004-059509, (3) WO2007/034812, (4) WO2007/122847), or a benzyl compound in which silicon is further introduced at the terminal of a long-chain fatty acid to improve the solubility in an organic solvent (Patent Document 5: WO2017/038650), or a fluorene compound into which a long-chain fatty acid is introduced (Patent Document 6: WO2010/104169), a diphenylmethane compound into which a long-chain fatty acid is introduced (Patent Document 7: WO2010/113939), a benzyl type compound (Patent Document 8: WO2011/078295), and a branched compound (Patent Document 9: WO2012/029794).

In peptide synthesis, there is a problem that amino acid residues are missing in the peptide extension reaction, which is the problem even when the carrier is used. As a solution of countermeasuring missing of amino acid residues, increasing the equivalents of an amino acid and a condensing agent is performed. However, a problem that the amino acid active ester essentially remains during the amino acid condensation reaction occurs resultantly. A problem that excess amino acid active ester remaining in the reaction solution causes a double hit when deprotection of N terminal occurs. Double hit means that one or more extra amino acid residues are inserted in the target peptide. As a result of the double hit, there arises a problem that the by-production of an impurity peptide is caused and the purity of the target peptide is lowered. Additionally, it is generally a difficult and complicated process to remove the impurity peptide generated by the double hit and to isolate and purify the target peptide. As a result, there is a problem that the yield of the target peptide is reduced.

In order to solve the problem of the amino acid active ester, there are methods in which the peptide is crystallized with a carrier after the amino acid condensation reaction and before deprotection, and impurities are removed by solid-liquid separation (for example, Patent Documents 1 to 5). However, the solid-liquid separation has a problem that the steps are complicated and time-consuming since a crystallization step is included, and further, a large amount of washing solvent is required in the washing step. Furthermore, in the crystallization operation for crystallizing the carrier, the active ester may not be completely removed by washing. In addition, in the methods described in Patent Documents 1 to 5, solid-liquid separation is conducted even after deprotection of Fmoc.

As another method for removing the amino acid active ester from the reaction system by washing before deprotection, a liquid phase peptide synthesis method using a benzyloxycarbonyl group (Cbz or Z) or a t-butyloxycarbonyl group (Boc) as a protective group has been suggested in which an amine having an anion component such as β-alanine-OBz is added as a scavenger in order to remove the active ester remaining in the reaction system (Patent Document 10: JP-A 2003-55396). However, when Cbz is used as the protective group, if Met or Cys is present in the peptide sequence, the deprotection catalyst will be deactivated and cannot be applied. Further, in this method, since it is difficult to remove dibenzofulvene (DBF) generated by a method using Fmoc as a protective group (hereinafter, may be simply referred to as Fmoc method), it is difficult to apply to the Fmoc method.

In order to remove the amino acid active ester remaining in the reaction system in the liquid phase peptide synthesis method using Boc as the protective group, a method of removing an amino acid component by liquid-liquid extraction while hydrolyzing the active ester with an alkali water (for example, 5% sodium carbonate aqueous solution) has been proposed (Patent Document 11: WO2007/099656). However, under the condition of strong alkali of pH=11 or more in this method, epimerization may possibly occur, further, inactivation of the active ester by alkali hydrolysis is difficult depending on the active ester species, remaining a possibility of double hit. Therefore, high purity synthesis becomes difficult by this method. In addition, since it is difficult to remove DBF generated in the Fmoc method by this method, it is difficult to apply it to the Fmoc method.

Further, the present inventors have proposed a method in which a primary or secondary alkylamine having 1 to 14 carbon atoms or an aromatic amine, or a hydroxylamine is added as a scavenger to the reaction system after the condensation reaction, thereby quenching the amino acid active ester (Patent Document 12: WO2016/140232).

In the peptide synthesis reaction using Fmoc, DBF is generated during the reaction of deprotection of Fmoc group. When an Fmoc removal reagent (for example, piperidine or DBU, other amines) and a scavenger are used, a conjugate composed of DBF and piperidine, or of DBF and a DBF scavenger (DBF-captured body) is generated as the DBF derivative. When DBF remains in the reaction system, side reactions occur in the subsequent peptide synthesis, so it is desired to remove them efficiently.

There has been reported a method in which, during deprotection of Fmoc, an alkylthiol or solid phase thiol is allowed to coexist and DBF is scavenged, then, the crystallized peptide component is solid-liquid-separated using an ether, thereby removing DBF or DBF derivatives as impurities (Non-patent Document 1: James E. Sheppeck II et al., Tetrahedron Letters 41 (28): 5329-5333 (2000)). However, this method is limited to the method for removing DBF generated during deprotection of Fmoc, and cannot be directly applied to continuous peptide synthesis.

In addition, a method has been reported in which a DBF-piperidine scavenged body generated by piperidine is converted into a carbonate by contacting a reaction mixture obtained after deprotection of Fmoc with carbon dioxide, before removing it (Patent Document 13: WO2010/016551). However, it requires a step such as filtration and the like and is not suitable for one-pot synthesis.

Further, it has been reported that, in the Fmoc method using a carrier (Tag) that does not solidify, the amino acid active ester is scavenged by a thiol silica or decomposed by an alkali water, then, an ω-thiolcarboxylic acid is allowed to coexist during the deprotection of Fmoc reaction and allowed to scavenge DBF to attain alkali water-solubility, thereby removing impurities by washing with an alkali water (Patent Document 14: WO2013/089241). However, in this method, the same problem as in Patent Document 11 occurs when the amino acid active ester is subjected to alkaline hydrolysis. Further, when the active ester is scavenged by a thiol, the thiol ester of the scavenged body is a kind of active ester, thus, it possibly attacks an amino group generated after deprotection of Fmoc, to form a double hit body. Furthermore, in alkaline liquid separation, an amino acid scavenged body having a lipo-soluble side chain protective group shows poor solubility and is difficult to be removed, possibly leading to generation of impurities such as a double hit body, a condensate of an ω-thiolcarboxylic acid scavenged body of an amino acid, and the like.

A method has been reported in which neutralization is performed after deprotection of Fmoc, amino acids are condensed as they are, and unnecessary substances are removed by solid-liquid separation (Patent Document 15: WO2012/165546). In this method, it is necessary to remove unnecessary substances by solid-liquid separation after the condensation reaction.

CITATION LIST

Patent Document

Patent Document 1: JP-A 2003-183298
Patent Document 2: JP-A 2004-059509
Patent Document 3: WO 2007/034812
Patent Document 4: WO 2007/122847
Patent Document 5: WO 2017/038650
Patent Document 6: WO 2010/104169
Patent Document 7: WO 2011/078295
Patent Document 8: WO 2012/029794
Patent Document 9: WO 2010/113939
Patent Document 10: JP-A 2003-55396
Patent Document 11: WO 2007/099656
Patent Document 12: WO 2016/140232
Patent Document 13: WO 2010/016551
Patent Document 14: WO 2013/089241
Patent Document 15: WO 2012/165546

Non-Patent Document

Non-Patent Document 1: James E. Sheppeck II et al., Tetrahedorn Letters 41(28):5329-5333 (2000)

SUMMARY OF THE INVENTION

Technical Problem

The present invention has an object of shortening the process time and reducing use of a poor solvent for solidifying a Tag-peptide component, by removing purities without conducting solid-liquid separation (concentration, solid-liquid separation and drying operation) of a Tag-peptide component, in an Fmoc method using a carrier (Tag) for liquid phase peptide synthesis.

Solution to Problem

The present inventors have intensively studied in view of the problem and resultantly found that it is possible to deactivate an amino acid active ester generated during the condensation reaction to prevent double hit of an amino acid at the time of deprotection of Fmoc, to capture DBF generated at the time of deprotection of Fmoc, and to remove their impurities (deactivated active ester and captured DBF) from the reaction system without using a solid-liquid separation operation, by using a specific scavenger, leading to completion of the present invention. The present invention includes the followings.

[1]. A liquid phase peptide synthesis method, comprising the following steps a to d:

step a: an amino acid protected with a carrier for liquid phase peptide synthesis (hereinafter referred as to "carrier-protected" amino acid), a carrier-protected peptide or a carrier-protected amino acid amide, and an amino acid in which an amino group is protected with a 9-fluorenylmethyloxycarbonyl (Fmoc) group (hereinafter referred as to "N-Fmoc-protected" amino acid) or an N-Fmoc-protected peptide are condensed in an organic solvent or a mixed solution of organic solvents, to obtain an N-Fmoc-carrier-protected peptide (hereinafter may be referred as to "condensation reaction step" of the present invention), step b: a water-soluble amine is added to the reaction solution after the condensation reaction (hereinafter may be referred as to "scavenge reaction step" of the present invention), step c: the Fmoc group is deprotected from the protected amino group in the presence of a water-soluble amine (hereinafter may be referred as to "deprotection of Fmoc reaction step" of the present invention), and step d: an acid is added to the reaction solution to neutralize, and further, an acidic aqueous solution is added to wash the solution, then, the solution is separated, and an aqueous layer is removed to obtain an organic layer (hereinafter may be referred as to "acidic aqueous solution washing step" of the present invention), wherein the carrier for liquid phase peptide synthesis is a compound binding to an amino acid, a peptide or an amino acid amide directly or via a linker to make them insoluble in water and having a molecular weight of 300 or more, the carrier-protected amino acid, peptide or amino acid amide is an amino acid, a peptide or an amino acid amide in which the carrier is bonded directly or via a linker to any one group selected from the group consisting of one or several amino groups, one or several carboxyl groups, one or several thiol groups and one or several hydroxyl groups carried on the amino acid, peptide or amino acid amide, and the water-soluble amines in the step b and the step c may be the same or different.

[2] The peptide synthesis method according to the above [1], wherein the carrier for liquid phase peptide synthesis is a carrier derived from a compound selected from the group consisting of a compound having the following structure (in the specification, referred as to "Ka" in some cases):

[Chemical Formula 1]

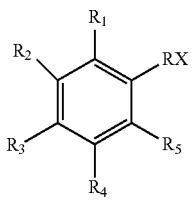

(wherein, $R_1$ and $R_5$ are hydrogen atoms, $R_2$, $R_3$ and $R_4$ are alkoxy groups having 8 to 30 carbon atoms, preferably 12 to 22 carbon atoms, RX is a group represented by the following formula and binding to a carboxyl group, an amino group or a hydroxyl group of an amino acid, a peptide or an amino acid amide or to a linker,

[Chemical Formula 2]

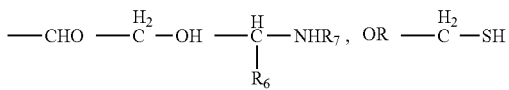

(wherein, $R_7$ represents a hydrogen atom, an a y group having 1 to 6 carbon atoms, a benzyl group or an alkoxy-substituted benzyl group, and $R_6$ represents a hydrogen atom, a phenyl group or an alkoxy-substituted phenyl group, wherein, the formula is shown in the condition before binding to a carboxyl group, an amino group or a hydroxyl group of an amino acid, a peptide or an amino acid amide or to a linker), a compound having the following structure (in the specification, referred as to "Kb" in some cases):

[Chemical Formula 3]

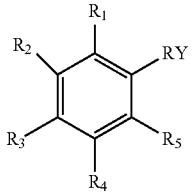

(wherein, $R_2$, $R_4$ and $R_5$ are hydrogen atoms, $R_1$ and $R_3$ are alkoxy groups having 12 to 30 carbon atoms, preferably 18 to 22 carbon atoms, RY is a group represented by the following formula and binding to a carboxyl group, an amino group or a hydroxyl group of an amino acid, a peptide or an amino acid amide or to a linker,

[Chemical Formula 4]

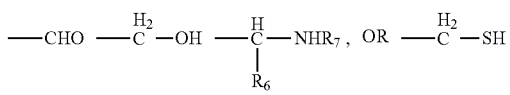

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group, wherein, the formula is shown in the condition before binding to a carboxyl group, an amino group or a hydroxyl group of an amino acid, a peptide or an amino acid amide or to a linker), and a compound having the following structure (in the specification, referred as to "Kc" in some cases):

[Chemical Formula 5]

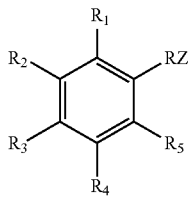

(wherein, $R_1$, $R_3$ and $R_5$ are hydrogen atoms, $R_2$ and $R_4$ are alkoxy groups having 12 to 30 carbon atoms, preferably 18 to 22 carbon atoms, RZ is a group represented by the following formula and binding to a carboxyl group, an amino group or a hydroxyl group of an amino acid, a peptide or an amino acid amide or to a linker,

[Chemical Formula 6]

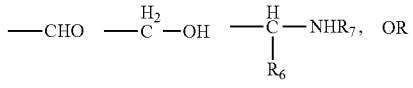

$$—\overset{H_2}{C}—SH$$

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group, wherein, the formula is shown in the condition before binding to a carboxyl group, an amino group or a hydroxyl group of an amino acid, a peptide or an amino acid amide or to a linker).

[3] The peptide synthesis method according to the above [1], wherein the carrier for liquid phase peptide synthesis is a carried derived from a compound having the following structure (in the specification, referred as to "KS" in some cases):

[Chemical Formula 7]

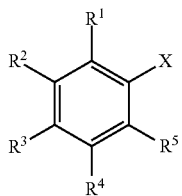

(wherein, X is a group representing —CH$_2$ORa (wherein, Ra represents a hydrogen atom, a halogenocarbonyl group or an active ester type protective group), —CH$_2$NHRb (wherein, Rb represents a hydrogen atom, a linear or branched alkyl group having 1 to 6 carbon atoms or an aralkyl group), a halogenomethyl group, a methyl azide group, a formyl group or an oxime, and binding to a carboxyl group, an amino group or a hydroxyl group of an amino acid, a peptide or an amino acid amide or to a linker; at least one of R$^1$, R$^2$, R$^3$, R$^4$ and R$^5$ represents a group represented by the following formula:

—O—R$^6$—Xa-A, and the residual groups represent a hydrogen atom, a halogen atom, an alkyl group having 1 to 4 carbon atoms or an alkoxy group having 1 to 4 carbon atoms; R$^6$ represents a linear or branched alkylene group having 1 to 16 carbon atoms, Xa represents O or CONRc (wherein, Rc represents a hydrogen atom or an alkyl group having 1 to 4 carbon atoms), A represents any of the following formula (1) to the formula (11),

[Chemical Formula 8]

(1)

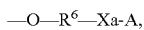

(2)

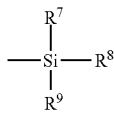

(3)

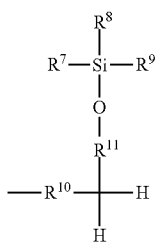

(4)

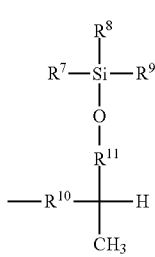

(5)

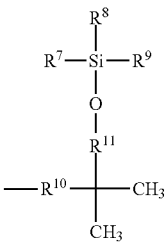

(6)

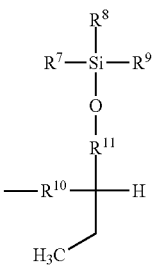

(7)

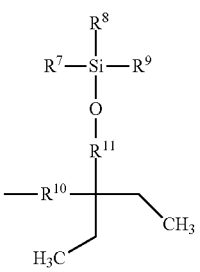

(8)

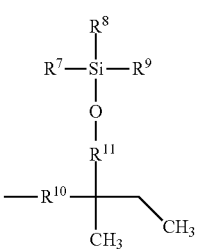

(9)

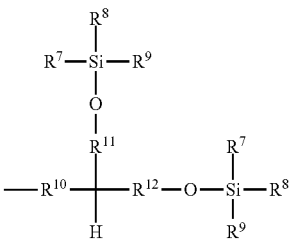

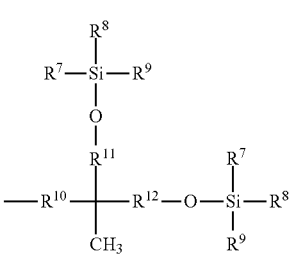

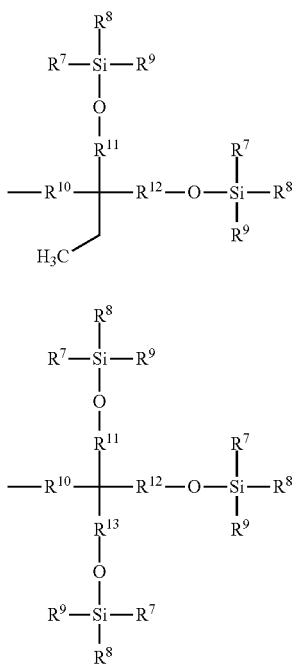

(wherein, $R^7$, $R^8$ and $R^9$ may be the same or different and represent a linear or branched alkyl group having 1 to 6 carbon atoms, or an aryl group optionally having a substituent, $R^{10}$ represents a single bond or a linear or branched alkylene group having 1 to 3 carbon atoms, and $R^{11}$, $R^{12}$ and $R^{13}$ may be the same or different and represent a linear or branched alkylene group having 1 to 3 carbon atoms, wherein, the formula is shown in the condition before binding to a carboxyl group, an amino group or a hydroxyl group of an amino acid, a peptide or an amino acid amide or to a linker).

[4] The peptide synthesis method according to the above [1], wherein the carrier for liquid phase peptide synthesis is a carrier derived from a fluorene compound represented by the general formula (V):

[Chemical Formula 9]

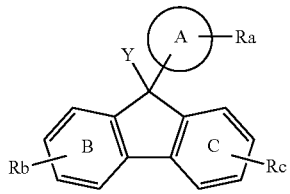

(V)

[wherein, Ring A represents an aromatic ring; Y is a hydroxyl group, a bromo group or a chloro group; Ra, Rb and Rc each independently represent an organic group having an aliphatic hydrocarbon group, a hydrogen atom or an electron withdrawing group, and at least one of Ra, Rb and Rc is an organic group having an aliphatic hydrocarbon group; Rings A, B and C each independently may have an electron withdrawing group], or the general formula (V'):

[Chemical Formula 10]

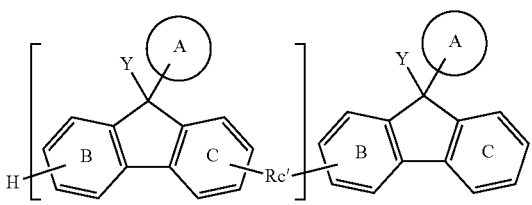

(V')

[wherein, Ring A represents an aromatic ring; Y is a hydroxyl group, a bromo group or a chloro group; n represents an integer of 1 to 19; Rc' is a divalent organic group having an aliphatic hydrocarbon group; Rings A, B and C each independently may have at least one selected from an organic group having an aliphatic hydrocarbon group and an electron withdrawing group; when a plurality of Rings A are present, the respective Rings A may be the same or different; when a plurality of groups Y are present, the respective groups Y may be the same or different; when a plurality of groups Rc' are present, the respective groups Rc' may be the same or different, wherein, the divalent organic group having an aliphatic hydrocarbon group is a group represented by the formula (a):

[Chemical Formula 11]

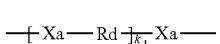
(a)

(wherein, Xa is not present or represents —O—, —S—, —NHCO— or —CONH—; Rd represents an aliphatic hydrocarbon group having 5 or more carbon atoms; $k_1$ represents an integer of 1 to 10; when a plurality of groups Rd are present, the respective groups Rd may be the same or different; and when a plurality of groups Xa are present, the respective groups Xa may be the same or different.), the organic group having an aliphatic hydrocarbon group is at least one group selected from the group consisting of a group represented by the formula (b):

[Chemical Formula 12]

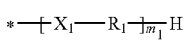
(b)

(wherein, * represents the binding position; $X_1$ is —O—; $R_1$ is an aliphatic hydrocarbon group having 5 to 60 carbon atoms; and $m_1$ is 1.), a group represented by the formula (c):

[Chemical Formula 13]

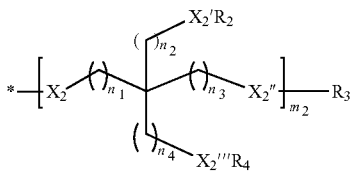

(wherein, represents the binding position; $X_2$, $X_2'$, $X_2''$ and $X_2'''$ are —O—; $R_2$ and $R_4$ are each independently aliphatic hydrocarbon groups having 5 to 60 carbon atoms; $R_3$ is an organic group having an aliphatic hydrocarbon group having 5 to 60 carbon atoms; $n_1$, $n_2$, $n_3$ and $n_4$ are 1; and $m_2$ is 1), and a group represented by the formula (d):

[Chemical Formula 14]

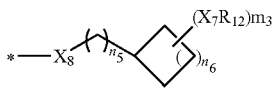

(wherein, * represents the binding position; Xa represents —O—; $m_3$ is 2 or 3; $n_5$ is 1; $n_6$ is 3; $X_7$ is —O—; $m_3$ groups $R_{12}$ are each independently alkyl groups having 4 to 30 carbon atoms), existing at the 2-position and/or the 7-position of the fluorene compound](wherein, each of the formula is shown in the condition before binding to a carboxyl group, an amino group or a hydroxyl group of an amino acid, a peptide or an amino acid amide or to a linker.).

[5] The peptide synthesis method according to the above [1], wherein the carrier for liquid phase peptide synthesis is a carrier derived from a benzyl compound represented by the general formula (W):

[Chemical Formula 15]

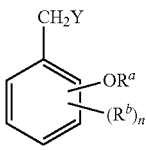

[wherein, Y represents a hydroxyl group or an —NHR group (R represents a hydrogen atom, an alkyl group or an aralkyl group); $R^a$ represents an organic group having an aliphatic hydrocarbon group selected from the group consisting of a group represented by the formula (a):

[Chemical Formula 16]

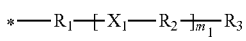

[wherein, * represents the binding position; $m_1$ represents an integer of 1 to 10; $m_1$ groups $X_1$ each independently represent a single bond or represent —O—, —S—, —COO—, —OCONH—, —NHCO— or —CONH—; $R_1$ and $m_1$ groups $R_2$ each independently represent a divalent aliphatic hydrocarbon group having 5 or more carbon atoms; and $R_3$ is a hydrogen atom or a group represented by the formula (W'):

[Chemical Formula 17]

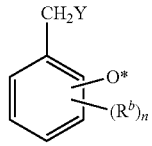

(wherein, * represents the binding position; n groups $R^b$ each independently represent an alkoxy group having 1 to 6 carbon atoms, a halogen atom, or an alkyl group having 1 to 6 carbon atoms optionally substituted with one or more halogen atoms; and n represents an integer of 0 to 4)];

a group represented by the formula (b):

[Chemical Formula 18]

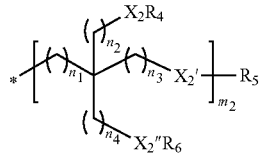

(wherein, represents the binding position; $m_2$ represents 1 or 2; $n_1$, $n_2$, $n_3$ and $n_4$ each independently represent an integer of 0 to 2; $m_2$ groups $X_2$, $m_2$ groups $X_2'$ and $m_2$ groups $X_2''$ each independently represent a single bond or represent —O—, —S—, —COO—, —OCONH—, —NHCO— or —CONH—; $m_2$ groups $R_4$ and $m_2$ groups $R_6$ each independently represent an aliphatic hydrocarbon group having 5 or more carbon atoms; $R_5$ represents an aliphatic hydrocarbon group having 5 or more carbon atoms.);

a group represented by the formula (c):

[Chemical Formula 19]

(wherein, * represents the binding position; $m_3$ represents an integer of 0 to 15; $n_5$ represents an integer of 0 to 11; $n_6$ represents an integer of 0 to 5; $m_3$ groups $X_3$ each independently represent a single bond or represent —O—, —S—, —COO—, —OCONH—, —NHCO— or —CONH—; and $m_3$ groups $R_7$ each independently represent a hydrogen atom, a methyl group or an aliphatic hydrocarbon group having 5 or more carbon atoms); and a group represented by the formula (d):

[Chemical Formula 20]

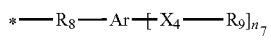

(wherein, * represents the binding position; $n_7$ groups $X_4$ each independently represent a single bond or represent —O—, —S—, —COO—, —OCONH—, —NHCO— or —CONH—; $R_8$ represents a divalent aliphatic hydrocarbon group; $n_7$ groups $R_9$ each independently represent a monovalent aliphatic hydrocarbon group; $n_7$ represents an integer of 1 to 5; and Ar represents an arylene group.), the total number of carbon atoms in the organic group is 30 or more; n groups $R^b$ each independently represent an alkoxy group having 1 to 6 carbon atoms, a halogen atom, or an alkyl group having 1 to 6 carbon atoms optionally substituted with one or more halogen atoms; and n represents an integer of 0 to 4.]

(wherein, the formula is shown in the condition before binding to a carboxyl group, an amino group or a hydroxyl group of an amino acid, a peptide or an amino acid amide or to a linker).

[6] The peptide synthesis method according to the above [1], wherein the carrier for liquid phase peptide synthesis is a carrier derived from a diphenylmethyl compound represented by the general formula (X):

[Chemical Formula 21]

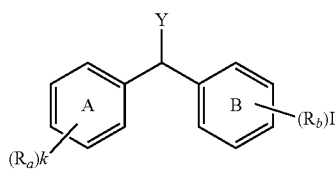

[wherein, Y represents a hydroxyl group or an —NHR group (R represents a hydrogen atom, an alkyl group or an aralkyl group); k and l each independently represent an integer of 0 to 5, providing k+l is not 0; k groups $R_a$ and l groups $R_b$ each independently represent an organic group having an aliphatic hydrocarbon group having 5 or more carbon atoms selected from the group consisting of a group represented by the formula (a):

[Chemical Formula 22]

(wherein, * represents the binding position; $m_1$ represents an integer of 1 to 10; $m_1$ groups $X_1$ each independently are not present or represent —O—, —S—, —COO—, —OCONH— or —CONH—; $m_1$ groups $R_1$ each independently represent a divalent aliphatic hydrocarbon group having 5 or more carbon atoms.), a group represented by the formula (b):

[Chemical Formula 23]

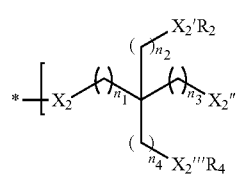

(wherein, * represents the binding position; $m_2$ represents an integer of 1 to 2; $m_2$ groups $n_1$, $n_2$, $n_3$ and $n_4$ each independently represent an integer of 0 to 2; $m_2$ groups $X_2$, $m_2$ groups $X_2'$, $m_2$ groups $X_2'''$ and $m_2$ groups $X_2''$ each independently are not present or represent —O—, —S—, —COO—, —OCONH— or —CONH—; $m_2$ groups $R_2$ and $R_4$ each independently represent a hydrogen atom, a methyl group or an aliphatic hydrocarbon group having 5 or more carbon atoms; and $R_3$ represents an aliphatic hydrocarbon group having 5 or more carbon atoms.), and a group represented by the formula (e):

[Chemical Formula 24]

(wherein, * represents the binding position; $m_3$ represents an integer of 0 to 15; $n_5$ represents an integer of 0 to 11; $n_6$ represents an integer of 0 to 5; $X_2$ is not present or represents —O—, —S—, —NHCO— or —CONH—; $m_3$ groups $X_7$ each independently are not present or represent —O—, —S—, —COO—, —OCONH—, —NHCO— or —CONH—; $m_3$ groups $R_{12}$ each independently represent a hydrogen atom, a methyl group or an aliphatic hydrocarbon group having 5 or more carbon atoms), wherein the total number of carbon atoms of all aliphatic hydrocarbon groups in the organic group having (k+1) aliphatic hydrocarbon groups is 16 or more; Ring A optionally further has a substituent in addition to $R_a$; Ring B optionally further has a substituent in addition to $R_b$.]

or a branched chain-containing aromatic compound represented by the general formula (Y):

[Chemical Formula 25]

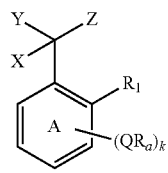

[wherein, k groups Q each independently represent a single bond or represent —O—, —S—, —C(=O)O—, —C(=O)NH— or —NH—; k groups $R_a$ each independently represent an organic group having at least one aliphatic hydrocarbon group having one or more branched chains, having a total number of branched chains of 3 or more and having a total number of carbon atoms of 14 or more and 300 or less; k represents an integer of 1 to 4; $R_1$ is a hydrogen atom, alternatively, when Z is a group represented by the following formula (a), may represent a single bond together with $R_2$ and may form a fluorene ring together with Ring B; Ring A optionally has at least one substituent selected from the group consisting of a halogen atom, a C1-6 alkoxy group optionally substituted with one or more halogen atoms and a C1-6 alkoxy group optionally substituted with one or more halogen atoms, in addition to $R_1$, k groups $QR_a$ and $C(X)(Y)Z$; X represents a hydrogen atom or a phenyl group; Y represents a hydroxyl group or an —NHR group (R represents a hydrogen atom, an alkyl group or an aralkyl group); and Z represents a hydrogen atom or a group represented by the formula (a):

[Chemical Formula 26]

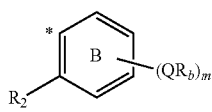

(a)

(wherein, * represents the binding position; m represents an integer of 0 to 4; m groups Q represent the same meaning as described above; m groups $R_b$ each independently represent an organic group having at least one aliphatic hydrocarbon group having one or more branched chains, having a total number of branched chains of 3 or more and having a total number of carbon atoms of 14 or more and 300 or less; $R_2$ represents a hydrogen atom, or may represent a single bond together with $R_1$ and may form a fluorene ring together with Ring A; and Ring B optionally has at least one substituent selected from the group consisting of a halogen atom, a C1-6 alkyl group optionally substituted with one or more halogen atoms and a C1-6 alkoxy group optionally substituted with one or more halogen atoms, in addition to m groups $QR_b$ and $R_2$.)

and the organic group having at least one aliphatic hydrocarbon group having one or more branched chains, having a total number of branched chains of 3 or more and having a total number of carbon atoms of 14 or more and 300 or less represented by $R_a$ and $R_b$ is a group having 3 or more the same or different divalent groups represented by the formula (b):

[Chemical Formula 27]

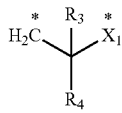

(b)

(wherein, * represents the binding position to an adjacent atom; $R_3$ and $R_4$ each independently represent a hydrogen atom or a C1-4 alkyl group; $X_1$ represents a single bond, a C1-4 alkylene group or an oxygen atom. However, $R_3$ and $R_4$ are not simultaneously hydrogen atoms.)]
(wherein, each of the formula is shown in the condition before binding to a carboxyl group, an amino group or a hydroxyl group of an amino acid, a peptide or an amino acid amide or to a linker.).

[7] The peptide synthesis method according to the above [1], wherein the carrier for liquid phase peptide synthesis is a carrier derived from a compound selected from the group consisting of

[Chemical Formula 28]

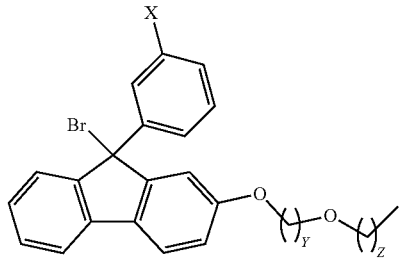

(wherein, X is a halogen, Y is an integer of 8 to 12, Z is an integer of 17 to 29.),

[Chemical Formula 29]

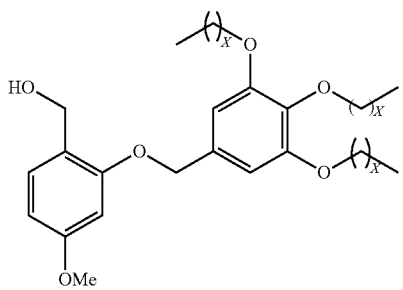

(wherein, groups X are each independently integers of 7 to 21.),

[Chemical Formula 30]

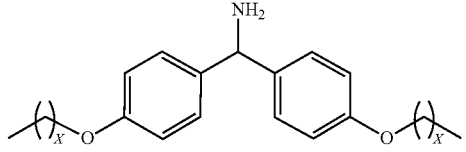

(wherein, groups X are each independently integers of 11 to 29.), and a branched chain-containing aromatic compound represented by

[Chemical Formula 31]

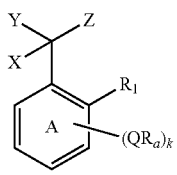

(Y)

[wherein, k groups Q each independently represent —O—; k groups $R_a$ each independently are groups represented by the following formula (Z):

[Chemical Formula 32]

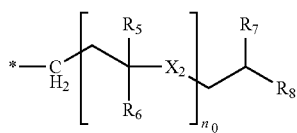

[wherein, * represents the binding position to Q; $n_0$ represents an integer of 2 to 40; $n_0$ groups $R_5$ and $R_6$ each independently represent a hydrogen atom or a C1-4 alkyl group (however, they are not simultaneously hydrogen atoms); $n_0$ groups $X_2$ each independently represent a single bond or a C1-4 alkylene group; and $R_7$ represents a hydrogen atom or a C1-4 alkyl group; $R_8$ represents a C1-4 alkyl group.]; k represents an integer of 1 to 4; $R_1$ is a hydrogen atom, alternatively, when Z is a group represented by the following formula (a), may represent a single bond together with $R_2$ and may form a fluorene ring together with Ring B; X represents a hydrogen atom or a phenyl group; Y represents a hydroxyl group or an —NHR group (R represents a hydrogen atom, an alkyl group or an aralkyl group); and Z is a hydrogen atom or a group represented by the formula (a):

[Chemical Formula 33]

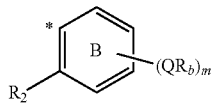

(a)

(wherein, * represents the binding position; m represents an integer of 0 to 4; m groups Q represent the same meaning as described above; m groups $R_b$ each independently represent a group of the formula (Z); $R_2$ represents a hydrogen atom, or may represent a single bond together with $R_1$ and may form a fluorene ring together with Ring A; and Ring B is optionally further substituted with one or more halogen atoms, in addition to m groups $QR_b$ and $R_2$.)]
(wherein, each of the formula is shown in the condition before binding to a carboxyl group, an amino group, a thiol group or a hydroxyl group of an amino acid, a peptide or an amino acid amide or to a linker.).

[8] The peptide synthesis method according to the above [1], wherein the carrier for liquid phase peptide synthesis is a carrier derived from a compound having the following structure:

[Chemical Formula 34]

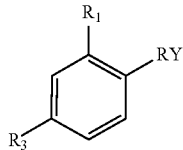

(wherein, $R_1$ and $R_3$ are alkoxy groups having 18 to 22 carbon atoms, and RY is a group represented by the following formula and binding to a carboxyl group, an amino group or a hydroxyl group of an amino acid, a peptide or an amino acid amide or to a linker,

[Chemical Formula 35]

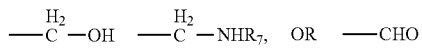

(wherein, $R_7$ represents a hydrogen atom or an alkyl group having 1 to 6 carbon atoms, wherein, the formula is shown in the condition before binding to a carboxyl group, an amino group or a hydroxyl group of an amino acid, a peptide or an amino acid amide or to a linker).

[9] The peptide synthesis method according to the above [1], wherein the carrier for liquid phase peptide synthesis is a carrier derived from a compound selected from the group consisting of

[Chemical Formula 36]

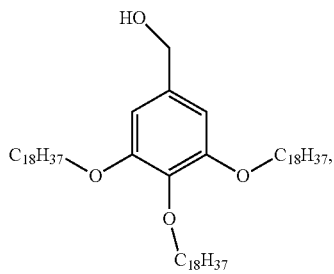

(3,4,5-trioctadecyloxybenzyl alcohol)

[Chemical Formula 37]

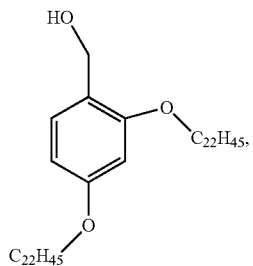

(2,4-didocosyloxybenzyl alcohol)

[Chemical Formula 38]

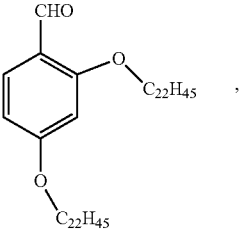

(2,4-didocosyloxybenzylaldehyde)

-continued

[Chemical Formula 39]

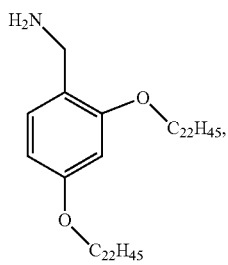

(2,4-didocosyloxybenzylamine)

[Chemical Formula 40]

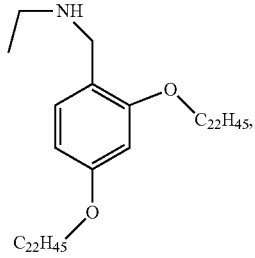

(N-ethyl-2,4-didocosyloxybenzylamine)

[Chemical Formula 41]

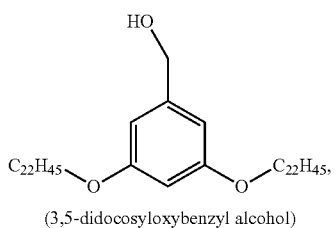

(3,5-didocosyloxybenzyl alcohol)

[Chemical Formula 42]

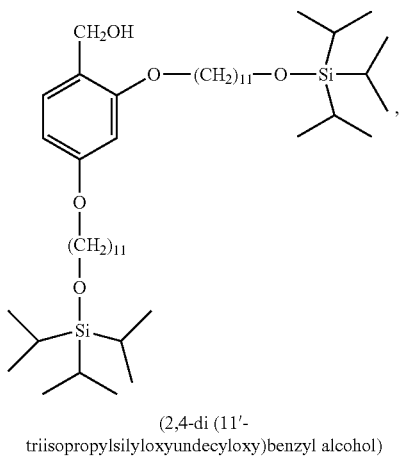

(2,4-di (11'-triisopropylsilyloxyundecyloxy)benzyl alcohol)

-continued

[Chemical Formula 43]

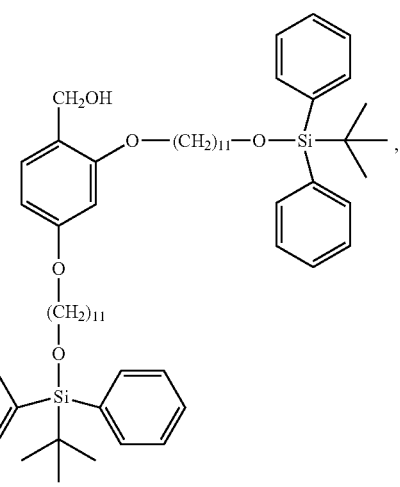

(2,4-di (11'-t-butyldiphenylsilyloxyundecyloxy)benzyl alcohol)

[Chemical Formula 44]

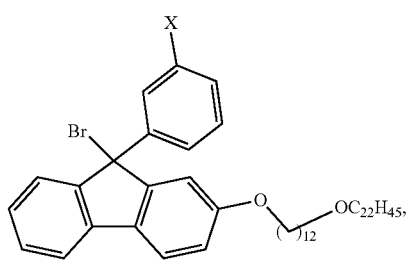

(wherein X is F or Cl.)

[Chemical Formula 45]

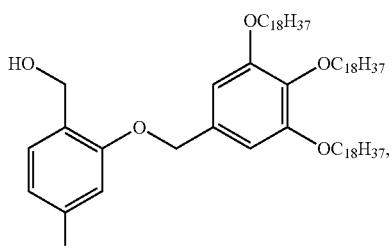

(2-(3',4',5'-trioctadecyloxybenzyl)-4-methoxybenzyl alcohol)

[Chemical Formula 46]

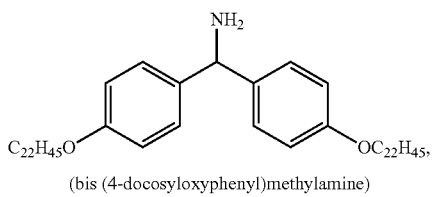

(bis (4-docosyloxyphenyl)methylamine)

-continued

[Chemical Formula 47]

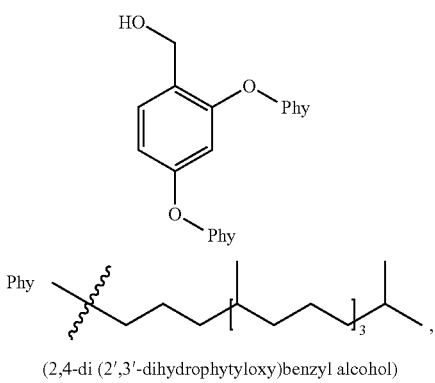

(2,4-di (2′,3′-dihydrophytyloxy)benzyl alcohol)

[Chemical Formula 48]

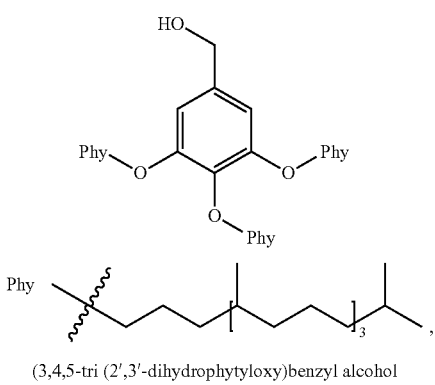

(3,4,5-tri (2′,3′-dihydrophytyloxy)benzyl alcohol

[Chemical Formula 49]

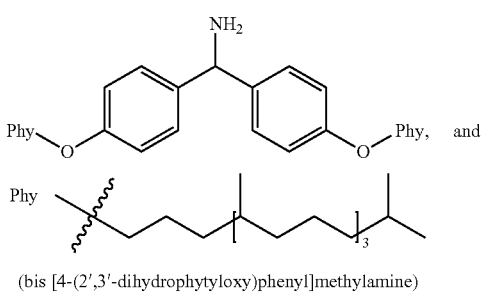

(bis [4-(2′,3′-dihydrophytyloxy)phenyl]methylamine)

[Chemical Formula 50]

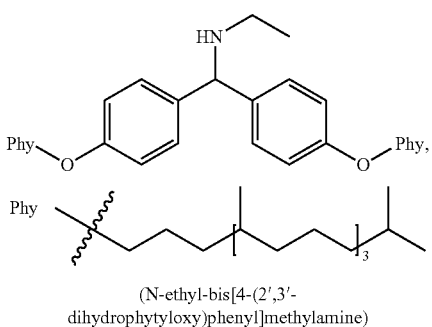

(N-ethyl-bis[4-(2′,3′-dihydrophytyloxy)phenyl]methylamine)

(wherein, each of the formula is shown in the condition before binding to a carboxyl group, an amino group, a thiol group or a hydroxyl group of an amino acid, a peptide or an amino acid amide or to a linker.).

[10] The peptide synthesis method according to the above [1], wherein the carrier for liquid phase peptide synthesis is a carrier derived from a compound selected from the group consisting of

[Chemical Formula 51]

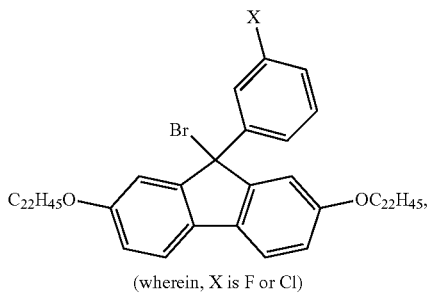

(wherein, X is F or Cl)

[Chemical Formula 52]

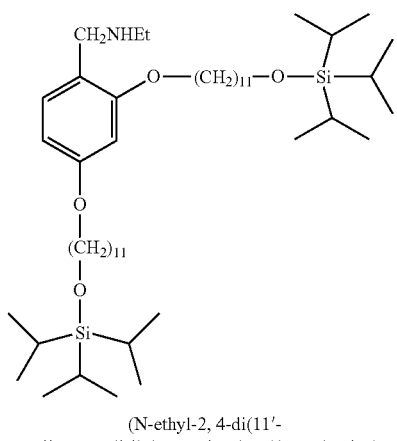

(N-ethyl-2, 4-di(11′-triisopropylisilyloxyundecyloxy)benzylamine)

[Chemical Formula 53]

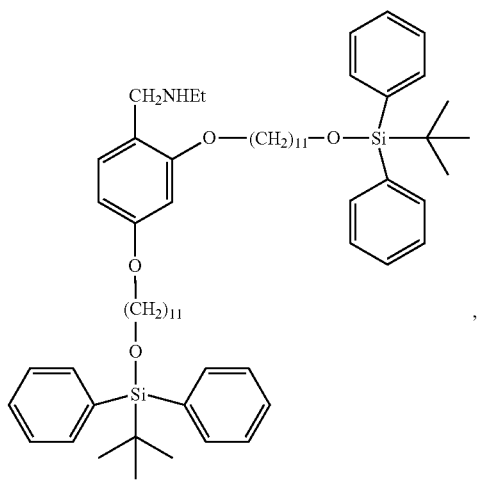

(N-ethyl-2, 4-di(11′-t-butyldiphenylsilyloxyundecyloxy)benxylamine)

-continued

[Chemical Formula 54]

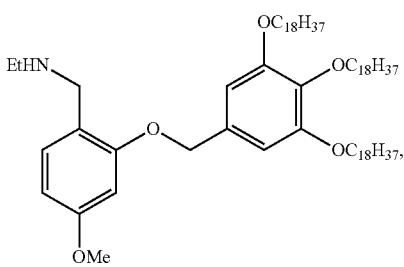

(N-ethyl-2-(3', 4', 5'-trioctadecyloxybenzyloxy)-4-methoxybenzylamine)

[Chemical Formula 55]

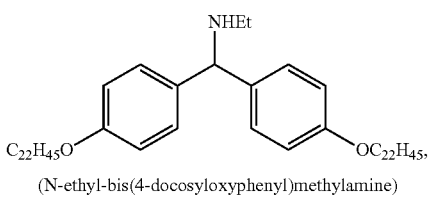

(N-ethyl-bis(4-docosyloxyphenyl)methylamine)

[Chemical Formula 56]

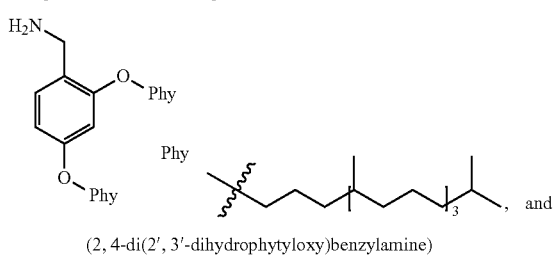

(2, 4-di(2', 3'-dihydrophytyloxy)benzylamine)

[Chemical Formula 57]

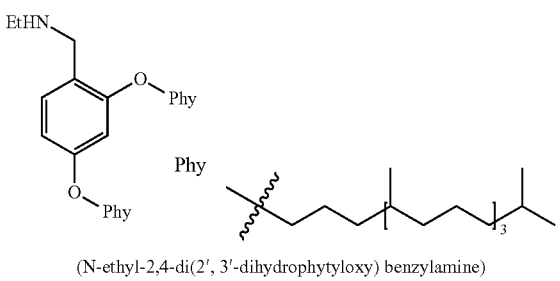

(N-ethyl-2,4-di(2', 3'-dihydrophytyloxy) benzylamine)

(wherein, each of the formula is shown in the condition before binding to a carboxyl group of an amino acid or a peptide.).

[11] The peptide synthesis method according to any one of [1] to [10], wherein the organic solvent or mixed solution of organic solvents is at least one organic solvent selected from the group consisting of THF, DMF, cyclohexane, CPME, MTBE, 2-methylTHF, 4-methylTHP, isopropyl acetate, DCM and N-methylpyrrolidone, or a mixed solution composed of two or more of them.

[12] The peptide synthesis method according to any one of [1] to [11], wherein the water-soluble amine is a water-soluble amine having two or more value and having at least one primary or secondary amino group, and selected from the group consisting of preferably 1-methylpiperazine, 4-aminopiperidine, diethylenetriamine, triaminoethylamine, 1-ethylpiperazine, N,N-dimethylethylenediamine, ethylenediamine and piperazine, more preferably 1-methylpiperazine, 4-aminopiperidine, N,N-dimethylethylenediamine and diethylenetriamine, and further preferably 1-methylpiperazine.

[13] The peptide synthesis method according to any one of the above [1] to [12], wherein the amine equivalent of the water-soluble amine in the step b is 1 to 10 equivalents (preferably 1 to 6 equivalents, more preferably 1 to 4 equivalents) with respect to the amino acid equivalent theoretically remaining after the condensation reaction in the step a.

[14] The peptide synthesis method according to any one of the above [1] to [13], wherein the amine equivalent of the water-soluble amine in the step c is 5 to 30 equivalents (preferably 5 to 20 equivalents, more preferably 10 to 20 equivalents) with respect to the amount of the Fmoc group existing in the system.

[15] The peptide synthesis method according to any one of the above [1] to [14], wherein pH of the acidic aqueous solution in the step d is 1 to 5 (preferably 1 to 4, more preferably 1 to 3).

[16] The peptide synthesis method according to any one of the above [1] to [15], comprising performing the repetition of the steps once or more times using the carrier-protected peptide obtained by the steps.

[17] The peptide synthesis method according to any one of the above [1] to [16], wherein the steps and conducted in one pot.

[18] Use of the peptide synthesis method according to any one of the above [1] to [17], for synthesizing a peptide having the following sequence: H-dArg-Arg-Pro-Hyp-Gly-Thi-Ser-dTic-Oic-Arg-OH (sequence ID No: 1).

Advantageous Effect of the Invention

The peptide synthesis method of the present invention can simultaneously solve the problem of an amino acid active ester and the problem of DBF existing in the reaction system and can reduce the solid-liquid separation operation works, by a simple means. According to the present invention, the process time of peptide synthesis can be shortened, and use of a solvent can be reduced by reducing the solid-liquid separation operation works.

DESCRIPTION OF EMBODIMENTS

Hereinafter, the present invention will be illustrated and described in detail with reference to the exemplary embodiments, along with the preferred methods and materials which can be used in practice of the present invention.

Unless otherwise specified in the sentences, any technical terms and scientific terms used in the present specification, have the same meaning as those generally understood by those of ordinary skill in the art to which the present invention belongs. Any materials and methods equivalent or similar to those described in the present specification can be used for practicing the present invention.

All publications and patents cited herein in connection with the present invention described herein are incorporated herein by reference, for example, as indicating methodology, materials, etc. that can be used in the present invention.

When the expression "X to Y" is used in the present specification, it is used to include X as the lower limit and Y as the upper limit. In the present specification, "about" is used in the sense of allowing ±10%.

The amino acid serving as a structural unit of the peptide synthesized by the method of the present invention may be a natural amino acid or an unnatural amino acid, may be an L-type amino acid or a D-type amino acid, and may also be a mixture of these amino acids. The unnatural amino acid is not particularly limited, and a known unnatural any amino acid or an amino acid to which any modification is applied by referring to a known technique may be used.

The known unnatural amino acids include, but are not limited to, for example, N-methyl modified amino acids, N-2,4-dimethoxybenzyl modified amino acids, α-methylalanine, D-1,2,3,4-tetrahydroisoquinoline-3-carboxylic acid, and L-octahydroindoline-2-carboxylic acid.

Amino acids obtained by applying any modification to natural or unnatural amino acids can also be used in the method of the present invention. The any modification is not particularly limited, and any modifications that can be applied to an amino acid using a known or common technique in the technical field related to amino acid synthesis can be used without limitation. Examples thereof include addition of a low molecular weight organic compound, phosphorylation, biotinylation, PEGylation, glycosylation and fluorescent modification.

In one embodiment of the present invention, the present invention is a peptide synthesis method comprising a step of condensing an amino acid, a peptide or an amino acid amide protected with a specific carrier for liquid phase peptide synthesis with an N-Fmoc-protected amino acid or peptide, a step of quenching an active ester remaining after the condensation reaction, a step of deprotection of Fmoc group from the condensed N-Fmoc-carrier-protected peptide, and a step of neutralizing the reaction solution with an acid before washing with an acidic aqueous solution, wherein a water-soluble amine is used after the condensation step and during the step of deprotection of Fmoc group.

In another embodiment of the present invention, the present invention is a peptide synthesis method wherein the peptide synthesis method is carried out in one pot.

In yet another embodiment of the present invention, the present invention is a peptide synthesis method wherein the peptide synthesis method is carried out continuously.

In another embodiment of the present invention, the present invention is a peptide synthesis method for obtaining a peptide in which the carboxyl group terminal is amidated, by using a carrier having a reactive group containing an amino group as the reactive group capable of binding to a carboxyl group of an amino acid or a peptide, in the peptide synthesis method.

The peptide synthesis method of the present invention will be described below.

1. N-Fmoc-Protected Amino Acid and Peptide

The amino acid in which an amino group is protected with a 9-fluorenylmethyloxycarbonyl (Fmoc) group (N-Fmoc-protected amino acid) or N-Fmoc-protected peptide means an amino acid or peptide in which an amino group of an amino acid or peptide is protected with an Fmoc group, while the carboxyl group is not protected and reactive. When an amino acid or peptide has one or more amino groups, at least one amino group may be protected with an Fmoc group.

When the N-Fmoc-protected amino acid or peptide has a functional group rich in reactivity such as a hydroxyl group, an amino group, a guanidyl group, a carboxyl group, a thiol group, an indole group, an imidazole group and the like, a general protective group used in peptide synthesis may be introduced into these functional groups, then, the protective group can be removed if necessary at any time point after completion of the reaction, to obtain a target compound.

The protective group for a hydroxyl group includes a tBu group, a Trt group, a Bz group, an acetyl group, a silyl group and the like, the protective group for an amino group includes a Boc group, an Fmoc group, a Cbz group, a Trt group, an Mmt group, an ivDde group and the like, the protective group for a guanidyl group includes a Pbf group, a Pmc group, a nitro group and the like, the protective group for a carboxyl group includes a tBu group, a methyl group, an ethyl group, a Bz group and the like, the protective group for a thiol group includes a Trt group, an Acm group, a tBu group, a S-tBu group and the like, the protective group for an indole group includes a Boc group and the like, and the protective group for an imidazole group includes a Boc group, a Bom group, a Bum group, a Trt group and the like.

2. Carrier-Protected Amino Acid, Peptide and Amino Acid Amide

The amino acid protected with a carrier for liquid phase peptide synthesis (carrier-protected amino acid) or carrier-protected peptide means an amino acid amide or peptide in which one reactive group of an amino acid or peptide is protected with a carrier for liquid phase peptide synthesis described below directly or via a linker, and at least one amino group is in a reactive state. In a preferable embodiment, a carboxyl group of an amino acid or peptide is protected with a carrier for liquid phase peptide synthesis described below, while the amino group is not protected and reactive.

The carrier-protected amino acid amide means an amino acid amide in which at least one amide group of an amino acid amide is protected with a carrier for liquid phase peptide synthesis described below directly or via a linker, and at least one amino group is not protected and reactive.

When the carrier-protected amino acid, the carrier-protected peptide or the carrier-protected amino acid amide has a functional group rich in reactivity such as a hydroxyl group, an amino group, a guanidyl group, a carboxyl group, a thiol group, an indole group, an imidazole group and the like, a general protective group used in peptide synthesis may be introduced into these functional groups, and the protective group can be removed if necessary after completion of the reaction, to obtain a target compound.

The protective group for a hydroxyl group includes a tBu group, a Trt group, a Bz group, an acetyl group, a silyl group and the like, the protective group for an amino group includes a Boc group, an Fmoc group, a Cbz group, a Trt group, an Mmt group, an ivDde group and the like, the protective group for a guanidyl group includes a Pbf group, a Pmc group, a nitro group and the like, the protective group for a carboxyl group includes a tBu group, a methyl group, an ethyl group, a Bz group and the like, the protective group for a thiol group includes a Trt group, an Acm group, a tBu group, a S-tBu group and the like, the protective group for an indole group includes a Boc group and the like, and the protective group for an imidazole group includes a Boc group, a Bom group, a Bum group, a Trt group and the like.

3. Carrier for Liquid Phase Peptide Synthesis

The carrier for liquid phase peptide synthesis used in the present invention is a compound binding to an amino acid, a peptide or an amino acid amide directly or via a linker to make them insoluble in water, and having a molecular weight of 300 or more. The carrier used in the present invention is preferably, not limited to, a compound having a property in which a dissolved condition and an insolubilized (crystallized or oil) condition changes reversibly depending on a change of the composition of a solvent in which the carrier is dissolved. In embodiments of the peptide synthesis method of the present invention, it is not necessary that the carrier be insolubilized, and additionally, it is not necessary to change the composition of the solvent so that the carrier becomes insoluble.

In the step of preparing the carrier-protected amino acid, the carrier-protected peptide or the carrier-protected amino acid amide used in the peptide synthesis method of the present invention, the carrier may be solidified (for example, crystallized), and further, in the step of recovering the carrier-protected peptide dissolved in an organic layer (a layer of an organic solvent or a mixture of organic solvents) obtained by the peptide synthesis method of the present invention, the carrier may be solidified (for example, crystallized), although the means is not limited to this.

The carrier for liquid phase peptide synthesis used in the present invention is preferably a carrier derived from the carrier compound described below. Hereinafter, the structure of the carrier that can be used in the present invention will be explained in the condition before binding to a carboxyl group, an amino group, a thiol group or a hydroxyl group of an amino acid, a peptide or an amino acid amide or to a linker.

3-1. Carrier Compound A

A compound having the following structure (in the present specification, referred to as "Ka" in some cases):

[Chemical Formula 58]

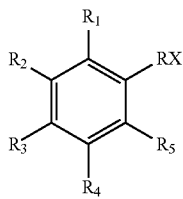

(wherein, $R_1$ and $R_5$ are hydrogen atoms, and $R_2$, $R_3$ and $R_4$ are alkoxy groups having 8 to 30 carbon atoms. In the formula, RX is a group represented by the following formula and binding to a carboxyl group, an amino group or a hydroxyl group of an amino acid, a peptide or an amino acid amide or to a linker,

[Chemical Formula 59]

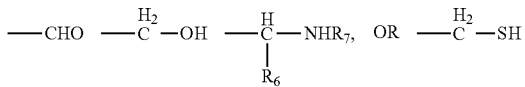

(wherein, $R_7$ represents a hydrogen atom, an alkyl group having 1 to 6 carbon atoms, a benzyl group or an alkoxy-substituted benzyl group, $R_6$ represents a hydrogen atom, a phenyl group or an alkoxy-substituted phenyl group.)).

In the formula, $R_2$, $R_3$ and $R_4$ are alkoxy group having more preferably 8 to 22 carbon atoms, and further preferably 12 to 18 carbon atoms.

In the formula, RX is preferably a hydroxymethyl group, an aminomethyl group or a mercaptomethyl group, and more preferably a hydroxymethyl group.

The preferable compound included in the formula is preferably 3,4,5-trioctadecyloxybenzyl alcohol, 3,4,5-trioctadecyloxybenzylamine or 3,4,5-trioctadecyloxybenzylthiol, more preferably 3,4,5-trioctadecyloxybenzyl alcohol or 3,4,5-trioctadecyloxybenzylamine, and still more preferably 3,4,5-trioctadecyloxybenzyl alcohol represented by the following formula.

[Chemical Formula 60]

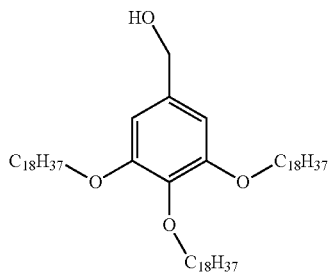

For binding of the compound (Ka) to a carboxyl group, an amino group or a hydroxyl group of an amino acid, a peptide or an amino acid amide or to a linker, methods generally used in peptide synthesis can be used also in the present invention without limitation, and for example, it can be conducted by esterification using DIPCI.

3-2. Carrier Compound B

A compound having the following structure (in the present specification, referred to as "Kb" in some cases):

[Chemical Formula 61]

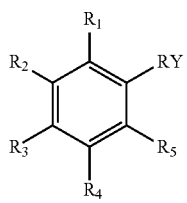

(wherein, $R_2$, $R_4$ and $R_5$ are hydrogen atoms, and $R_1$ and $R_3$ are alkoxy groups having 12 to 30 carbon atoms. In the formula, RY is a group represented by the following formula and binding to a carboxyl group, an amino group or a hydroxyl group of an amino acid, a peptide or an amino acid amide or to a linker,

[Chemical Formula 62]

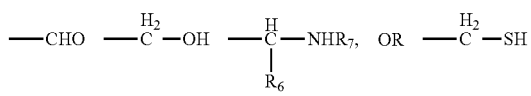

(wherein, $R_7$ represents a hydrogen atom, an alkyl group having 1 to 6 carbon atoms, a benzyl group or an alkoxy-substituted benzyl group, $R_6$ represents a hydrogen atom, a phenyl group or an alkoxy-substituted phenyl group.)).

In the formula, $R_1$ and $R_3$ are preferably alkoxy groups having 18 to 22 carbon atoms.

In the formula, RY is preferably a hydroxymethyl group, an aminomethyl group or a mercaptomethyl group, more preferably a hydroxymethyl group or an aminomethyl group.

Another preferable compound included in the formula is a compound having the following structure:

[Chemical Formula 63]

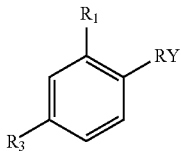

(wherein, $R_1$ and $R_3$ are alkoxy groups having 18 to 22 carbon atoms, and RY is a group represented by the following formula and binding to a carboxyl group, an amino group or a hydroxyl group of an amino acid, a peptide or an amino acid amide or to a linker,

[Chemical Formula 64]

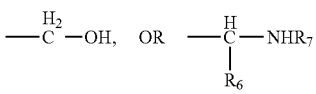

(wherein, $R_7$ represents a hydrogen atom, or an alkyl group having 1 to 6 carbon atoms, preferably having 1 to 3 carbon atoms.)).

The specific compound included in the formula is preferably 2,4-didocosyloxybenzyl alcohol, 2,4-didocosyloxybenzylamine, 2,4-didocosyloxybenzylthiol or N-ethyl-2,4-didocosyloxybenzylamine, more preferably 2,4-didocosyloxybenzyl alcohol represented by the following formula:

[Chemical Formula 65]

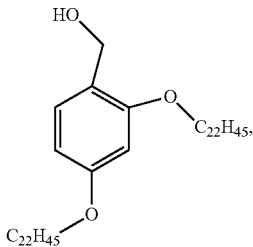

2,4-didocosyloxybenzylamine represented by the following formula:

[Chemical Formula 66]

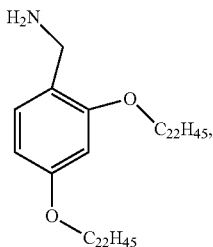

or N-ethyl-2,4-didocosyloxybenzylamine represented by the following formula.

[Chemical Formula 67]

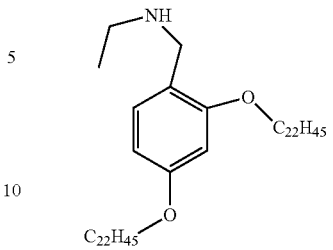

For binding of the compound (Kb) to a carboxyl group, an amino group or a hydroxyl group of an amino acid, a peptide or an amino acid amide or to a linker, methods generally used in peptide synthesis can be used also in the present invention without limitation, and for example, it can be conducted by esterification using DIPCI.

3-3. Carrier Compound C

A compound having the following structure (in the present specification, referred to as "Kc" in some cases):

[Chemical Formula 68]

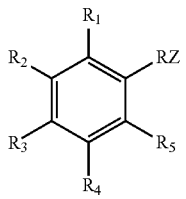

(wherein, $R_1$, $R_3$ and $R_5$ are hydrogen atoms, and $R_2$ and $R_4$ are alkoxy groups having 12 to 30 carbon atoms. In the formula, RZ is a group represented by the following formula and binding to a carboxyl group, an amino group or a hydroxyl group of an amino acid, a peptide or an amino acid amide or to a linker,

[Chemical Formula 69]

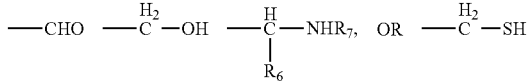

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group.)).

In the formula, $R_2$ and $R_4$ are preferably alkoxy groups having 18 to 22 carbon atoms.

In the formula, RZ is preferably a hydroxymethyl group, an aminomethyl group or a mercaptomethyl group, more preferably a hydroxymethyl group.

The compound included in the formula is preferably 3,5-didocosyloxybenzyl alcohol, 3,5-didocosyloxybenzylamine or 3,5-didocosyloxybenzylthiol, more preferably 3,5-didocosyloxybenzyl alcohol or 3,5-didocosyloxybenzylamine, and still more preferably 3,5-didocosyloxybenzyl alcohol represented by the following formula.

[Chemical Formula 70]

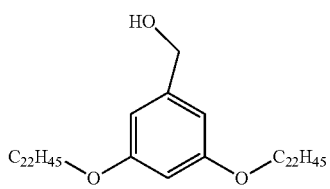

For binding of the compound (Kc) to a carboxyl group, an amino group or a hydroxyl group of an amino acid, a peptide or an amino acid amide or to a linker, methods generally used in peptide synthesis can be used also in the present invention without limitation, and for example, it can be conducted by esterification using DIPCI.

3-4. Carrier Compound D

A compound having the following structure (in the present specification, referred to as "KS" in some cases):

[Chemical Formula 71]

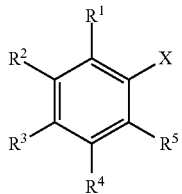

(wherein, X is a group representing —$CH_2ORa$ (wherein, Ra represents a hydrogen atom, a halogenocarbonyl group or an active ester type protective group), —$CH_2NHRb$ (wherein, Rb represents a hydrogen atom, a linear or branched alkyl group having 1 to 6 carbon atoms or an aralkyl group), a halogenomethyl group, a methyl azide group, a formyl group or an oxime, and binding to a carboxyl group, an amino group or a hydroxyl group of an amino acid, a peptide or an amino acid amide or to a linker; at least one of $R^1$, $R^2$, $R^3$, $R^4$ and $R^5$ represents a group represented by the following formula:

—O—$R^6$-Xa-A, and the residual groups represent a hydrogen atom, a halogen atom, an alkyl group having 1 to 4 carbon atoms or an alkoxy group having 1 to 4 carbon atoms; $R^6$ represents a linear or branched alkylene group having 1 to 16 carbon atoms, Xa represents O or CONRc (wherein, Rc represents a hydrogen atom or an alkyl group having 1 to 4 carbon atoms);

A represents any of the formula (1) to the formula (11),

[Chemical Formula 72]

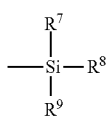

(1)

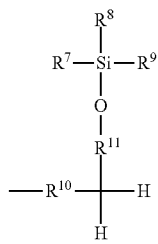

(2)

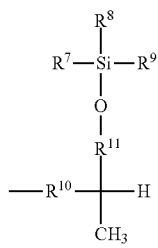

(3)

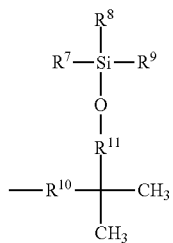

(4)

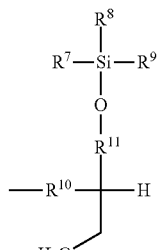

(5)

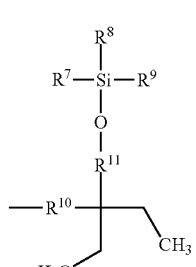

(6)

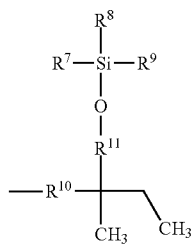

(7)

-continued

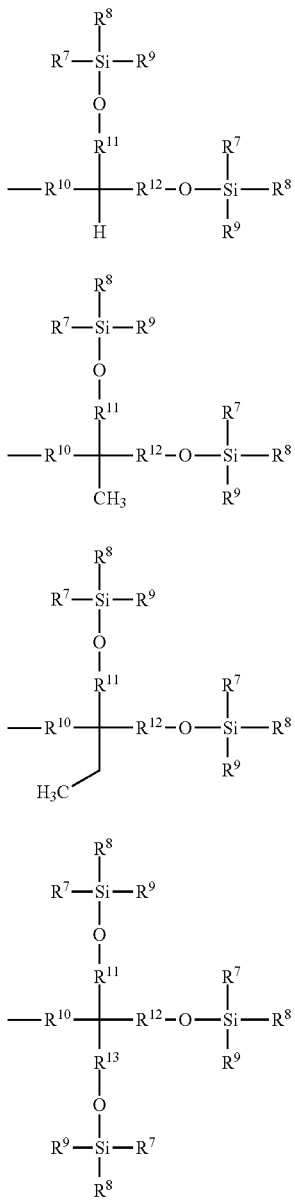

(wherein, $R^7$, $R^8$ and $R^9$ may be the same or different and represent a linear or branched alkyl group having 1 to 6 carbon atoms, or an aryl group optionally having a substituent, $R^{10}$ represents a single bond or a linear or branched alkylene group having 1 to 3 carbon atoms, and $R^{11}$, $R^{12}$ and $R^{13}$ may be the same or different and represent a linear or branched alkylene group having 1 to 3 carbon atoms.).

In the formula, X is preferably —$CH_2ORa$ (wherein, Ra represents a hydrogen atom, a halogenocarbonyl group or an active ester type protective group), —$CH_2NHRb$ (wherein, Rb represents a hydrogen atom, a linear or branched alkyl group having 1 to 6 carbon atoms or an aralkyl group) or a halogenomethyl group.

In the formula, $R^6$ is a linear or branched alkylene group having preferably 2 to 16 carbon atoms, more preferably 6 to 16 carbon atoms.

The preferable compound included in the formula is 2,4-di(11'-triisopropylsilyloxyundecyloxy)benzyl alcohol, 2,4-di(11'-t-butyldiphenylsilyloxyundecyloxy)benzyl alcohol, N-ethyl-2,4-di(11'-triisopropylsilyloxyundecyloxy)benzylamine or N-ethyl-2,4-di(11'-t-butyldiphenylsilyloxyundecyloxy)benzylamine represented by the following formula.

[Chemical Formula 73]

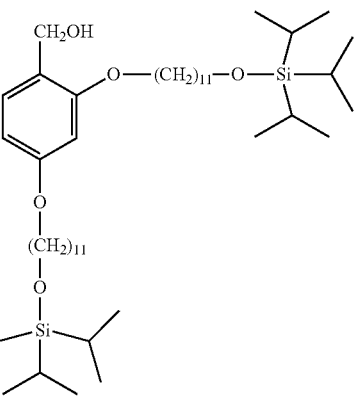

,

[Chemical Formula 74]

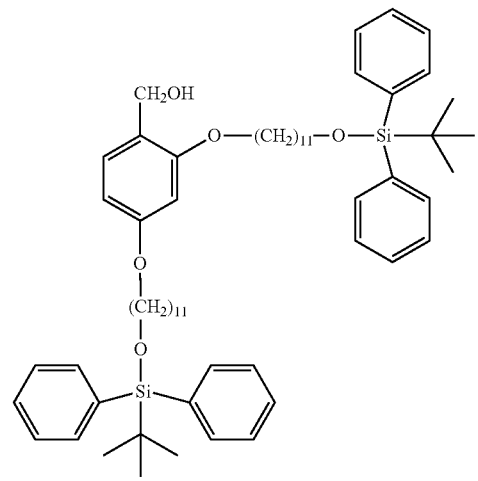

,

[Chemical Formula 75]

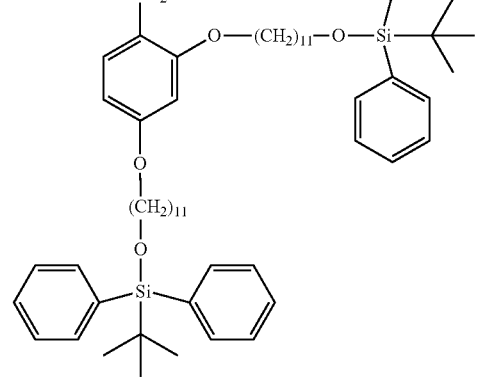

,

-continued

[Chemical Formula 76]

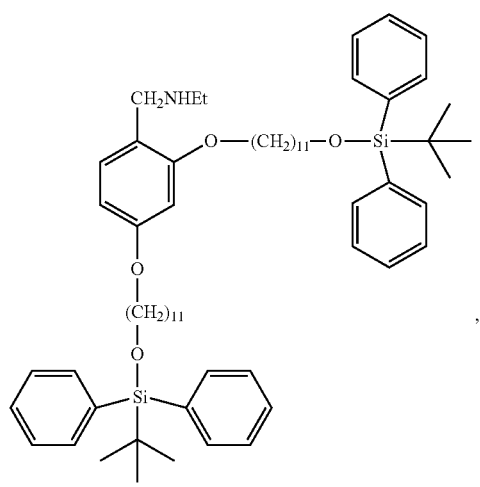

,

For binding of the compound (KS) to a carboxyl group, an amino group or a hydroxyl group of an amino acid, a peptide or an amino acid amide or to a linker, methods generally used in peptide synthesis can be used also in the present invention without limitation, and for example, it can be conducted by esterification using DIPCI.

3-5. Carrier Compound E

A compound having the following structure (in the present specification, referred to as "KJ1" in some cases):

A fluorene compound represented by the general formula (V):

[Chemical Formula 77]

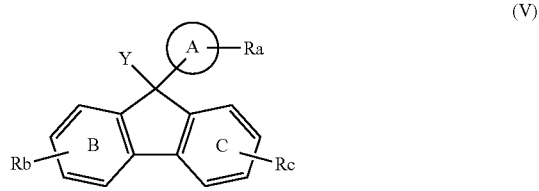

(V)

[wherein, Ring A represents an aromatic ring; Y is a hydroxyl group, a bromo group or a chloro group; Ra, Rb and Rc each independently represent an organic group having an aliphatic hydrocarbon group, a hydrogen atom or an electron withdrawing group, and at least one of Ra, Rb and Rc is an organic group having an aliphatic hydrocarbon group; Rings A, B and C each independently may have an electron withdrawing group], or the general formula (V'):

[Chemical Formula 78]

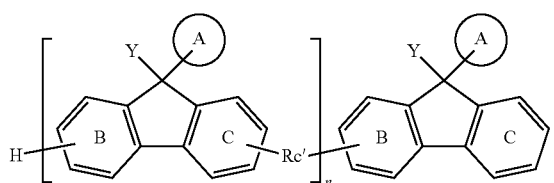

(V')

[wherein, Ring A represents an aromatic ring; Y is a hydroxyl group, a bromo group or a chloro group; n represents an integer of 1 to 19; Rc' is a divalent organic group having an aliphatic hydrocarbon group; Rings A, B and C each independently may have at least one selected from an organic group having an aliphatic hydrocarbon group and an electron withdrawing group; when a plurality of Rings A are present, the respective Rings A may be the same or different; when a plurality of groups Y are present, the respective groups Y may be the same or different; when a plurality of groups Rc' are present, the respective groups Rc' may be the same or different], wherein, the divalent organic group having an aliphatic hydrocarbon group is a group represented by the formula (a):

[Chemical Formula 79]

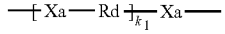

(a)

(wherein, Xa is not present or represents —O—, —S—, —NHCO— or —CONH—; Rd represents an aliphatic hydrocarbon group having 5 or more carbon atoms; $k_1$ represents an integer of 1 to 10; when a plurality of groups Rd are present, the respective groups Rd may be the same or different; and when a plurality of groups Xa are present, the respective groups Xa may be the same or different.), wherein, the organic group having an aliphatic hydrocarbon group is at least one group selected from the group consisting of a group represented by the formula (b):

[Chemical Formula 80]

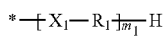

(b)

(wherein, * represents the binding position; $X_1$ is —O—; $R_1$ is an aliphatic hydrocarbon group having 5 to 60 carbon atoms; and $m_1$ is 1.), a group represented by the formula (c):

[Chemical Formula 81]

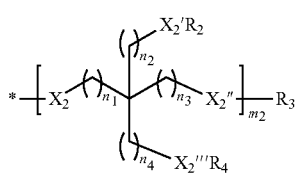

(c)

(wherein, * represents the binding position; $X_2$, $X_2'$, $X_2''$ and $X_2'''$ are —O—; $R_2$ and $R_4$ are each independently aliphatic hydrocarbon groups having 5 to 60 carbon atoms; $R_3$ is an organic group having an aliphatic hydrocarbon group having 5 to 60 carbon atoms; $n_1$, $n_2$, $n_3$ and $n_4$ are 1; and $m_2$ is 1), and a group represented by the formula (d):

[Chemical Formula 82]

(d)

(wherein, * represents the binding position; $X_8$ represents —O—; $m_3$ is 2 or 3; $n_5$ is 1; $n_6$ is 3; $X_7$ is —O—; $m_3$ groups $R_{12}$ are each independently alkyl groups having 4 to 30 carbon atoms), existing at the 2-position and/or the 7-position of the fluorene compound].

The preferable compound included in the formula is represented by the following formula.

[Chemical Formula 83]

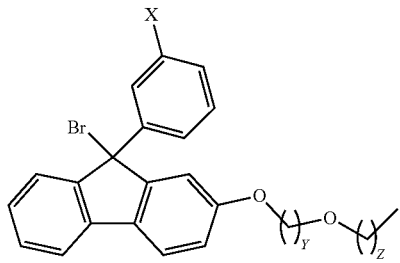

(wherein, X is a halogen, Y is an integer of 8 to 12, and Z is an integer of 17 to 29), or

[Chemical Formula 84]

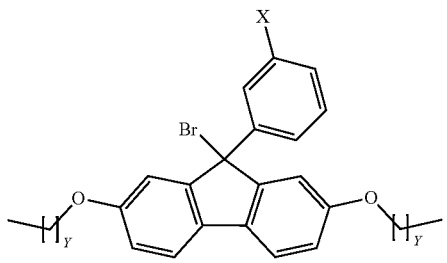

(wherein, X is a halogen, and Y is an integer of 18 to 22).

In the formula, X is preferably F or Cl, and more preferably F.

The most preferable compound is represented by the following formula.

[Chemical Formula 85]

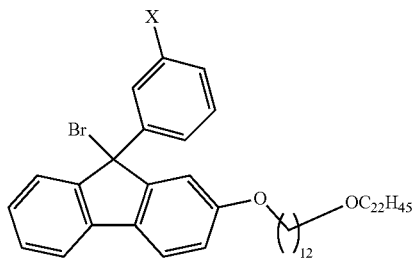

(wherein, X is F or Cl), or

[Chemical Formula 86]

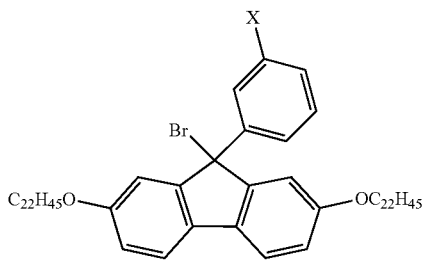

(wherein, X is F or Cl)

For binding of the compound (KJ1) to a carboxyl group, an amino group, a thiol group or a hydroxyl group of an amino acid, a peptide or an amino acid amide or to a linker, methods generally used in peptide synthesis can be used also in the present invention without limitation, and for example, it can be conducted by esterification using a base catalyst.

3-5. Carrier Compound F

A compound having the following structure (in the present specification, referred to as "KJ2" in some cases):

A benzyl compound represented by

[Chemical Formula 87]

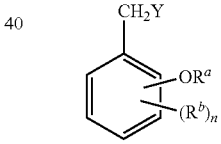
(W)

[wherein, Y represents a hydroxyl group or an NHR group (R represents a hydrogen atom, an alkyl group or an aralkyl group); $R^a$ represents an organic group having an aliphatic hydrocarbon group selected from the group consisting of a group represented by the formula (a):

[Chemical Formula 88]

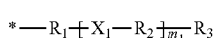
(a)

[wherein, * represents the binding position; $m_1$ represents an integer of 1 to 10; $m_1$ groups $X_1$ each independently represent a single bond or represent —O—, —S—, —COO—, —OCONH—, —NHCO— or —CONH—; $R_1$ and $m_1$ groups $R_2$ each independently represent a divalent aliphatic hydrocarbon group having 5 or more carbon atoms; and $R_3$ is a hydrogen atom or a group represented by the formula (W'):

[Chemical Formula 89]

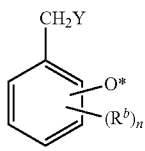

(W')

(wherein, * represents the binding position; n groups $R^b$ each independently represent an alkoxy group having 1 to 6 carbon atoms, a halogen atom, or an alkyl group having 1 to 6 carbon atoms optionally substituted with one or more halogen atoms; and n represents an integer of 0 to 4)];

a group represented by the formula (b):

[Chemical Formula 90]

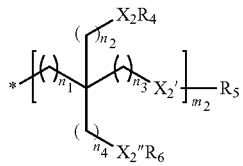

(b)

(wherein, represents the binding position; $m_2$ represents 1 or 2; $n_1$, $n_2$, $n_3$ and $n_4$ each independently represent an integer of 0 to 2; $m_2$ groups $X_2$, $m_2$ groups $X_2'$ and $m_2$ groups $X_2''$ each independently represent a single bond or represent —O—, —S—, —COO—, —OCONH—, —NHCO— or —CONH—; $m_2$ groups $R_4$ and $m_2$ groups $R_6$ each independently represent an aliphatic hydrocarbon group having 5 or more carbon atoms; $R_5$ represents an aliphatic hydrocarbon group having 5 or more carbon atoms);

a group represented by the formula (c):

[Chemical Formula 91]

(c)

(wherein, * represents the binding position; $m_3$ represents an integer of 0 to 15; $n_5$ represents an integer of 0 to 11; $n_6$ represents an integer of 0 to 5; $m_3$ groups $X_3$ each independently represent a single bond or represent —O—, —S—, —COO—, —OCONH—, —NHCO— or —CONH—; and $m_3$ groups $R_7$ each independently represent a hydrogen atom, a methyl group or an aliphatic hydrocarbon group having 5 or more carbon atoms); and a group represented by the formula (d):

[Chemical Formula 92]

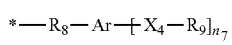

(d)

(wherein, * represents the binding position; $n_7$ groups $X_4$ each independently represent a single bond or represent —O—, —S—, —COO—, —OCONH—, —NHCO— or —CONH—; $R_8$ represents a divalent aliphatic hydrocarbon group; $n_7$ groups $R_9$ each independently represent a monovalent aliphatic hydrocarbon group; $n_7$ represents an integer of 1 to 5; and Ar represents an arylene group.), the total number of carbon atoms in the organic group is 30 or more; n groups $R^b$ each independently represent an alkoxy group having 1 to 6 carbon atoms, a halogen atom, or an alkyl group having 1 to 6 carbon atoms optionally substituted with one or more halogen atoms; and n represents an integer of 0 to 4.].

The preferable compound included in the formula is represented by the following formula.

[Chemical Formula 93]

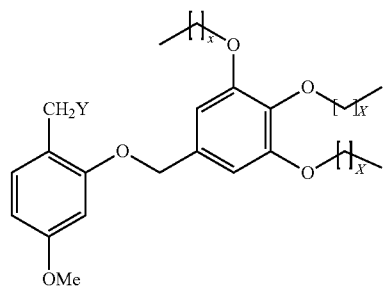

(wherein, groups X are each independently integers of 7 to 21, Y represents a hydroxyl group or an —NHR group (R represents a hydrogen atom, an alkyl group or an aralkyl group))).

The most preferable compound is 2-(3',4',5'-trioctadecyloxybenzyl)-4-methoxybenzyl alcohol or N-ethyl-2 (3',4',5'-trioctadecyloxybenzyloxy)-4-methoxybenzylamine represented by the following formula.

[Chemical Formula 94]

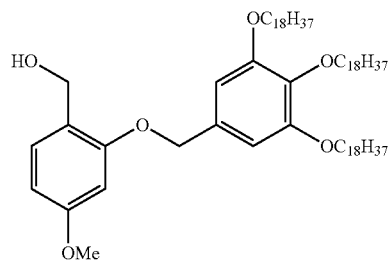

[Chemical Formula 95]

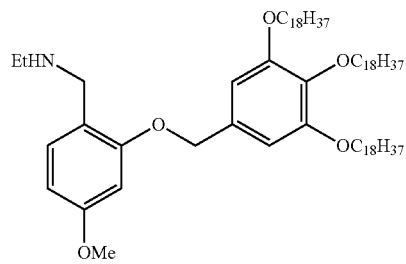

For binding of the compound (KJ2) to a carboxyl group, an amino group or a hydroxyl group of an amino acid, a peptide or an amino acid amide or to a linker, methods generally used in peptide synthesis can be used also in the present invention without limitation, and for example, it can be conducted by esterification using DIPCI.

3-6. Carrier Compound G

A compound having the following structure (in the present specification, referred to as "KJ3" in some cases):

A diphenylmethyl compound represented by

[Chemical Formula 96]

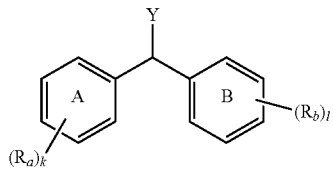

(X)

[wherein, Y represents a hydroxyl group or an —NHR group (R represents a hydrogen atom, an alkyl group or an aralkyl group); k and l each independently represent an integer of 0 to 5, providing k+l is not 0; k groups $R_a$ and l groups $R_b$ each independently represent an organic group having an aliphatic hydrocarbon group having 5 or more carbon atoms selected from the group consisting of a group represented by the formula (a):

[Chemical Formula 97]

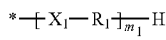

(a)

(wherein, * represents the binding position; $m_1$ represents an integer of 1 to 10; $m_1$ groups $X_1$ each independently are not present or represent —O—, —S—, —COO—, —OCONH— or —CONH—; $m_1$ groups $R_1$ each independently represent a divalent aliphatic hydrocarbon group having 5 or more carbon atoms.), a group represented by the formula (b):

[Chemical Formula 98]

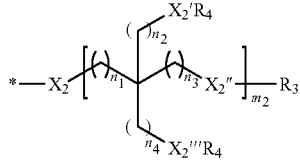

(b)

(wherein, represents the binding position; $m_2$ represents an integer of 1 to 2; $m_2$ groups $n_1$, $n_2$, $n_3$ and $n_4$ each independently represent an integer of 0 to 2; $m_2$ groups $X_2$, $m_2$ groups $X_2'$, $m_2$ groups $X_2'''$ and $m_2$ groups $X_2''$ each independently are not present or represent —O—, —S—, —COO—, —OCONH— or —CONH—; $m_2$ groups $R_2$ and $R_4$ each independently represent a hydrogen atom, a methyl group or an aliphatic hydrocarbon group having 5 or more carbon atoms; and $R_3$ represents an aliphatic hydrocarbon group having 5 or more carbon atoms.), and a group represented by the formula (e):

[Chemical Formula 99]

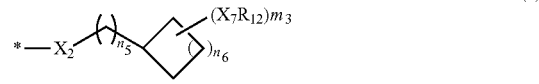

(e)

(wherein, * represents the binding position; $m_3$ represents an integer of 0 to 15; $n_5$ represents an integer of 0 to 11; $n_6$ represents an integer of 0 to 5; $X_2$ is not present or represents —O—, —S—, —NHCO— or —CONH—; $m_3$ groups $X_7$ each independently are not present or represent —O—, —S—, —COO—, —OCONH—, —NHCO— or —CONH—; $m_3$ groups $R_{12}$ each independently represent a hydrogen atom, a methyl group or an aliphatic hydrocarbon group having 5 or more carbon atoms), wherein the total number of carbon atoms of all aliphatic hydrocarbon groups in the organic group having (k+l) aliphatic hydrocarbon groups is 16 or more; Ring A optionally further has a substituent in addition to $R_a$; Ring B optionally further has a substituent in addition to $R_b$.].

The preferable compound included in the formula is represented by the following formula.

[Chemical Formula 100]

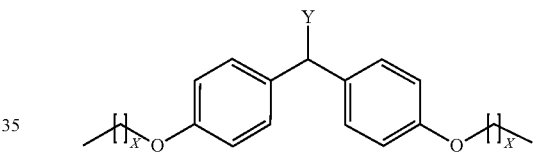

(wherein, groups X are each independently integers of 11 to 29, and Y represents an —NHR group (R represents a hydrogen atom, an alkyl group or an aralkyl group)).

The most preferable compound is bis(4-docosyloxyphenyl)methylamine or N-ethyl-bis(4-docosyloxyphenyl)methylamine represented by the following formula.

[Chemical Formula 101]

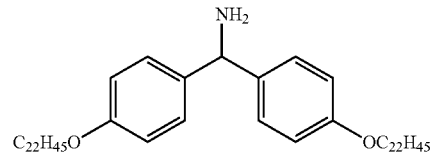

[Chemical Formula 102]

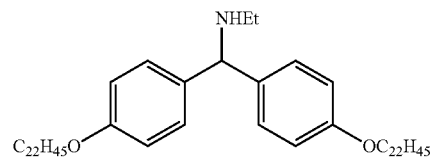

For binding of the compound (KJ3) to a carboxyl group of an amino acid, a peptide or an amino acid amide, methods generally used in peptide synthesis can be used also in the present invention without limitation, and for example, it can be conducted by amidation using DIPCI/HOBt.

3-7. Carrier Compound H

A compound having the following structure (in the present specification, referred to as "KJ4" in some cases):

A branched chain-containing aromatic compound represented by

[Chemical Formula 103]

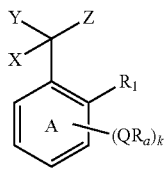

(Y)

[wherein, k groups Q each independently represent a single bond or represent —O—, —S—, —C(=O)O—, —C(=O)NH— or —NH—; k groups $R_a$ each independently represent an organic group having at least one aliphatic hydrocarbon group having one or more branched chains, having a total number of branched chains of 3 or more and having a total number of carbon atoms of 14 or more and 300 or less; k represents an integer of 1 to 4; $R_1$ is a hydrogen atom, alternatively, when Z is a group represented by the following formula (a), may represent a single bond together with $R_2$ and may form a fluorene ring together with Ring B; Ring A optionally has at least one substituent selected from the group consisting of a halogen atom, a C1-6 alkyl group optionally substituted with one or more halogen atoms and a C1-6 alkoxy group optionally substituted with one or more halogen atoms, in addition to $R_1$, k groups $QR_a$ and C(X)(Y)Z; X represents a hydrogen atom or a phenyl group; Y represents a hydroxyl group or an —NHR group (R represents a hydrogen atom, an alkyl group or an aralkyl group); and Z represents a hydrogen atom or a group represented by the formula (a):

[Chemical Formula 104]

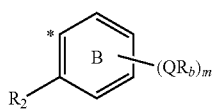

(a)

(wherein, represents the binding position; m represents an integer of 0 to 4, m groups Q represent the same meaning as described above; m groups $R_b$ each independently represent an organic group having at least one aliphatic hydrocarbon group having one or more branched chains, having a total number of branched chains of 3 or more and having a total number of carbon atoms of 14 or more and 300 or less; $R_2$ represents a hydrogen atom, or may represent a single bond together with $R_1$ and may form a fluorene ring together with Ring A; and Ring B optionally has at least one substituent selected from the group consisting of a halogen atom, a C1-6 alkyl group optionally substituted with one or more halogen atoms and a C1-6 alkoxy group optionally substituted with one or more halogen atoms, in addition to m groups $QR_b$ and $R_2$.)

and the organic group having at least one aliphatic hydrocarbon group having one or more branched chains, having a total number of branched chains of 3 or more and having a total number of carbon atoms of 14 or more and 300 or less represented by $R_a$ and $R_b$ is a group having 3 or more the same or different divalent groups represented by the formula (b):

[Chemical Formula 105]

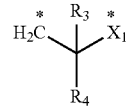

(b)

(wherein, * represents the binding position to an adjacent atom; $R_3$ and $R_4$ each independently represent a hydrogen atom or a C1-4 alkyl group; $X_1$ represents a single bond, a C1-4 alkylene group or an oxygen atom. However, $R_3$ and $R_4$ are not simultaneously hydrogen atoms.)].

The preferable compound included in the formula is represented by the following formula.

A branched chain-containing aromatic compound represented by

[Chemical Formula 106]

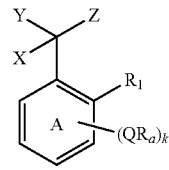

(Y)

[wherein, k groups Q each independently represent —O—; k groups $R_a$ each independently are groups represented by the following formula (Z):

[Chemical Formula 107]

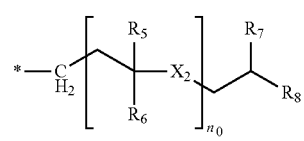

(Z)

[wherein, * represents the binding position to Q; $n_0$ represents an integer of 2 to 40; $n_0$ groups $R_5$ and $R_6$ each independently represent a hydrogen atom or a C1-4 alkyl group (however, they are not simultaneously hydrogen atoms); $n_0$ groups $X_2$ each independently represent a single bond or a C1-4 alkylene group; and $R_7$ represents a hydrogen atom or a C1-4 alkyl group; $R_8$ represents a C1-4 alkyl group.]; k represents an integer of 1 to 4; $R_1$ is a hydrogen atom, alternatively, when Z is a group represented by the following formula (a), may represent a single bond together with $R_2$ and may form a fluorene ring together with Ring B; X represents a hydrogen atom or a phenyl group; Y represents a hydroxyl group or an —NHR group (R represents a hydrogen atom, an alkyl group or an aralkyl group); and Z is a hydrogen atom or a group represented by the formula (a):

[Chemical Formula 108]

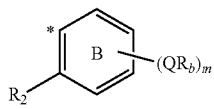

(a)

(wherein, * represents the binding position; m represents an integer of 0 to 4, m groups Q represent the same meaning as described above; m groups $R_b$ each independently represent a group of the formula (Z); $R_2$ represents a hydrogen atom, or may represent a single bond together with $R_1$ and may form a fluorene ring together with Ring A; and Ring B is optionally further substituted with one or more halogen atoms, in addition to m groups $QR_b$ and $R_2$.).

The further preferable compound included in the formula is 2,4-di(2',3'-dihydrophytyloxy)benzyl alcohol represented by the following formula:

[Chemical Formula 109]

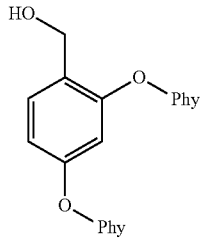

3,4,5-tri(2',3'-dihydrophytyloxy)benzyl alcohol represented by the following formula:

[Chemical Formula 110]

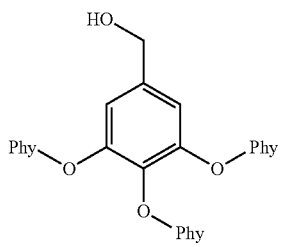

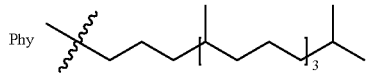

2,4-di(2',3'-dihydrophytyloxy)benzylamine represented by the following formula:

[Chemical Formula 111]

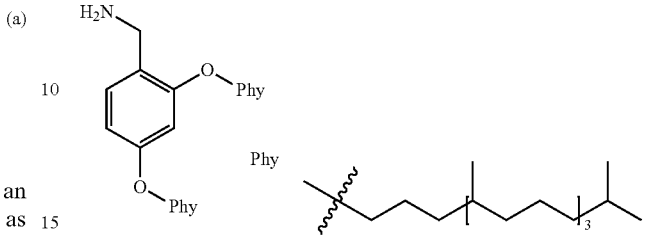

N-ethyl-2,4-di(2',3'-dihydrophytyloxy)benzylamine represented by the following formula:

[Chemical Formula 112]

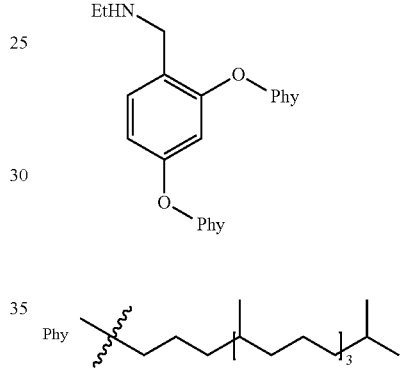

bis[4-(2',3'-dihydrophytyloxy)phenyl]methylamine represented by the following formula:

[Chemical Formula 113]

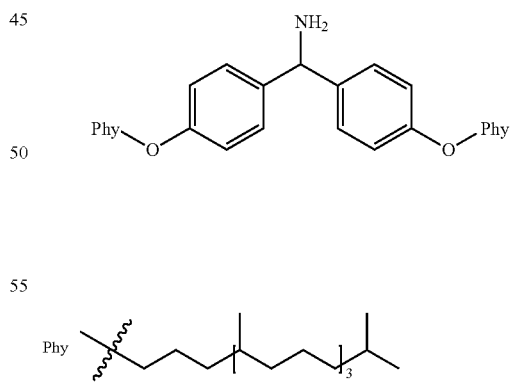

or N-ethyl-bis[4-(2',3'-dihydrophytyloxy)phenyl]methylamine represented by the following formula.

[Chemical Formula 114]

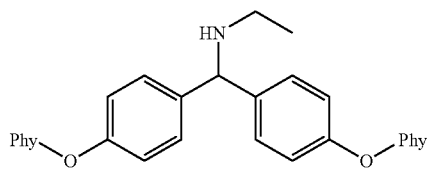

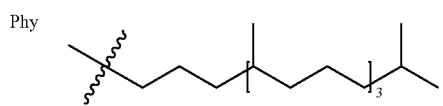

For binding of the compound (KJ4) to a carboxyl group of an amino acid, a peptide or an amino acid amide, methods generally used in peptide synthesis can be used also in the present invention without limitation, and for example, it can be conducted by amidation using DIPCI/HOBt.

4. Linker

In the carrier-protected amino acid, peptide or amino acid amide used in the present invention, the carrier is bonded directly or via a linker to an amino group, a carboxyl group, a thiol group or a hydroxyl group of an amino acid, a peptide or an amino acid amide.

The linker referred to herein is an organic group having two reactive groups one of which is bonded to any one group selected from the group consisting of one or several amino groups, one or several carboxyl groups, one or several thiol groups and one or several hydroxyl groups of an amino acid, a peptide or an amino acid amide, and the other of which is bonded to the carrier. In a preferable embodiment, the linker that can be used in the present invention is an organic group having a molecular weight of about 2000 or less (preferably about 1500 or less, more preferably about 1000 or less) and is a compound having in the molecule at least two groups which may be the same or different and selected from the group consisting of an amino group, a carboxyl group and a halomethyl group, as the reactive group. Examples thereof include, but not limited to, the following compounds.

[Chemical Formula 115]

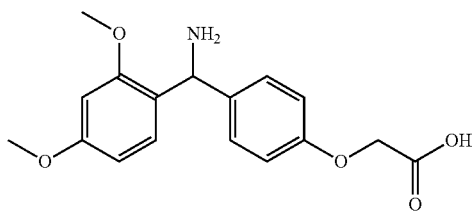

[Chemical Formula 116]

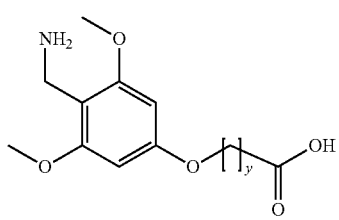

(wherein, Y is an integer of 1 to 6, preferably 1 to 4).

[Chemical Formula 117]

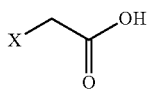

(wherein, X is a halogen atom, preferably Cl or Br).

[Chemical Formula 118]

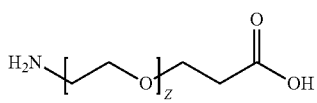

(wherein, Z is an integer of 2 to 40, preferably 2 to 35, more preferably 2 to 28).
(the structural formula of the linker is shown in the condition before binding to a carboxyl group, an amino group, a thiol group or a hydroxyl group of an amino acid, a peptide or an amino acid amide and before binding to a carrier.).

In preparation of the carrier-protected amino acid, peptide or amino acid amide containing the linker, the order of binding to the linker is not particularly limited, and one reactive group of the linker may be bonded to an amino acid, a peptide or an amino acid amide before binding the other reactive group to the carrier, alternatively, one reactive group of the linker may be bonded to the carrier before binding the other reactive group to an amino acid, a peptide or an amino acid amide.

The binding of one reactive group of the linker to an amino acid, a peptide or an amino acid amide can be conducted referring appropriately to known methods depending on the group of the linker and the group of an amino acid, a peptide or an amino acid amide to be mutually bonded. Examples thereof include, but not limited to, amidation using DIPCI/HOBt.

The binding of one reactive group of the linker to the carrier can be conducted referring appropriately to known methods depending on the group of the linker and the group of the carrier to be mutually bonded. Examples thereof include, but not limited to, esterification using DIPCI.

5. Solvent

The solvent used in the method of the present invention is not particularly limited, and solvents used in liquid phase peptide synthesis can be used. The solvent includes, but not limited to, for example, THF, DMF, cyclohexane, CPME, MTBE, 2-methylTHF, 4-methylTHP, isopropyl acetate, chloroform, dichloromethane and N-methylpyrrolidone, preferably, THF, DMF, cyclohexane, CPME, MTBE, 2-methylTHF, 4-methylTHP, isopropyl acetate and N-methylpyrrolidone. Further, a mixed solvent composed of two or more of the solvents may be used.

When the carrier is solidified (crystallized) for preparing the starting substances used in the peptide synthesis method of the present invention or for recovering the peptide synthesized using the peptide synthesis method of the present invention, a polar solvent is used. The polar solvent to be used includes, for example, methanol, ethanol, isopropanol, acetonitrile, propionitrile, DMF, dimethylacetamide, dimethyl sulfoxide, water and the like, and a mixed solvent composed of two or more of them. Particularly, methanol or acetonitrile is suitably used.

6. Peptide Synthesis Method

In the peptide synthesis method of the present invention, a series of steps from the step of condensation reaction, the step of deprotection of Fmoc group and the step of recovering the carrier-protected peptide can be carried out continuously without conducting a solid-liquid separation operation, and further, impurities generating in the synthesis step can be reduced or removed by liquid-liquid separation. Hence, it is suitable as a continuous peptide synthesis method.

Synthesis of a peptide by the peptide synthesis method of the present invention includes the following steps.

(i) Condensation Reaction Step

A step in which a carrier-protected amino acid, a carrier-protected peptide or a carrier-protected amino acid amide is condensed with an N-Fmoc-protected amino acid or an N-Fmoc-protected peptide, in an organic solvent or a mixed solution of organic solvents, in the presence of a condensing agent, to obtain an N-Fmoc-carrier-protected peptide, (ii) Scavenge Reaction Step A step in which a water-soluble amine (hereinafter, referred to as an amine scavenger in some cases) is added to the reaction solution after the condensation reaction, to form a scavenged body of an amino acid active ester, (iii) Deprotection of Fmoc Step A step in which an Fmoc group is detached from the protected N terminal, in the presence of a water-soluble amine, and (iv) Acidic Aqueous Solution Washing Step A step in which an acid is added to the reaction solution to neutralize it, and further, an acidic aqueous solution is added and the solution is washed, then, separated, and the aqueous layer is removed.

The step can be conducted in one pot since it does not need a solid-liquid separation operation accompanied by solidification (crystallization) of a carrier-protected amino acid, a carrier-protected peptide or a carrier-protected amino acid amide, and an N-Fmoc-carrier-protected peptide.

Further, by conducting the step, a carrier-protected peptide with an amino acid or peptide added compared to the start of the synthesis reaction can be recovered in the condition dissolved in an organic layer. Moreover, since impurities are reduced or removed from the organic layer containing the dissolved carrier-protected peptide, the next peptide synthesis reaction can be continuously performed in that state.

As a result, one embodiment of the peptide synthesis method of the present invention includes a peptide synthesis method comprising repeating steps (i) to (iv) a required number of times. By using the method of the present invention, continuous peptide synthesis can be conducted in one pot.

The carrier-protected amino acid, the carrier-protected peptide or the carrier-protected amino acid amide in the step (i) of the peptide synthesis method of the present invention can be produced referring appropriately to known methods used in peptide synthesis, depending on the carrier to be used. The method will be described below by taking a carrier-protected amino acid as an example. For example, the carrier can be bonded directly or via a linker to a carboxyl group, an amino group, a thiol group or a hydroxyl group of an amino acid. For example, an N-Fmoc-carrier-protected amino acid which is an intermediate in which the carrier is bonded to a carboxyl group of an amino acid can be produced by dissolving a carrier compound in a solvent such as THF and the like, adding an N-Fmoc-protected amino acid and a condensing agent, for example, DIPCI and performing condensation thereof, though the means is not limit to this. Alternatively, an N-Boc-carrier-protected amino acid which is an intermediate in which the carrier is bonded to a carboxyl group of an amino acid can be produced by dissolving a carrier compound in a solvent such as THF and the like, adding a Boc-protected amino acid and a condensing agent, for example, DIPCI and performing condensation thereof.

The N-Fmoc-carrier-protected amino acid or N-Boc-carrier-protected amino acid produced can be obtained at high purity preferably by solidifying (crystalizing) before recovering. For example, a reaction solution containing an N-Fmoc/Boc-carrier-protected amino acid is distilled off under reduced pressure, then, a solvent in which an N-Fmoc-carrier-protected amino acid or an N-Boc-carrier-protected amino acid is solidified (crystallized), for example, methanol or acetonitrile is added to the residue to cause deposition, and the precipitate is filtrated, then, suspended and washed with a solvent, and the resultant solid is dried, thus, an N-Fmoc/Boc-carrier-protected amino acid can be obtained, though the means is not limited to this.

A carrier-protected amino acid can be produced by removing the N terminal protective group from the thus obtained N-Fmoc-carrier-protected amino acid or N-Boc-carrier-protected amino acid referring appropriately to known methods used in peptide synthesis. For example, it can be produced by dissolving the N-Fmoc-carrier-protected amino acid in a solvent such as THF and the like, adding a Fmoc-deprotecting reagent Fmoc-deprotecting reagent such as DBU, piperazine and the like and performing the deprotection of Fmoc reaction, though the means is not limited to this. Alternatively, a carrier-protected amino acid can be produced by dissolving an N-Boc-carrier-protected amino acid in a solvent such as CPME and the like, adding a Boc deprotection reagent such as TFA and the like and performing the Boc deprotection reaction.

As another embodiment, a carrier-protected amino acid in which a carrier is bonded to an amino group of an amino acid can be produced by dissolving a carrier compound in a solvent such as THF and the like, adding an amino acid in which a carboxyl group has been protected previously, and a reducing agent, for example, sodium triacetoxyborohydride, and performing a reductive amination reaction, though the method for binding a carrier to an amino group of an amino acid is not limited to this.

Since the thus obtained carrier-protected amino acid can be prepared in a solution state, it can be subjected to the same acidic aqueous solution washing step as in the step (iv) of the present invention in that state, and the carrier-protected amino acid after performing the acidic aqueous solution washing can be used in the method of the present invention as the raw material for the step (i) of the method of the present invention. In such a case, peptide synthesis is possible in one pot, also including the carrier-protected amino acid preparation step.

Further, the resultant carrier-protected amino acid can also be solidified (crystallized) before recovering, and by this, it can be obtained at high purity. For example, a reaction solution containing a carrier-protected amino acid is distilled off under reduced pressure, then, a solvent in which the carrier is solidified (crystallized), for example, a methanol or acetonitrile is added to the residue to cause deposition, and the precipitate is filtrated, then, suspended and washed with a solvent, and the resultant solid is dried, thus, a carrier-protected amino acid can be obtained, though the means is not limited to this.

The thus obtained carrier-protected amino acid can be used as the starting substance in the peptide synthesis method of the present invention.

Accordingly, one embodiment of the peptide synthesis method of the present invention includes a peptide synthesis method further comprising a step of preparing a carrier-protected amino acid, before the steps (i) to (iv).

The carrier-protected peptide obtained by using the peptide synthesis method of the present invention can be recovered using known methods used in the peptide synthesis field. For example, the peptide can be recovered from a solvent by crystallizing it. For example, an organic layer containing the resultant carrier-protected peptide is distilled under reduced pressure to remove a solvent, then, a poor solvent, for example, cold acetonitrile is added to the residue to cause deposition, and the precipitate is filtrated, then, suspended and washed with a solvent, and the resultant solid is dried, thus, a carrier-protected peptide can be obtained, though the means is not limited to this.

Accordingly, one embodiment of the peptide synthesis method of the present invention includes a peptide synthesis method comprising a step of crystalizing and separating the carrier-protected peptide, after the steps (i) to (iv).

The respective steps will be explained below. In the following explanation, a carrier-protected peptide and an N-Fmoc-protected amino acid are described as examples, however, the carrier-protected peptide is an examples of the carrier-protected amino acid, the carrier-protected peptide or the carrier-protected amino acid amide which can be used in the present invention, and the N-Fmoc-protected amino acid is an example of the N-Fmoc-protected amino acid or the N-Fmoc-protected peptide which can be used in the present invention.

6-1. Condensation Reaction Step

In this step, an N-Fmoc-carrier-protected peptide having an increased number of the amino acid residue is obtained by mixing a carrier-protected peptide, and N-Fmoc-protected amino acid and a condensing agent (preferably, condensing agent and activating agent) in a solvent.

The method and order of adding components are not particularly limited, and methods generally used in a condensation step in peptide synthesis can be used.

The use amount of an N-Fmoc-protected amino acid with respect to a carrier-protected peptide is usually 1.01 to 4 equivalents, preferably 1.03 to 3 equivalents, more preferably 1.05 to 2 equivalents, and further preferably 1.1 to 1.5 equivalents. When smaller than this range, the unreacted carrier-protected peptide tends to remain, and missing of amino acids occurs easily. In the peptide synthesis method of the present invention, the unreacted amino acid active ester can be scavenged (captured) by a water-soluble amine to be added subsequently, to deactivate it. Hence, even if a larger amount of N-Fmoc-protected amino acid is used, the problem of remaining does not occur compared with conventional methods.

As the condensing agent, condensing agents generally used in peptide synthesis can be used also in the present invention without limitation, and examples thereof include, but not limited to, 4-(4,6-dimethoxy-1,3,5-triazin-2-yl)-4-methylmorpholinium chloride (DMT-MM), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), O-(6-chlorobenzotriazol-1-yl)-1,1,3,3-tetramethyluronium hexafluorophosphate (HBTU(6-Cl)), O-(benzotriazol-1-yl)-1,1,3,3-tetramethyluronium tetrafluoroborate (TBTU), O-(6-chlorobenzotriazol-1-yl)-1,1,3,3-tetramethyluronium tetrafluoroborate (TCTU), (1-cyano-2-ethoxy-2-oxoethylideneaminooxy)dimethylamino-morpholino-carbenium hexafluorophosphate (COMU), diisopropylcarbodiimide (DIPCI), dicyclohexylcarbodiimide (DCC) and 1-ethyl-3-(3-dimethylaminopropyl)carbodiimide hydrochloride (WSC), preferably, DMT-MM, HBTU, HATU, or COMU. The use amount of the condensing agent is usually 1 to 4 equivalents, preferably 1 to 2 equivalents, more preferably 1.05 to 1.3 equivalents with respect to the carrier-protected peptide.

In the condensation step, an activating agent is preferably added for promoting the reaction and for suppressing side reactions such as racemization and the like. Here, the activating agent is a reagent which, when coexisting with a condensing agent, guides an amino acid to a corresponding active ester, a symmetrical acid anhydride or the like to facilitate the formation of a peptide bond (amide bond). As the activating agent, activating agents generally used in peptide synthesis can be used also in the present invention without limitation, and examples thereof include HOBt, HOCt, HOAt, HOOBt, HOSu, HOPht, HONb, pentafluorophenol, ethyl cyanohydroxyimino acetate (Oxyma) and the like, preferably, HOBt, HOOBt, HOCt, HOAt, HONb, HOSu and Oxyma. The use amount of the activating agent is usually 1 to 4 equivalents, preferably 1 to 2 equivalents, and more preferably 1.05 to 1.3 equivalents with respect to the carrier-protected peptide.

As the solvent used in the condensation step, solvents generally used in peptide synthesis can be used also in the present invention without limitation, and examples thereof include, but not limited to, the solvents described above. The use amount of the solvent is an amount at which the concentration of a dissolved carrier-protected peptide or the like is usually 0.1 mM to 1 M, and preferably 1 mM to 0.5 M.

As the reaction temperature, temperatures generally used in peptide synthesis are used also in the present invention, and for example, it is usually in a range of −20 to 40° C., and preferably 0 to 30° C. The reaction time (time of 1 cycle) is usually 0.5 to 30 hours.

6-2. Scavenge Reaction Step

The peptide synthesis method of the present invention is characterized in that after the amino acid condensation reaction step, a water-soluble amine is added to the reaction system and the unreacted amino acid active ester is scavenged (captured). The water-soluble amine is bonded to an amino acid active ester to form a scavenged body, to deactivate the active ester. In the present specification, the water-soluble amine used in the present invention is called an amine scavenger in some cases.

The water-soluble amine as a scavenger which can be used in the present invention is preferably a water-soluble amine having two or more value and having at least one primary or secondary amino group, and examples thereof include 1-methylpiperazine, 4-aminopiperidine, diethylenetriamine, triaminoethylamine, 1-ethylpiperazine, N,N-dimethylethylenediamine, ethylenediamine and piperazine, preferably 1-methylpiperazine, 4-aminopiperidine, diethylenetriamine, N,N-dimethylethylenediamine and ethylenediamine, more preferably 1-methylpiperazine, 4-aminopiperidine, N,N-dimethylethylenediamine and diethylenetriamine, and further preferably 1-methylpiperazine.

The addition amount of a water-soluble amine in the step (ii) is usually 1 to 10 equivalents, preferably 1 to 6 equivalents, and more preferably 1 to 4 equivalents with respect to the theoretically remaining amino acid equivalent. When the amine addition amount is smaller than this range, scavenge (capture) of an amino acid active ester becomes insufficient, and double hit occurs in which the remaining amino acid active ester and the amino group regenerated in the subsequent step (iii) react together, to lower purity and yield, while when larger than this range, a deprotection of Fmoc reaction progresses simultaneously, and double hit occurs in which the remaining amino acid active ester reacts with the amino group regenerated, to lower purity and yield.

In the peptide synthesis method of the present invention, the next step of removing an Fmoc group from an N-Fmoc-carrier-protected peptide is conducted after scavenging (capturing) an amino acid active ester in the reaction system by an amine scavenger to form a scavenged body. By this, at the time of the deprotection of Fmoc reaction, the amino acid active ester in the reaction solution has been deactivated, and even when they are not removed from the reaction system, amino acid double hit can be prevented in the time of deprotection. Further, the amino acid active ester captured by a water-soluble amine can be easily removed in the subsequent washing step.

6-3. Deprotection of Fmoc Step

In the peptide synthesis method of the present invention, removal of an Fmoc group from an N-Fmoc-carrier-protected peptide is carried out in the presence of a water-soluble amine. In this step, a water-soluble amine is additionally added to the reaction system. The water-soluble amine which can be used in this step is preferably a water-soluble amine having two or more value and having at least one primary or secondary amino group, and examples thereof include 1-methylpiperazine, 4-aminopiperidine, diethylenetriamine, triaminoethylamine, 1-ethylpiperazine, N,N-dimethylethylenediamine, ethylenediamine and piperazine, preferably 1-methylpiperazine, 4-aminopiperidine and diethylenetriamine, and more preferably 1-methylpiperazine. The water-soluble amine in this step may be the same as or different from the water-soluble amine added in the step (ii) (scavenge reaction step).

The equivalent of a water-soluble amine to be added in this step (iii) is 5 to 30 equivalents, preferably 5 to 20 equivalents, and more preferably 10 to 20 equivalents with respect to the amount of an Fmoc group present in the system. When the amine addition amount is smaller than this range, scavenge (capture) of DBF generated by the deprotection of Fmoc reaction becomes insufficient, and impurities cannot be removed easily in the subsequent acidic aqueous solution washing step, while when larger than this range, the amount of an acid necessary for neutralization increases, and side reactions (decomposition, racemization) occur by the accompanying neutralization step, causing lowering of purity and a reduction of yield.

In this step, the deprotection of Fmoc reaction is conducted in the presence of a water-soluble amine, however, when the water-soluble amine present in the system has a function as a Fmoc-deprotecting reagent, another kind of Fmoc-deprotecting reagents may not be added to the system. In contrast, other Fmoc-deprotecting reagents may be added to the system for conducting the deprotection of Fmoc reaction efficiently. The water-soluble amine having a function as a Fmoc-deprotecting reagent includes, for example, the water-soluble amines exemplified above. In this step, it is preferable that a Fmoc-deprotecting reagent is added together with a water-soluble amine.

When a Fmoc-deprotecting reagent is added to the reaction system together with a water-soluble amine in this step, the water-soluble amine and the Fmoc-deprotecting reagent may be simultaneously added, alternatively, the water-soluble amine may be added to the system before adding the Fmoc-deprotecting reagent. "Simultaneously" herein referred to is meant to include adding the compounds before and after in the range considered to be simultaneous in the reaction in the art. When the water-soluble amine is added to the system before adding the Fmoc-deprotecting reagent, the interval time of addition can be appropriately controlled in view of the operation and other factors.

For removing an Fmoc group from the N terminal, removing methods generally used in peptide synthesis can be used in the present invention appropriately changing if necessary. The Fmoc-deprotecting reagent which can be used in the present invention includes, but not limited to, for example, 1,8-diazabicyclo[5.4.0]-7-undecene (DBU), 1,5-diazabicyclo[4.3.0]-5-nonene (DBN), 1,4-diazabicyclo[2.2.2]-octane (DABCO), triethylamine and tributylamine, preferably DBU.

DBF is generated at the time of the deprotection of Fmoc reaction, and the water-soluble amine added in this step can scavenge (capture) these impurities. DBF captured by a water-soluble amine can be easily removed in the subsequent acidic aqueous solution washing step.

6-4. Acidic Aqueous Solution Washing Step

By the neutralization step of (iv), excess bases and scavenged bodies present in the system can be converted into salts, to improve water solubility of them. The acid used for neutralization is not particularly limited as long as it can neutralize a base in the reaction solution, and examples thereof include aqueous solutions of hydrogen chloride, phosphoric acid, acetic acid, sulfuric acid and the like. For example, when hydrochloric acid is used, hydrochloric acid having a condensation of 1 N to 12 N, preferably 2 N to 12 N, more preferably 5 N to 12 N is added, though the condensation is not limited to this.

In the neutralization herein referred to, the reaction solution may have neutral pH, and pH may be 7.0 or less.

In the step (iv), an acidic aqueous solution is further added to the reaction solution neutralized with an acid, and the solution is washed, then, liquid-liquid separated, and the aqueous layer is discarded and the organic layer is recovered. By this, impurities soluble in the acidic aqueous solution can be removed.

The acidic aqueous solution to be used is not particularly limited, and examples thereof include hydrochloric acid water, dilute sulfuric acid solution, phosphoric acid aqueous solution and acetic acid aqueous solution, preferably hydrochloric acid water. pH of the acidic aqueous solution is 1 to 5, preferably 1 to 4, and more preferably 1 to 3.

The addition amount of the acidic aqueous solution used for washing is not particularly limited as long as it shows a washing effect, and it is 0.1 to 3-fold amount, preferably 0.5 to 2-fold amount, and more preferably 0.8 to 1.5-fold amount with respect to the reaction solution.

The steps of washing, liquid-liquid separation and aqueous layer discard are not limited in the number of times of execution, and may be carried out once or plural times. The number of times is appropriately selected depending on the type of the compound and the amount of impurities in the reaction system, and the object.

In the present invention, impurities can be removed by washing with an acidic aqueous solution of the step (iv). By the liquid-liquid separation operation of the acidic aqueous solution, it is possible to remove impurities such as, for example, $H_2N$-AAx-amine (scavenger) conjugate, condensing agent decomposed substance, pH regulating base, DBF-amine (scavenger) conjugate, amine (scavenger), Fmoc-deprotecting reagent and the like, and it is possible to obtain a carrier-protected peptide dissolved in the reaction solution in which impurities are reduced or removed.

The liquid-liquid, separation operation using a aqueous solution is simple, and contributes to reduction of the process time. Further, the solid-liquid separation operation is not necessary and use of a poor solvent for solidifying a carrier-protected peptide can be reduced.

In the last cycle of continuous peptide synthesis using the method of the present invention, after the deprotection of Fmoc step, neutralization with an acid is performed, then, a carrier-protected peptide is solidified (crystallized), and the carrier-protected peptide may be recovered using a solid-liquid separation operation, however, it is preferable to conduct washing with an acidic aqueous solution, from the standpoint of more complete removal of impurities.

The peptide synthesis method of the present invention includes a washing step with an acidic aqueous solution for reducing or removing impurities generated in the condensation step and the deprotection of Fmoc step, however, other washing steps may be added as long as recovering of the carrier-protected peptide in the condition dissolved in an organic solvent is not disturbed. Examples thereof include washing with a weakly basic aqueous solution and washing with saline. It is also possible to perform dehydration with a dehydrating agent such as anhydrous sodium sulfate and the like added, instead of washing with saline. The washing with a weakly basic aqueous solution includes washing with, for example, a sodium hydrogen carbonate aqueous solution, a sodium carbonate aqueous solution or a potassium carbonate aqueous solution having pH of 8 to 12 (preferably 8 to 10).

7. Carrier-Protected Peptide Crystallization/Separation Step

The carrier-protected peptide synthesized by the method of the present invention can be insolubilized (for example, crystallized or oiling out) and separated after neutralization with an acid of the step (iv), preferably after the liquid-liquid separation operation by an acidic aqueous solution of the step (iv). Further, the carrier-protected peptide synthesized by repeating the steps (i) to (iv) a necessary times using the method of the present invention can be insolubilized and separated after any steps after the step (i), without conducting the step (iii) when the deprotection of N terminal is not performed, after the step (i). The insolubilization can be carried out referring appropriately to known methods in the peptide synthesis field using a carrier having a property in which a dissolved condition and an insolubilized (crystallized or oiling out) condition changes reversibly depending on a change of the composition of a solvent in which the carrier-protected peptide is dissolved, and for example, it can be carried out by changing the composition of a solution in which the carrier-protected peptide is dissolved. The conditions for insolubilization can be selected appropriately depending on the type of the carrier to be used, and the type and length of the carrier-protected peptide synthesized. Examples thereof include, but not limited to, solvent composition changing means as described below.

The means for changing the composition of a solution is not particularly limited, providing it is a means capable of changing the composition of a solution in which a carrier-protected peptide is dissolved. The preferable means for changing the composition of a solution includes, for example, a means of adding a poor solvent to a solution in which a carrier-protected peptide is dissolved as it is, or after concentrating the solution, and crystallizing it. Here, condensation means that a part or all of the solvent is distilled off, for example, the solvent is distilled off under reduced pressure. Thereafter, the deposited crystal can be separated by, for example, filtration and centrifugal separation. By washing the separated crystal preferably with an organic solvent, impurities separated together with the crystal, can be completely removed from the carrier-protected peptide crystallized. Impurities are removed sufficiently from the carrier-protected peptide synthesized by the method of the present invention, however, impurities can be removed completely by conducting these operations.

The poor solvent in the present invention denotes a solvent in which a carrier-protected peptide is poorly soluble, that is, a solvent in which a carrier-protected peptide is difficult to dissolve or insoluble. The solvent in which a carrier-protected peptide is difficult to dissolve or insoluble may be a solvent, which is liquid at normal temperature, in which the solubility of a carrier-protected peptide is less than 1% by mass at 25° C., and is preferably acetonitrile, acetonitrile containing water at any ratio, methanol, methanol containing water at any ratio, or water.

In the last cycle of continuous peptide synthesis using the method of the present invention, it is possible to recover a carrier-protected peptide synthesized having higher purity, by conducting the crystallization and separation steps after neutralization with an acid of the step (iv), preferably after the liquid-liquid separation operation by an acidic aqueous solution of the step (iv).

8. Carrier Deprotection Step

The carrier deprotection is performed by detaching a carrier bonded directly or via a linker to a peptide in a carrier-protected peptide synthesized by the method of the present invention.

When the carrier is bonded directly to a peptide, carrier deprotection can be performed by removing (deprotection of) the carrier bonded to a carboxyl group, an amino group, an amide group or a hydroxyl group of the synthesized peptide.

The method of removing a carrier is not particularly limited, and known deprotection methods may be used, and it is preferably conducted by treating with an acid. For example, a deprotection method using TFA can be used, and more specifically, it is preferable to perform deprotection with 50 to 100% trifluoroacetic acid when Ka is used, with 1 to 100% trifluoroacetic acid when Kb is used, with 95 to 100% trifluoroacetic acid when Kc is used, with 1 to 100% trifluoroacetic acid when a carrier D is used, with 1 to 100% trifluoroacetic acid when a carrier E or a carrier F are used, with 95 to 100% trifluoroacetic acid when a carrier G is used, and with 1 to 100% trifluoroacetic acid when a carrier H is used.

In the method of the present invention, when a carrier is bonded to a peptide via a linker, the carrier deprotection may be conducted by (i) cutting a bond between the linker and the peptide, or (ii) cutting a bond between the linker and the carrier. In the latter case, the peptide is detached from the carrier in the condition carrying the linker, thus, a peptide in which the terminal or side chain is modified with the linker can be obtained.

The carrier deprotection in the case of (i) can be conducted, for example, by a deprotection method using TFA when a linker and a peptide are bonded by an ester bond or an amide bond, though the means is not limited to this.

In the carrier deprotection in the case of (ii), it is possible to use the deprotection method in the case of direct bond.

9. Synthesis of C Terminal-Modified Peptide

Amidation of the C terminal is modification often observed in peptides having biological activity, and examples thereof include calcitonin, gastrin, secretin, hormone releasing factors and the like. A peptide in which the C terminal is amidated can be efficiently synthesized by using a carrier having a reactive group containing an amino group, using the peptide synthesis method of the present invention.

For example, it is possible to obtain a peptide in which the C terminal is amidated, for example, modified with an amino group or an aminoalkyl group, by using a carrier-protected amino acid or peptide in which a carrier is bonded via a linker having as the reactive group an amino group binding to a carboxyl group to the carboxyl group terminal of any amino acid or peptide, or any of the following carriers (hereinafter, referred to as amide carrier in some cases) is bonded as a protective carrier directly to the terminal, in the method of the present invention.

The amide carrier includes carriers described above in which the reactive group carries an amino group or an alkylamino group.

Examples thereof include, but not limited to, the following carries.

9-1. Carrier Compound a, B or C

The carrier compounds A(Ka), B(Kb) or C(Kc) in which the reactive group is represented by the following formula are mentioned.

[Chemical Formula 119]

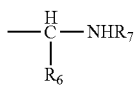

(wherein, $R_7$ represent a hydrogen atom, or an alkyl group having 1 to 6 carbon atoms, preferably 1 to 3 carbon atom, and $R_6$ represents a hydrogen atom.).

9-2. Carrier Compound D

The carrier compounds D(KS) in which the reactive group is represented by the following formula are mentioned.
—$CH_2NHRb$ (wherein, Rb represents a hydrogen atom, a linear or branched alkyl group having 1 to 6 carbon atoms, preferably 1 to 3 carbon atoms, or an aralkyl group.).

9-3. Carrier Compound G

The carrier compounds G(KJ3) in which the reactive group is represented by the following formula are mentioned.

Y is an —NHR group (R represents a hydrogen atom, an alkyl group or an aralkyl group).

9-4. Carrier Compound H

The carrier compounds H(KJ4) in which the reactive group is represented by the following formula are mentioned.

Y is an —NHR group (R represents a hydrogen atom, an alkyl group or an aralkyl group).

By the method of the present invention using any of the carriers, it is possible to obtain a peptide in which the C terminal is modified with an amino group or an alkylamino group. For example, it is possible to obtain a peptide in which proline at the C terminal is aminoethylated, thought the examples are not limited to this. Amidation of the C terminal is a modification often observed in peptides having biological activity, hence, the method of the present invention using an amide carrier as one embodiment of the present invention is useful for synthesizing such peptides.

The peptide obtained by using the peptide synthesis method of the present invention can be isolated and purified according to methods generally used in peptide synthesis. For example, the intended peptide can be isolated and purified by treating the reaction mixture by extraction and washing, crystallization, chromatography and the like.

Though the type of the peptide produced by the peptide synthesis method of the present invention is not particularly limited, it is preferable that the number of amino acid residues of the peptide is, for example, about several tens or less. The peptide obtained by the peptide synthesis method of the present invention can be utilized in various fields including, but not limited to, for example, fields of medicine, food, cosmetics, electronic materials, and the like, like known or unknown synthetic peptides and natural peptides.

EXAMPLES

The synthesis method will be described hereinafter using peptides having sequences described below as examples, but the present invention is not limited to them.
(Peptide A) H-Pyr-His-Trp-Ser-Tyr-dLeu-Leu-Arg-Pro-NHEt (SEQ ID NO: 2)
(Peptide B) H-dArg-Arg-Pro-Hyp-Gly-Thi-Ser-dTic-Oic-Arg-OH (SEQ ID NO: 1)

In the present specification and the following examples, abbreviations shown below were used.
AAs: one or more any amino acid residues
AAx: any amino acid residue
Boc: tert-butoxycarbonyl
COMU: (1-cyano-2-ethoxy-2-oxoethylideneaminooxy)dimethylamino-morpholino-carbenium hexafluorophosphate
CPME: cyclopentyl methyl ether
dArg: D-arginine
D-Arg: D-arginine
dLeu: D-leucine
dTic: D-1,2,3,4-tetrahydroisoquinoline-3-carboxylic acid
D-Tic: D-1,2,3,4-tetrahydroisoquinoline-3-carboxylic acid
DBU: 1,8-diazabicyclo[5.4.0]-7-undecene
DCM: dichloromethane
DIPCI: diisopropylcarbodiimide
DIPEA: N,N-diisopropylethylamine
DMAP: N,N-dimethyl-4-aminopyridine
DMF: N,N-dimethylformamide
DMT-MM: 4-(4,6-dimethoxy-1,3,5-triazin-2-yl)-4-methylmorpholinium chloride
DTT: dithiothreitol
Fmoc: 9-fluorenylmethyloxycarbonyl
HATU: O-(7-azabenzotriazol-1-yl)-1,1,3,3-tetramethyluronium hexafluorophosphate
HBTU: O-(benzotriazol-1-yl)-1,1,3,3-tetramethyluronium hexafluorophosphate
HOAt: 1-hydroxy-7-azabenzotriazol
HOBt: 1-hydroxybenzotriazol
HyQ: trans-4-hydroxy-L-proline
Ka: 3,4,5-trioctadecyloxybenzyl
Kb: 2,4-didocosyloxybenzyl
Kc: 3,5-didocosyloxybenzyl
Me: methyl
MTBE: methyl tert-butyl ether
NMP: N-methylpyrrolidone
Oic: L-octahydroindoline-2-carboxylic acid
Oxyma: ethyl cyanohydroxyimino acetate
Pbf: 2,2,4,6,7-pentamethyldihydrobenzofuran-5-sulfonyl
Pyr: pyroglutamic acid
Su: succinimidyl
tBu: tert-butyl
TFA: trifluoroacetic acid
TFE: 2,2,2-trifluoroethanol
THF: tetrahydrofuran
THP: tetrahydropyran Thi: β-(2-thienyl)-L-alanine
TIS: triisopropylsilane
Trt: triphenylmethyl The general synthesis method for Fmoc deprotection used in the present examples will be described below. The case in which Kb is used as the carrier compound is described as an example, but the carrier compound that can be used in the method of the present invention is not limited to Kb. Moreover, the addition amount of each reagent is merely an example, and the present invention is not limited to this.

(1) General Synthesis Method for Fmoc Deprotection

[Chemical Formula 120]

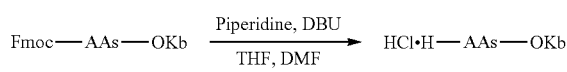

The starting materials were dissolved in a mixed solution of THF:DMF (9/1) so that the proportion was 18 v/w, and piperidine (1.5 equiv.) and DBU (1.0 equiv.) were added and the mixture was stirred at room temperature for 10 minutes. While cooling on ice, 6N hydrochloric acid (3.50 equiv.) was added and the solvent was distilled off under reduced pressure. To the residue was added acetonitrile and the deposited precipitate was filtrated, and further, suspending and washing with acetonitrile was conducted, and the resultant solid was dried under reduced pressure, to obtain a body of Fmoc deprotection.

The condensation deprotection method used in the method of the present invention will be described below. The case in which Kb is used as the carrier compound is described as an example, but the carrier compound that can be used in the method of the present invention is not limited to Kb. Moreover, the addition amount of each reagent is merely an example, and the present invention is not limited to this.

(2) 1 Pot Condensation Deprotection Method Using Amine Scavenger (Water-Soluble Amine)

[Chemical Formula 121]

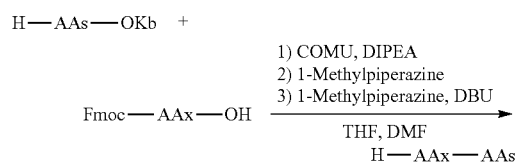

The starting materials were dissolved in a mixed solution of THF:DMF (9/1) so that the proportion was 18 v/w, and Fmoc-AAx-OH (1.30 equiv.), COMU (1.25 equiv.) and DIPEA (2.30 equiv.) were added and the mixture was stirred at room temperature for 30 minutes. 1-methylpiperazine (0.45 equiv.) was added as a water-soluble amine and the mixture was stirred at room temperature for 30 minutes. 1-methylpiperazine (20.0 equiv.) and DBU (7.0 equiv.) were added and the mixture was stirred at room temperature for 10 minutes. THF (0.8 v/w) and 0.1 N hydrochloric acid (18 v/w) were added to the reaction solution to which 6N hydrochloric acid (49.50 equiv.) had been added, and the solution was washed, separated, and the aqueous layer was discarded. Further, a 0.5 N sodium hydrogen carbonate aqueous solution (18 v/w) was added, and the solution was washed and separated, and the aqueous layer was discarded, to obtain an amino acid condensate in the form of a solution.

The method of deprotecting(detaching) the carrier from a peptide used in the method of the present invention will be described below. The case in which Kb is used as the carrier compound is described as an example, but the carrier compound that can be used in the method of the present invention is not limited to Kb. Moreover, the addition amount of each reagent is merely an example, and the present invention is not limited to this.

(3) Kb Protective Group General Deprotection Method

[Chemical Formula 122]

(wherein, R represents a protective group regularly used for protecting a hydrogen atom or an amino group)

The raw materials were dissolved in a mixed solution of DCM:TFE:TFA (90/9/1) so that the proportion was 19.75 v/w, and the solution was stirred at room temperature for 30 minutes. The precipitate was filtrated, and DIPEA was added to the filtrate so that its amount was 1.0 equiv. with respect to TFA, 0.01 N hydrochloric acid (18 v/w) was added, and the solution was washed, separated, and the aqueous layer was discarded. To the resultant organic layer was added diisopropyl ether and the solvent was distilled off under reduced pressure. To the residue was added diisopropyl ether and the deposited precipitate was suspended and washed, and the resultant solid was dried under reduced pressure, to obtain a Kb deprotection body.

The peptide synthesis using the method of the present invention will be described below.

The expression "v/w" in the following description of the specification indicates the amount of the solvent to be added, based on the starting materials, in a series of peptide synthesis reactions.

Example 1: Synthesis of H-Pyr-His-Trp-Ser-Tyr-dLeu-Leu-Arg-Pro-NHEt (SEQ ID NO: 2) Using Kb-OH Synthesis of Compound 1 (Fmoc-Arg(Pbf)-OKb)

[Chemical Formula 123]

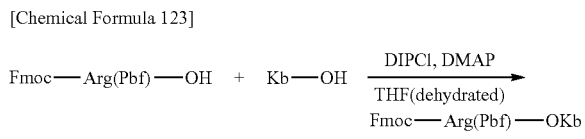

2,4-didocosyloxybenzyl alcohol (expressed as "Kb-OH") (10.0 g, 13.20 mmol) was dissolved in dehydrated THF (132 ml), and Fmoc-Arg(Pbf)-OH (12.85 g, 19.80 mmol, 1.50 equiv.), DIPCI (3.06 ml, 19.80 mmol, 1.5 equiv.) and DMAP (80.7 mg, 0.66 mmol, 0.05 equiv.) were added and the mixture was stirred at room temperature for 30 minutes. The reaction solution was distilled off under reduced pressure. To the residue was added methanol and the deposited precipitate was filtrated, suspending and washing with methanol was conducted, and further, suspending and washing with acetonitrile was conducted twice. The resultant solid was dried under reduced pressure, to obtain a compound 1 (18.33 g, quant).
Synthesis of Compound 2 (HCl·H-Arg(Pbf)-OKb)

[Chemical Formula 124]

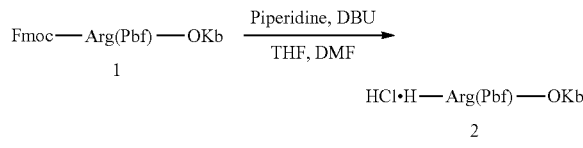

The compound 1 was subjected to the general synthesis method for Fmoc deprotection, to obtain a compound 2 (19.85 g, quant).
Synthesis of Compound 3 (H-His(Trt)-Trp(Boc)-Ser(tBu)-Tyr(tBu)-dLeu-Leu-Arg(Pbf)-OKb (SEQ ID NO: 3))

[Chemical Formula 125]

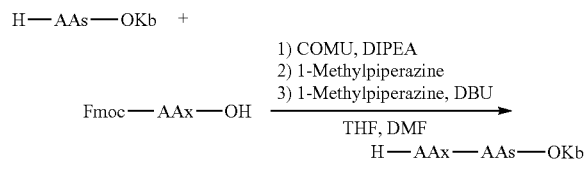

The following amino acids were introduced into the compound 2 by repeating the 1 pot condensation deprotection method using an amine scavenger (water-soluble amine), to obtain a compound 3 in the form of a solution.
1-st residue: Fmoc-Leu-OH
2-nd residue: Fmoc-dLeu-OH
3-rd residue: Fmoc-Tyr(tBu)-OH
4-th residue: Fmoc-Ser(tBu)-OH
5-th residue: Fmoc-Trp(Boc)-OH
6-th residue: Fmoc-His(Trt)-OH
Synthesis of Compound 4 (Pyr-His(Trt)-Trp(Boc)-Ser(tBu)-Tyr(tBu)-dLeu-Leu-Arg(Pbf)-OKb (SEQ ID NO: 4))

[Chemical Formula 126]

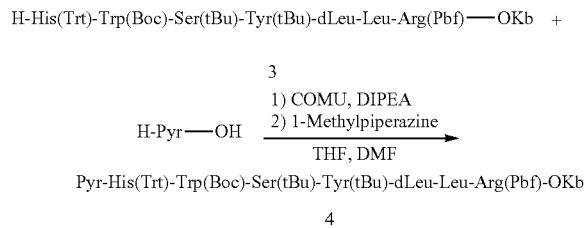

To the resultant compound 3 solution was added DMF so that its proportion was 1.8 v/w with respect to the theoretical yield. H-Pyr-OH (3.30 g, 25.55 mmol), COMU (7.0 g, 16.26 mmol, 1.25 equiv.) and DIPEA (5.10 ml, 29.28 mmol, 2.25 equiv.) were added. The resultant mixed solution was stirred at room temperature for 30 minutes. To the resultant reaction solution was added 1-methylpiperazine (0.45 equiv.) and the mixture was stirred at room temperature for 5 minutes. 0.01 N hydrochloric acid (18 v/w) was added, and the solution was washed, separated, and the aqueous layer was discarded.

The resultant organic layer was distilled under reduced pressure to remove the solvent. To the residue was added acetonitrile and the deposited precipitate was filtrated, and further, suspending and washing with acetonitrile was conducted, and the resultant solid was dried under reduced pressure, to obtain a compound 4 (28.78 g, 87.50%).
Synthesis of Compound 5 (Pyr-His(Trt)-Trp(Boc)-Ser(tBu)-Tyr(tBu)-dLeu-Leu-Arg(Pbf)-OH (SEQ ID NO: 5))

[Chemical Formula 127]

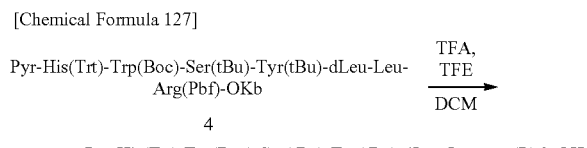

The compound 4 (20.0 g, 7.90 mmol) was subjected to the Kb protective group general deprotection method, to obtain a compound 5 (14.39 g, quant).
Synthesis of Compound 6 (Pyr-His(Trt)-Trp(Boc)-Ser(tBu)-Tyr(tBu)-dLeu-Leu-Arg(Pbf)-Pro-NHEt (SEQ ID NO: 6))

[Chemical Formula 128]

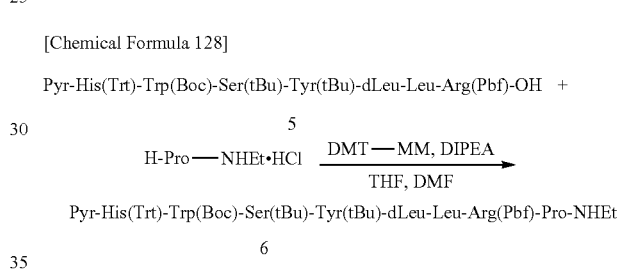

The compound 5 (6.20 g, 3.45 mmol) was dissolved in THF so that the proportion was 16.2 v/w, and H-Pro-NHEt.HCl (0.80 g, 4.5 mmol, 1.3 equiv.) dissolved in DMF at 1.8 v/w was added. DMT-MM-2H$_2$O (1.84 g, 6.05 mmol, 1.75 equiv.) and DIPEA (2.41 ml, 13.83 mmol, 4.0 equiv.) were added. The resultant mixed solution was stirred for 60 minutes while cooling on ice. To the resultant reaction solution was added cyclohexane (18 v/w), 0.01 N hydrochloric acid (18 v/w) was added, and the solution was washed, separated, and the aqueous layer was discarded. The resultant organic layer was distilled under reduced pressure to remove the solvent. To the residue was added diisopropyl ether and the deposited precipitate was filtrated, and further, suspending and washing with diisopropyl ether was conducted, and the resultant solid was dried under reduced pressure, to obtain a compound 6 (5.33 g, 80.51%).
Synthesis of Compound 7 (Pyr-His-Trp-Ser-Tyr-dLeu-Leu-Arg-Pro-NHEt (SEQ ID NO: 2))

[Chemical Formula 129]

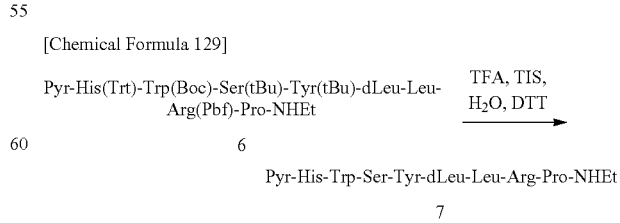

The compound 6 (5.33 g, 2.78 mmol) was dissolved in 92 ml of a mixed solution of TFA/TIS/water (90/1/9), DTT (3.70 g, 40 mg/ml) was added, and the mixture was stirred at room temperature for 3 hours. The reaction solution was filtrated through Celite, and the filtration residue was washed with methanol and filtrated, to the resultant filtrate was added toluene (same amount as the mixed solution), and the solvent was distilled off under reduced pressure. To the residue was added cold MTBE and the deposited precipitate was filtrated, and further, suspending and washing with MTBE and suspending and washing with hexane were conducted, and the resultant solid was dried under reduced pressure, to obtain a compound 7 (4.21 g, quant, HPLC purity: 76.28%).

Example 2. Synthesis of (Peptide B) H-dArg-Arg-Pro-Hyp-Gly-Thi-Ser-dTic-Oic-Arg-OH (SEQ ID NO: 1)

Synthesis of Compound 1 (Fmoc-Arg(Pbf)-OKb)

[Chemical Formula 130]

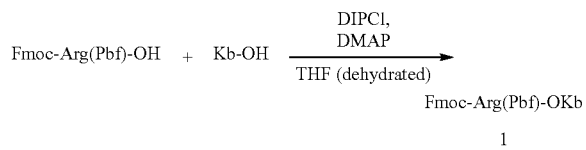

2,4-didocosyloxybenzyl alcohol (expressed as "Kb-OH") (1.5 g, 1.98 mmol) was dissolved in dehydrated THF (20 ml), and Fmoc-Arg(Pbf)-OH (1.93 g, 2.97 mmol, 1.5 equiv.), DIPCI (0.46 ml, 2.97 mmol, 1.5 equiv.) and DMAP (12 mg, 0.1 mmol, 0.05 equiv.) were added and the mixture was stirred at room temperature for 30 minutes. The reaction solution was distilled off under reduced pressure. To the residue was added methanol and the deposited precipitate was filtrated, suspending and washing with methanol was conducted, and further, suspending and washing with acetonitrile was conducted twice. The resultant solid was dried under reduced pressure, to obtain a compound 1 (2.75 g, quant.).

Synthesis of Compound 8 (H-Arg(Pbf)-OKb)

[Chemical Formula 131]

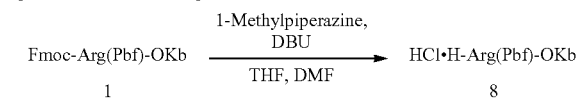

The compound 1 was subjected to the general synthesis method for Fmoc deprotection using 1-methylpiperazine instead of piperidine, and washed with hydrochloric acid water and with a sodium hydrogen carbonate aqueous solution, to obtain a compound 8 in the form of a solution.

Synthesis of Compound 9 (H-Arg(Pbf)-Pro-Hyp-Gly-Thi-Ser(tBu)-dTic-Oic-Arg(Pbf)-OKb (SEQ ID NO: 7))

[Chemical Formula 132]

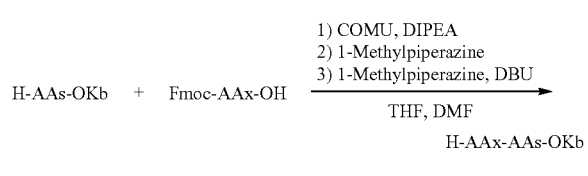

The following amino acids were sequentially condensed with the compound 8, and an amine scavenger was added each time, followed by the deprotection operation, and washing with hydrochloric acid water and with a sodium hydrogen carbonate aqueous solution were conducted. This 1 pot condensation deprotection method was repeated, to obtain a compound 9 in the form of a solution.

1-st residue: Fmoc-Oic-OH
2-nd residue: Fmoc-dTic-OH
3-rd residue: Fmoc-Ser(tBu)-OH
4-th residue: Fmoc-Thi-OH
5-th residue: Fmoc-Gly-OH
6-th residue: Fmoc-Hyp-OH
7-th residue: Fmoc-Pro-OH
8-th residue: Fmoc-Arg(Pbf)-OH Synthesis of Compound 10 (Boc-dArg(Pbf)-Arg(Pbf)-Pro-Hyp-Gly-Thi-Ser(tBu)-dTic-Oic-Arg(Pbf)-OKb (SEQ ID NO: 8))

[Chemical Formula 133]

H-Arg(Pbf)-Pro-Hyp-Gly-Thi-Ser(tBu)-dTic-Oic-Arg(Pbf)-Okb +

9

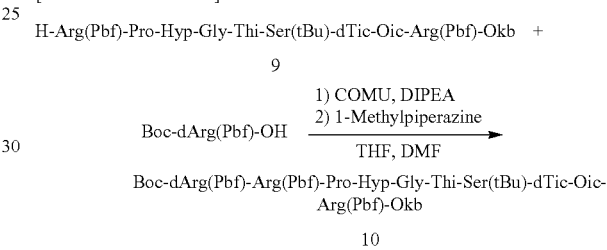

To the solution of the compound 9 were added Boc-dArg(Pbf)-OH (1.36 g, 2.57 mmol, 1.30 equiv.), COMU (1.06 g, 2.48 mmol, 1.25 equiv.) and DIPEA (0.78 ml, 4.45 mmol, 2.25 equiv.). The resultant mixed solution was stirred at room temperature for 30 minutes. To the resultant reaction solution was added 1-methylpiperazine (0.45 equiv.) and the mixture was stirred at room temperature for 5 minutes. Washing with 0.1N hydrochloric acid water (42 ml), subsequently with a 0.5 N sodium hydrogen carbonate aqueous solution (42 ml) and the liquid-liquid separation operations thereof were conducted, respectively, and the resultant organic layer was distilled under reduced pressure to remove the solvent. To the residue was added acetonitrile and the deposited precipitate was filtrated, and further, suspending and washing with acetonitrile was conducted, and the resultant solid was dried under reduced pressure, to obtain a compound 10 (4.77 g, 81.4%).

Synthesis of Compound 11 (4TFA.H-dArg-Arg-Pro-Hyp-Gly-Thi-Ser-dTic-Oic-Arg-OH (SEQ ID NO: 1))

The compound 10 (3.00 g, 1.01 mmol) was dissolved in 50 ml of a mixed solution of TFA/TIS/water (90/1/9), and the solution was stirred at room temperature for 4 hours. The reaction solution was filtrated through Celite, combined with the acetic acid washing solution and distilled under reduced pressure to remove the solvent. To the residue was added cold MTBE and the deposited precipitate was collected by filtration, then, suspending and washing with MTBE was conducted, subsequently, suspending and washing with hexane was conducted, and the resultant solid was dried under reduced pressure, to obtain a compound 11 (1.61 g, 90.4%, HPLC purity: 84.93%).

Example 3: Synthesis of H-Pyr-His-Trp-Ser-Tyr-dLeu-Leu-Arg-Pro-NHEt (SEQ ID NO: 1) Using Kb-NHEt Carrier Synthesis of Compound 12

[Chemical Formula 134]

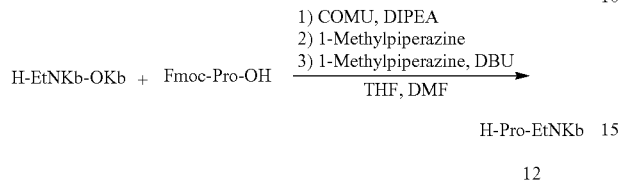

N-ethyl-2,4-didocosyloxybenzylamine (expressed as "EtNKb")(12.5 g, 15.23 mmol) was dissolved in THF/DMF (9/1) so that the proportion was 18 v/w, and Fmoc-Pro-OH/H$_2$O (7.04 g, 19.80 mmol, 1.30 equiv.), COMU (8.15 g, 19.04 mmol, 1.25 equiv.) and DIPEA (8.62 ml, 49.49 mmol, 3.30 equiv.) were added and the mixture was stirred at room temperature for 15 minutes. 1-methylpiperazine (0.45 equiv.) was added and the mixture was stirred at room temperature for 10 minutes. 1-methylpiperazine (20.0 equiv.) and DBU (7.0 equiv.) were added and the mixture was stirred at room temperature for 10 minutes. While cooling on ice, cyclohexane (4.5 v/w) and 0.1 N hydrochloric acid (18 v/w) were added to the reaction solution to which 6N hydrochloric acid (50.70 equiv.) had been added, and the solution was washed, separated, and the aqueous layer was discarded. Further, a 0.5 N sodium hydrogen carbonate aqueous solution (18 v/w) was added, the solution was washed and separated, and the aqueous layer was discarded, to obtain a compound 12 in the form of a solution.

Synthesis of Compound 13 (H-His(Trt)-Trp(Boc)-Ser(tBu)-Tyr(tBu)-dLeu-Leu-Arg(Pbf)-Pro-EtNKb (SEQ ID NO: 9))

[Chemical Formula 135]

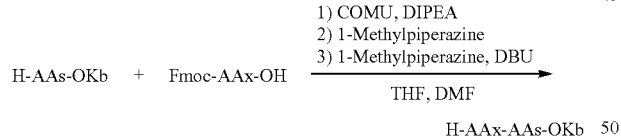

The following amino acids were introduced into the compound 12 solution by repeating the 1 pot condensation deprotection method using an amine scavenger (water-soluble amine), to obtain a compound 13 in the form of a solution.

1-st residue: Fmoc-Arg(Pbf)-OH
2-nd residue: Fmoc-Leu-OH
3-rd residue: Fmoc-dLeu-OH
4-th residue: Fmoc-Tyr(tBu)-OH
5-th residue: Fmoc-Ser(tBu)-OH
6-th residue: Fmoc-Trp(Boc)-OH
7-th residue: Fmoc-His(Trt)-OH Synthesis of Compound 14 (Pyr-His(Trt)-Trp(Boc)-Ser(tBu)-Tyr(tBu)-dLeu-Leu-Arg(Pbf)-Pro-EtNKb (SEQ ID NO: 10))

[Chemical Formula 136]

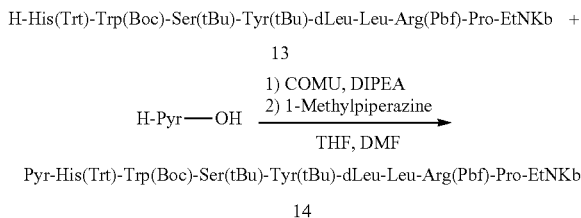

To the resultant compound 13 solution were added H-Pyr-OH (2.95 g, 22.84 mmol, 1.50 equiv.), COMU (9.46 g, 22.08 mmol, 1.45 equiv.) and DIPEA (6.50 ml, 37.31 mmol, 2.50 equiv.). The resultant mixed solution was stirred at room temperature for 15 minutes. To the resultant reaction solution was added 1-methylpiperazine (0.65 equiv.) and the mixture was stirred at room temperature for 10 minutes. While cooling on ice, 6N hydrochloric acid (3.10 equiv.) was added to neutralize it, then, 0.1 N hydrochloric acid (18 v/w) was added, and the solution was washed, separated, and the aqueous layer was discarded. Further, a 0.5 N sodium hydrogen carbonate aqueous solution (18 v/w) was added, and the solution was washed, separated, and the aqueous layer was discarded. The resultant organic layer was distilled under reduced pressure to remove the solvent. To the residue was added cold acetonitrile and the deposited precipitate was filtrated, and further, suspending and washing with acetonitrile was conducted, and the resultant solid was dried under reduced pressure, to obtain a compound 14 (36.93 g, 90.83%).

Synthesis of Compound 7 (Pyr-His-Trp-Ser-Tyr-dLeu-Leu-Arg-Pro-NHEt (SEQ ID NO: 2))

[Chemical Formula 137]

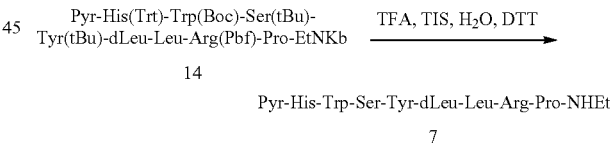

The compound 14 (5.00 g) was dissolved in 93.6 ml of a mixed solution of TFA/TIS/water (90/1/9), DTT (1.87 g, 20 mg/ml) was added, and the mixture was stirred at room temperature for 3 hours. The reaction solution was filtrated through Celite, the filtration residue was washed with methanol and filtrated, and to the resultant filtrate concentrated residue was added cold MTBE and the deposited precipitate was filtrated, and further, suspending and washing with MTBE was conducted twice and suspending and washing with hexane was conducted, and the resultant solid was dried under reduced pressure, to obtain a compound 7 (2.45 g, 93.0%, HPLC purity: 95.18%).

Comparative Example 1: The following peptide was synthesized using a solid-liquid separation method in which the carrier is solidified after the Fmoc deprotection reaction.

Synthesis of (Peptide B) H-dArg-Arg-Pro-Hyp-Gly-Thi-Ser-dTic-Oic-Arg-OH (SEQ ID NO: 1)
Synthesis of Compound 101 (Fmoc-Arg(Pbf)-OKa)

A compound 101 was synthesized according to the description of International Patent Publication WO2007/034812.

[Chemical Formula 138]

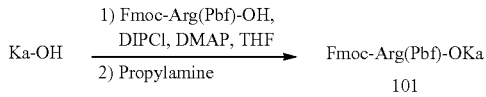

A compound 101 (83.5 g) was obtained using Ka-OH (50.0 g (54.7 mmol, 1.0 eq.)) and Fmoc-Arg(Pbf)-OH (53.3 g (82.1 mmol, 1.5 eq.)). Yield: 98.8%
Synthesis of Compound 102 (HCl.H-Arg(Pbf)-OKa)

A compound 102 was synthesized from the compound 101 according to the description of International Patent Publication WO2007/034812.

[Chemical Formula 139]

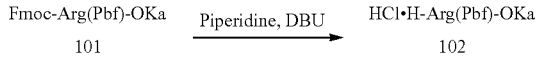

A compound 102 (73.0 g) was obtained from Fmoc-Arg(Pbf)-OKa (compound 101) (81.6 g). Yield: quant.
Synthesis of Compound 103 (HCl.H-Oic-Arg(Pbf)-OKa)

[Chemical Formula 140]

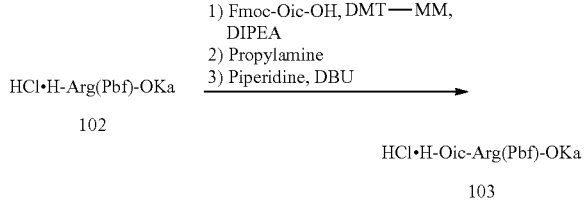

Into a previously washed and dried 3 L four-necked flask, THF/DMF (9/1) (13 v/w) and HCl.H-Arg(Pbf)-OKa (compound 102) (71.0 g (52.3 mmol, 1.0 eq.)) and Fmoc-Oic-OH (1.50 eq.) were added and dissolved. To the resultant solution was added DMT-MM (1.45 eq.) at an inner temperature of 30° C. or lower. Further, DIPEA (5.00 eq.) was added and the mixture was stirred and reacted for 30 minutes. After conforming the completion of the reaction by TLC, to the resultant reaction solution was added propylamine (1.80 eq.), and the mixture was stirred for 30 minutes. To the resultant reaction solution were added piperidine (1.5 eq.) and DBU (7.0 eq.), and the mixture was stirred at room temperature for 10 minutes, then, disappearance of the raw materials was confirmed by TLC. The resultant reaction solution was cooled at 0 to 10° C., and 6 N HCl (15.3 eq.) was added. To the resultant solution was added THF (5.0 v/w). Further, 0.01 N—HCl (10.0 v/w) and ethyl acetate (5.0 v/w) were added, and the mixture was stirred for 10 minutes, allowed to stand still for 5 minutes, and the lower layer was discharged. To the resultant upper layer was added a water:saturated saline=9:1 solution (10.0 v/w) and the mixture was stirred for 10 minutes, and stirring was stopped, and the mixture was allowed to stand still for 5 minutes and the lower layer was discharged. This operation was repeated once more. To the resultant organic layer was added magnesium sulfate (1.0 w/w), and the mixture was stirred for 30 minutes. The resultant suspension was filtrated, and the residue was washed with THF (5.0 v/w) twice. To the resultant filtrate was added DMF (1.1 v/w), and the mixture was concentrated at 40° C. under reduced pressure until the proportion of the distilled solution was 16.1 v/w. Into a previously washed and dried 2 L vessel, the resultant residue was transferred using THF (2.00 v/w). To the resultant solution was added acetonitrile (10.9 v/w), and the mixture was stirred for 30 minutes. The resultant suspension was filtrated, and the cake was washed with acetonitrile (3.00 v/w) twice. Into a previously washed reaction vessel, the resultant cake was transferred, acetonitrile (10.9 v/w) was added, and the mixture was stirred for 30 minutes. The resultant suspension was filtrated, and the resultant cake was washed with acetonitrile (3.00 v/w) twice. The resultant cake was dried at 40° C. under reduced pressure for 13 hours, to obtain a compound 103 (75.8 g). Yield: 96.1%
Synthesis of Compound 104 (HCl.H-D-Tic-Oic-Arg(Pbf)-OKa (SEQ ID NO: 11))

[Chemical Formula 141]

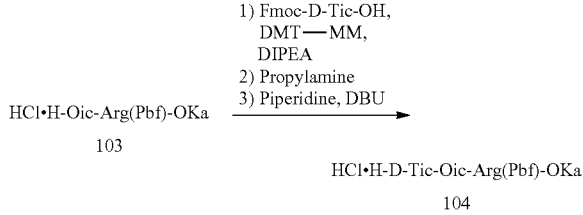

A compound 104 (78.8 g) was obtained in the same manner as in Synthesis of compound 103 using HCl.H-Oic-Arg(Pbf)-OKa (compound 103) (73.5 g (48.7 mmol, 1.0 eq.)) and Fmoc-D-Tic-OH (29.2 g (78.4 mmol, 1.50 eq.)). Yield: 96.9%.
Synthesis of Compound 105 (HCl.H-Ser(tBu)-D-Tic-Oic-Arg(Pbf)-OKa (SEQ ID NO: 12))

[Chemical Formula 142]

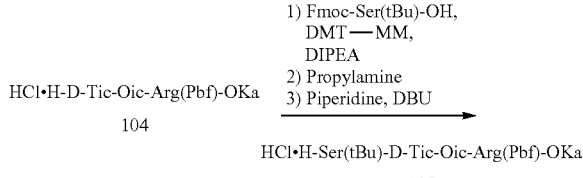

A compound 105 (83.1 g) was obtained in the same manner as in Synthesis of compound 103 using HCl.H-D-Tic-Oic-Arg(Pbf)-OKa (compound 104) (78.5 g (47.0 mmol, 1.0 eq.)) and Fmoc-Ser(tBu)-OH (27.1 g (70.6 mmol, 1.50 eq.)). Yield: 97.5%

Synthesis of compound 106 (HCl.H-Thi-Ser(tBu)-D-Tic-Oic-Arg(Pbf)-OKa (SEQ ID NO: 13))

[Chemical Formula 143]

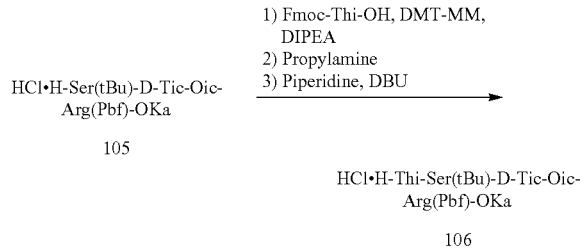

A compound 106 (87.7 g) was obtained in the same manner as in Synthesis of compound 103 using HCl.H-Ser(tBu)-D-Tic-Oic-Arg(Pbf)-OKa (compound 105) (82.5 g (45.5 mmol, 1.0 eq.)) and Fmoc-Thi-OH (26.9 g (68.3 mmol, 1.50 eq.)). Yield: 98.1%

Synthesis of Compound 107 (HCl.H-Gly-Thi-Ser(tBu)-D-Tic-Oic-Arg(Pbf)-OKa (SEQ ID NO: 14))

[Chemical Formula 144]

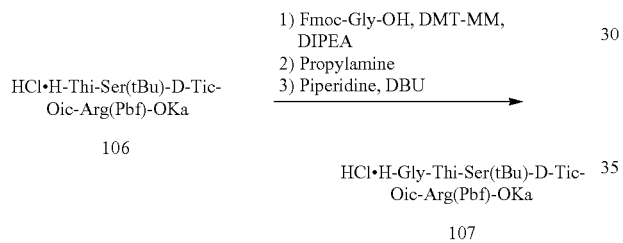

A compound 107 (87.3 g) was obtained in the same manner as in Synthesis of compound 103 using HCl.H-Thi-Ser(tBu)-D-Tic-Oic-Arg(Pbf)-OKa (compound 106) (87.5 g (44.6 mmol, 1.0 eq.)) and Fmoc-Gly-OH (26.9 g (66.9 mmol, 1.50 eq.)). Yield: 96.9%

Synthesis of Compound 108 (HCl.H-Hyp-Gly-Thi-Ser(tBu)-D-Tic-Oic-Arg(Pbf)-OKa (SEQ ID NO: 15))

[Chemical Formula 145]

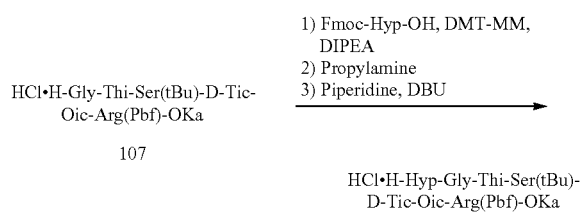

A compound 108 (89.4 g) was obtained in the same manner as in Synthesis of compound 103 using HCl.H-Gly-Thi-Ser(tBu)-D-Tic-Oic-Arg(Pbf)-OKa (compound 107) (87.0 g (43.0 mmol, 1.0 eq.)) and Fmoc-Hyp-OH (22.8 g (64.5 mmol, 1.50 eq.)). Yield: 97.2%

Synthesis of Compound 109 (HCl.H-Pro-Hyp-Gly-Thi-Ser(tBu)-D-Tic-Oic-Arg(Pbf)-OKa (SEQ ID NO: 16))

[Chemical Formula 146]

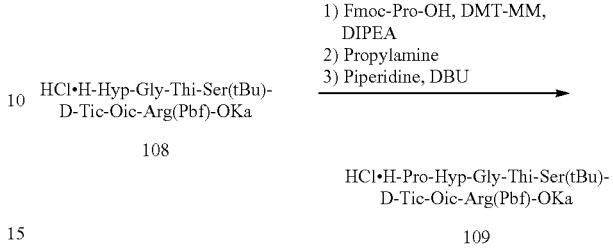

A compound 109 (89.9 g) was obtained in the same manner as in Synthesis of compound 103 using HCl.H-Hyp-Gly-Thi-Ser(tBu)-D-Tic-Oic-Arg(Pbf)-OKa (compound 108) (89.0 g (41.7 mmol, 1.0 eq.)) and Fmoc-Pro-OH (21.1 g (62.5 mmol, 1.50 eq.)). Yield: 96.6%

Synthesis of Compound 110 (HCl.H-Arg(Pbf)-Pro-Hyp-Gly-Thi-Ser(tBu)-D-Tic-Oic-Arg(Pbf)-OKa (SEQ ID NO: 17))

[Chemical Formula 147]

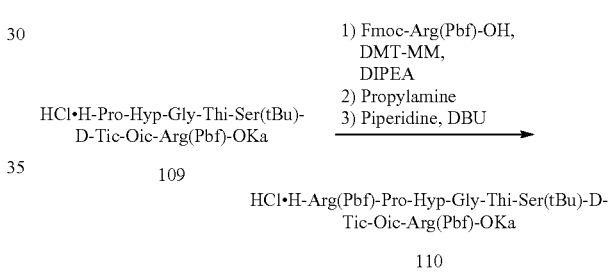

A compound 110 (101.9 g) was obtained in the same manner as in Synthesis of compound 103 using HCl.H-Pro-Hyp-Gly-Thi-Ser(tBu)-D-Tic-Oic-Arg(Pbf)-OKa (compound 109) (89.5 g (40.1 mmol, 1.0 eq.)) and Fmoc-Arg(Pbf)-OH (39.0 g (60.1 mmol, 1.50 eq.)). Yield: 96.3%

Synthesis of Compound 111 (HCl.H-D-Arg(Pbf)-Arg(Pbf)-Pro-Hyp-Gly-Thi-Ser(tBu)-D-Tic-Oic-Arg(Pbf)-OKa (SEQ ID NO: 18))

[Chemical Formula 148]

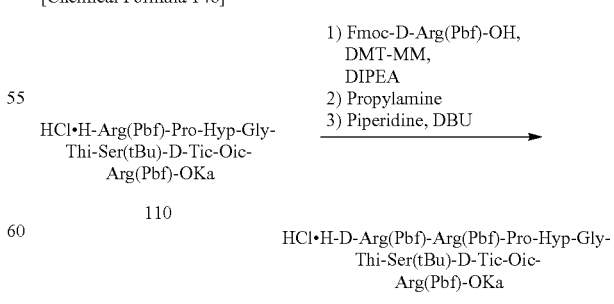

A compound 111 (112.1 g) was obtained in the same manner as in Synthesis of compound 103 using HCl.H-Arg (Pbf)-Pro-Hyp-Gly-Thi-Ser(tBu)-D-Tic-Oic-Arg(Pbf)-OKa (compound 110) (101 g (38.4 mmol, 1.0 eq.)) and Fmoc-D-Arg(Pbf)-OH (37.4 g (57.6 mmol, 1.50 eq.)). Yield: 96.0%

Synthesis of Compound 11 (4TFA.H-D-Arg-Arg-Pro-Hyp-Gly-Thi-Ser-D-Tic-Oic-Arg-OH (SEQ ID NO: 1))

[Chemical Formula 149]

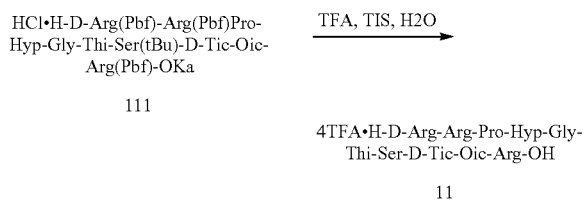

Into a previously washed and dried 2 L four-necked flask, a TFA/TIS/H$_2$O=90/1/9 mixed solution (550 ml (10 v/w)) was charged and HCl.H-D-Arg(Pbf)-Arg(Pbf)-Pro-Hyp-Gly-Thi-Ser(tBu)-D-Tic-Oic-Arg(Pbf)-OKa (compound 111) (55 g (18.0 mmol, 1.0 eq.)) was added, and the mixture was washed thoroughly with a TFA/TIS/H$_2$O=90/1/9 mixed solution (50 ml (0.91 v/w)). The resultant solution was stirred at an inner temperature of 23.5 to 31.5° C. for 4 hours, and reacted. To the resultant reaction solution was added Hyflo Super-Cel (55 g (1.00 w/w)), and the mixture was stirred and suspended. Hyflo Super-Cel (55.0 g (1.00 w/w)) was pre-coated on a 150φ Kiriyama funnel, and the reaction solution was filtered though this. The filtration residue was washed with acetic acid (193 ml (3.5 v/w)). Further, the filtration residue was washed with 110 ml of acetic acid twice, and concentrated. The filtrate and the washing solution were combined, and further, washed thoroughly with acetic acid (13.8 ml (0.25 v/w)), and cooled down to 0° C. To the resultant solution, MTBE (3440 ml (62.5 v/w)) cooled to −20° C. was added over a period of 10 minutes, and the mixture was stirred for 35 minutes. The resultant suspension was filtrated, and the resultant cake was washed with MTBE (110 ml (2.0 v/w)). The resultant cake was transferred to a beaker, MTBE (1380 ml (25.0 v/w)) was added, and the mixture was stirred for 10 minutes. The resultant suspension was filtrated, and the resultant cake was washed with MTBE (110 ml (2.0 v/w)). The resultant cake was transferred to a beaker, n-hexane (1030 ml (18.8 v/w)) was added, and the mixture was stirred for 5 minutes. The resultant suspension was filtrated, and the resultant cake was washed with n-hexane (55 ml (2.0 v/w)). The resultant cake was dried at room temperature under reduced pressure for 15 hours, to obtain 4TFA.H-D-Arg-Arg-Pro-Hyp-Gly-Thi-Ser-D-Tic-Oic-Arg-OH (SEQ ID NO: 2) (23.2 g). Yield: 73.2%. Purity: (HPLC) 85.9%.

In comparative examples, a process of solidifying the carrier-protected peptide and filtrating and drying is necessary, thus, the operation is complicated and requires a large amount of organic solvent, and further, the process time becomes long due to the drying step.

Synthesis of Compound 16 (H-Leu-Arg-Pro-NHEt (SEQ ID NO: 19)) Using Kb-NHEt Carrier with Various Bases Example 4: Synthesis of Compound 15 (H-Leu-Arg (Pbf)-Pro-NHEt (SEQ ID NO: 20)) with 1-methylpiperazine

[Chemical Formula 150]

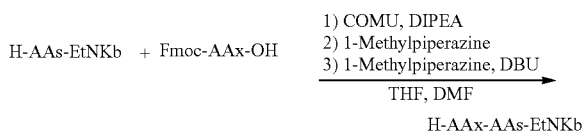

The following amino acids were introduced, in the same manner as in Example 3 using HCl.H-EtNKb (1.76 g, 2.00 mmol), to obtain a compound 15 in the form of a solution.
1-st residue: Fmoc-Pro-OH
2-nd residue: Fmoc-Arg(Pbf)-OH
3-rd residue: Fmoc-Leu-OH To the resultant solution was added a 0.5 N sodium hydrogen carbonate aqueous solution (18 v/w), and the solution was washed, separated, and the aqueous layer was discarded. Then, 0.01 N hydrochloric acid water (8 v/w) was added, and further, pH was controlled to 3 with 6N hydrochloric acid water, then, the solution was separated, and the aqueous layer was discarded. The resultant organic layer was distilled under reduced pressure to remove the solvent. To the residue was added cold acetonitrile and the deposited precipitate was filtrated, and further, suspending and washing with acetonitrile was conducted, and the resultant solid was dried under reduced pressure, to obtain a compound 15 (2.95 g, quant, HPLC purity: 96.29%).

Example 5: Synthesis of Compound 16 (H-Leu-Arg-Pro-NHEt (SEQ ID NO: 19))

[Chemical Formula 151]

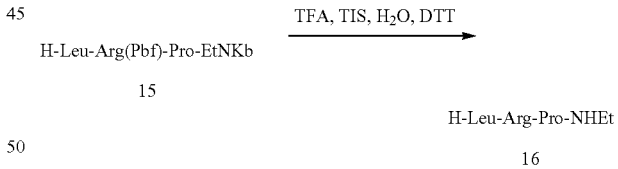

The compound 15 (2.97 g) was dissolved in 75.6 ml of a mixed solution of TFA/TIS/water (90/1/9), DTT (1.51 g, 20 mg/ml) was added, and the mixture was stirred at room temperature for 3 hours. The reaction solution was filtrated through Celite, the filtration residue was washed with methanol and filtrated, and to the resultant filtrate concentrated residue was added cold MTBE. The deposited precipitate was filtrated, and further, suspending and washing with MTBE was performed twice, and the resultant solid was dissolved in water, and undissolved materials were separated by filtration. Further, the undissolved materials were washed with water and separated by filtration. The resultant filtrates were combined and dried under reduced pressure, to obtain a compound 16 (1.02 g, 93.5%, HPLC purity: 93.89%).

Example 6: Synthesis of Compound 16 with Diethylenetriamine

[Chemical Formula 152]

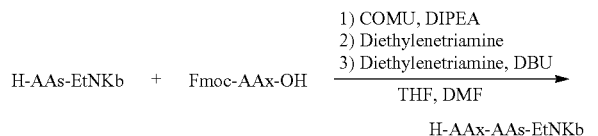

A compound 15 (1.85 g, 63.6%, HPLC purity: 95.54%) was obtained from HCl.H-EtNKb (1.76 g, 2.00 mmol) in the same manner as in Example 4 (however, the base used was changed from 1-methylpiperazine to diethylenetriamine). Further, a compound 16 (1.05 g, quant, HPLC purity: 86.60%) was obtained in the same manner as in Example 5 using the resultant compound 15 (2.24 g).

Example 7: Synthesis of Compound 16 with N,N-dimethylethylenediamine

[Chemical Formula 153]

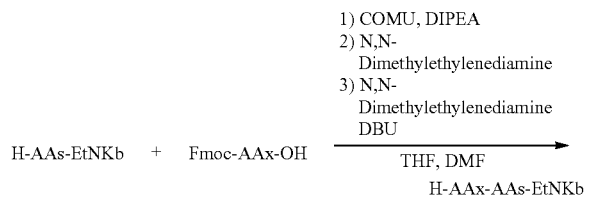

A compound 15 (2.55 g, 87.6%, HPLC purity: 95.38%) was obtained from HCl.H-EtNKb (1.76 g, 2.00 mmol) in the same manner as in Example 4 (however, the base used was changed from 1-methylpiperazine to N,N-dimethylethylenediamine). Further, a compound 16 (1.21 g, quant, HPLC purity: 81.22%) was obtained in the same manner as in Example 5 using the resultant compound 15 (2.39 g).

Example 8: Synthesis of Compound 16 with 4-aminopiperidine

[Chemical Formula 154]

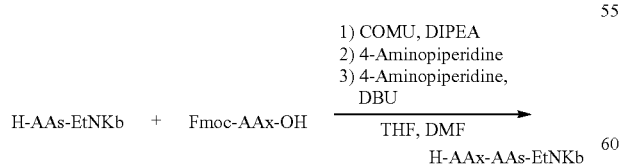

A compound 15 (2.72 g, 93.5%, HPLC purity: 96.63%) was obtained from HCl.H-EtNKb (1.76 g, 2.00 mmol) in the same manner as in Example 4 (however, the base used was changed from 1-methylpiperazine to 4-aminopiperidine). Further, a compound 16 (0.96 g, 97.0%, HPLC purity: 92.75%) was obtained in the same manner as in Example 5 using the resultant compound 15 (2.63 g).

Example 9: Synthesis of Compound 16 with Ethylenediamine

[Chemical Formula 155]

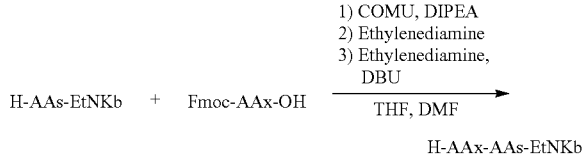

A compound 15 (2.43 g, 83.5%, HPLC purity: 94.85%) was obtained from HCl.H-EtNKb (1.76 g, 2.00 mmol) in the same manner as in Example 4 (however, the base used was changed from 1-methylpiperazine to ethylenediamine). Further, a compound 16 (0.93 g, quant, HPLC purity: 89.93%) was obtained in the same manner as in Example 5 using the resultant compound 15 (2.22 g).

Differences between base types are summarized in the table below.

TABLE 1

| Type of base | yield of compound 15 | purity of compound 15 | purity of compound 16 |
| --- | --- | --- | --- |
| 1-Methylpiperazine | quant | 96.29% | 93.89% |
| Diethylenetriamine | 63.6% | 95.54% | 86.60% |
| N,N-Dimethylethylenediamine | 87.60% | 95.38% | 81.22% |
| 4-Aminopiperidine | 93.50% | 96.63% | 92.75% |

Synthesis of Compound 23 (Pyr-His-Trp-Ser-Tyr-dLeu-Leu-Arg-OH (SEQ ID NO: 21)) Using 2,4-di(11'-triisopropylsilyloxyundecyloxy)benzyl Alcohol

Example 10: Synthesis of Compound 17 (1-bromo-11-triisopropylsilyloxyundecane)

[Chemical Formula 156]

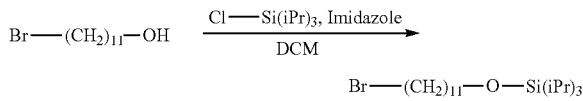

17

A compound 17 (4.07 g, 9.99 mmol, 99.9%) was obtained in the same manner as in Japanese Patent No. 6116782, Example (1-a) using 1-bromoundecanol (2.51 g, 10 mmol).

Example 11: Synthesis of Compound 18 (2,4-di(11'-triisopropylsilyloxy)benzaldehyde

[Chemical Formula 157]

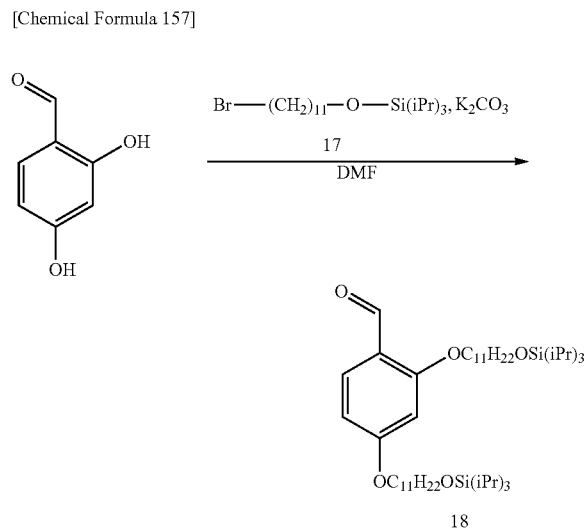

A compound 18 (1.78 g, 2.25 mmol, 91.5%) was obtained in the same manner as in Japanese Patent No. 6116782, Example (1-b) using 2,4-dihydroxybenzaldehyde (0.34 g, 2.46 mmol).

Example 12: Synthesis of Compound 19 (2,4-di(11'-triisopropylsilyloxyundecyloxy)benzyl Alcohol ("2,4-di(11'-triisopropylsilyloxyundecyloxy)benzyl Group" is Hereinafter Referred to as "KS1" in Some Cases)

[Chemical Formula 158]

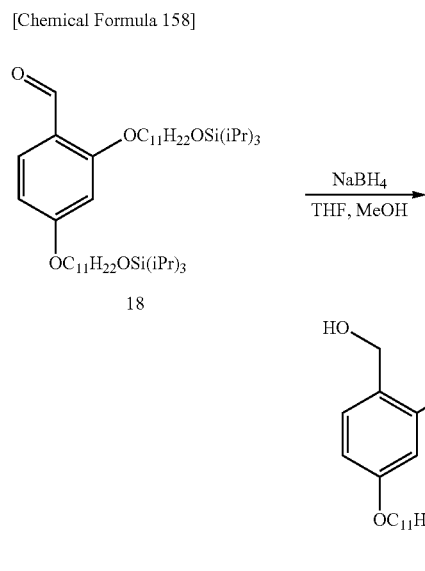

A compound 19 (1.65 g, 2.08 mmol, 93.7%) was obtained in the same manner as in Japanese Patent No. 6116782, Example (1-c) using 2,4-di(11'-triisopropylsilyloxyundecyloxybenzaldehyde (1.76 g, 2.22 mmol).

Example 13: Synthesis of Compound 20 (H-Arg(Pbf)—O—KS1)

[Chemical Formula 159]

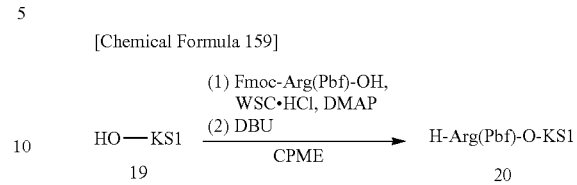

A compound 20 solution was obtained in the same manner as in Japanese Patent No. 6116782, Example (1-c) (however, Fmoc-Arg(Pbf)-OH was used instead of Fmoc-Gly-OH) using 2,4-di(11'-triisopropylsilyloxyundecyloxybenzyl alcohol (1.00 g, 1.26 mmol). The resultant solution was concentrated under reduced pressure, and thoroughly dried, to obtain a compound 20 (1.515 g, 1.26 mmol, quant).

Example 14: Synthesis of Compound 21 (H-His(Trt)-Trp(Boc)-Ser(tBu)-Tyr(tBu)-dLeu-Leu-Arg(Pbf)—O—KS1 (SEQ ID NO: 22))

[Chemical Formula 160]

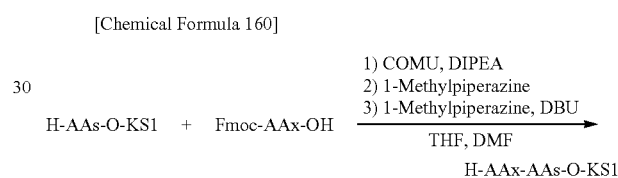

The following amino acids were introduced into the compound 20 obtained in Example 13 by repeating the 1 pot condensation deprotection method using an amine scavenger (water-soluble amine), to obtain a compound 21 in the form of a solution.
1-st residue: Fmoc-Leu-OH
2-nd residue: Fmoc-dLeu-OH
3-rd residue: Fmoc-Tyr(tBu)-OH
4-th residue: Fmoc-Ser(tBu)-OH
5-th residue: Fmoc-Trp(Boc)-OH
6-th residue: Fmoc-His(Trt)-OH

Example 15: Synthesis of Compound 22 (Pyr-His(Trt)-Trp(Boc)-Ser(tBu)-Tyr(tBu)-dLeu-Leu-Arg(Pbf)—O—KS1 (SEQ ID NO: 23))

[Chemical Formula 161]

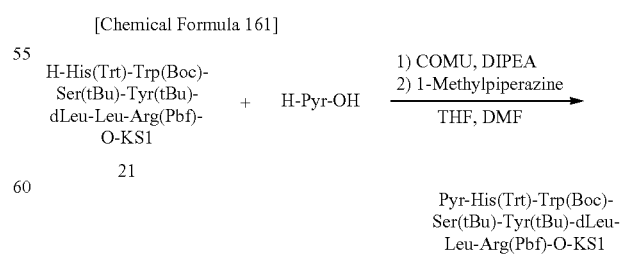

To the resultant compound 21 solution was added DMF so that its proportion was 1.8 v/w with respect to the theoretical yield. H-Pyr-OH (0.213 g, 1.64 mmol), COMU (0.675 g, 1.58 mmol) and DIPEA (0.505 ml, 2.90 mmol) were added. The resultant mixed solution was stirred at room temperature for 30 minutes. To the resultant reaction solution was added 1-methylpiperazine (0.45 equiv.) and the mixture was stirred at room temperature for 5 minutes. 6 N hydrochloric acid was added to neutralize it, and further, 0.1 N hydrochloric acid was added so that its proportion was 18 v/w with respect to the theoretical yield, and the solution was washed, separated, and the aqueous layer was discarded. To the resultant organic layer were added 0.1 N hydrochloric acid and the same amount of a 0.5 N sodium bicarbonate aqueous solution, and the solution was washed, separated, and the aqueous layer was discarded. The resultant organic layer was distilled under reduced pressure to remove the solvent, thereby obtaining a compound 22 (1.09 g, 33.7%).

Example 16: Synthesis of Compound 23 (Pyr-His-Trp-Ser-Tyr-dLeu-Leu-Arg-OH) (SEQ ID NO: 21)

[Chemical Formula 162]

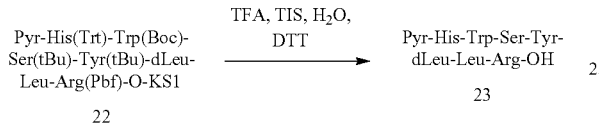

The compound 22 (1.00 g, 2.78 mmol) was dissolved in 92 ml of a mixed solution of TFA/TIS/water (90/1/9), DTT (3.70 g, 40 mg/ml) was added, and the mixture was stirred at room temperature for 3 hours. The reaction solution was filtrated through Celite, and the filtration residue was washed with methanol and filtrated. To the resultant filtrate was added toluene (same amount as the mixed solution), and the solvent was distilled off under reduced pressure. To the residue was added cold MTBE and the deposited precipitate was filtrated, and further, suspending and washing with MTBE was conducted, and suspending and washing with hexane was conducted, and the resultant solid was dried under reduced pressure, to obtain a compound 23 (4.21 g, quant, HPLC purity: 76.28%).

Synthesis of Compound 23 (Pyr-His-Trp-Ser-Tyr-dLeu-Leu-Arg-OH) (SEQ ID NO: 21) Using 2,7-didocosyloxy-9-(3-fluorophenyl)-9-bromofluorene Example 17: Synthesis of Compound 24 (2,7-didocosyloxy-9-fluorenone)

[Chemical Formula 163]

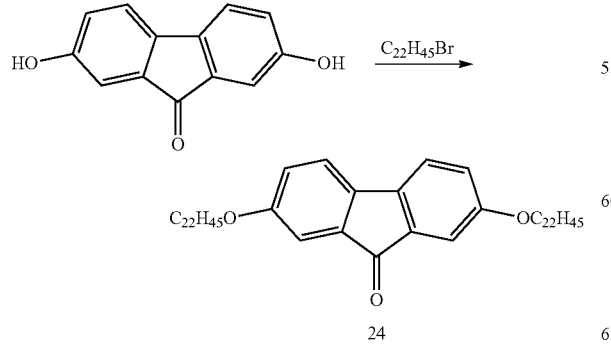

A compound 24 (4.25 g, docosyl bromide mixture) was obtained in the same manner as in Japanese Patent No. 6092513, Example 2, 2-1 using 2,7-dihydroxy-9-fluorenone (1.00 g, 4.71 mmol).

Example 18: Synthesis of Compound 25 (2,7-didocosyloxy-9-(3-fluorophenyl)-9-fluorenol)

[Chemical Formula 164]

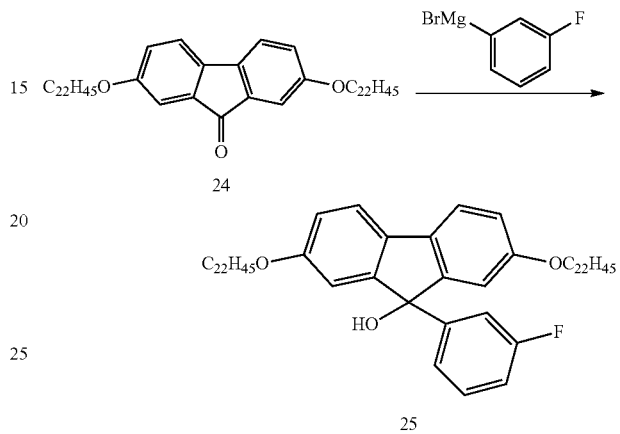

A compound 25 (1.55 g, 1.68 mmol, 83.8%) was obtained in the same manner as in Japanese Patent No. 6092513, Example 1, 1-2 (however, 3-fluorophenylmagnesium bromide was used instead of 4-chlorophenylmagnesium bromide) using the compound 24 (1.80 g, 2.00 mmol) obtained in Example 17.

Example 19: Synthesis of Compound 26 (2,7-didocosyloxy-9-(3-fluorophenyl)-9-bromofluorene ("2,7-didocosyloxy-9-(3-fluorophenyl)-9-bromofluorenyl Group" is Hereinafter Referred to as "F1 Group" in Some Cases))

[Chemical Formula 165]

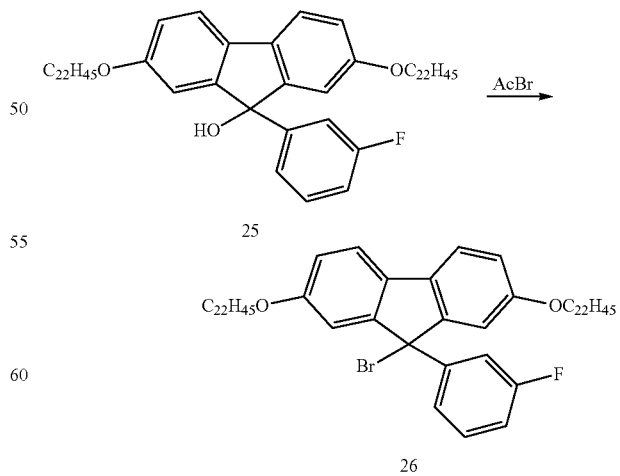

A compound 26 (1.55 g, 1.68 mmol, 83.8%) was obtained in the same manner as in Japanese Patent No. 6092513, Example 1, 1-3 using the compound 25 (1.80 g, 2.00 mmol) obtained in Example 18 instead of 2-docosyloxy-9-(4-chlorophenyl)-9-fluorenol.

Example 20: Synthesis of Compound 27 (Fmoc-Arg(Pbf)-Fl)

[Chemical Formula 166]

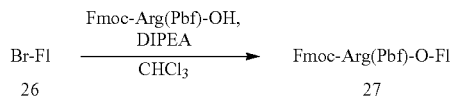

A compound 27 (1.03 g, 0.663 mmol, 73.0%) was obtained in the same manner as in Japanese Patent No. 6092513, Example 6 (however, Fmoc-Arg(Pbf)-OH was used instead of Z-Ala-OH) using 2,7-didocosyloxy-9-(3-fluorophenyl)-9-bromofluorene (0.90 g, 0.91 mmol).

Example 21: Synthesis of Compound 28 (H-Arg(Pbf)—O—Fl)

[Chemical Formula 167]

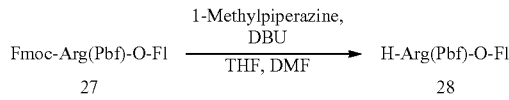

The compound 27 (0.900 g, 0.578 mmol) was subjected to the general synthesis method for Fmoc deprotection described above, using 1-methylpiperazine instead of piperidine, then, washed with hydrochloric acid water, then with a sodium hydrogen carbonate aqueous solution, to obtain a compound 28 in the form of a solution.

Example 22: Synthesis of Compound 29 (H-His(Trt)-Trp(Boc)-Ser(tBu)-Tyr(tBu)-dLeu-Leu-Arg(Pbf)—O—Fl (SEQ ID NO: 24))

[Chemical Formula 168]

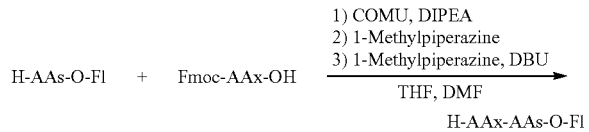

The following amino acids were introduced into the compound 28 by repeating the 1 pot condensation deprotection method using an amine scavenger (water-soluble amine), to obtain a compound 29 in the form of a solution.
1-st residue: Fmoc-Leu-OH
2-nd residue: Fmoc-dLeu-OH
3-rd residue: Fmoc-Tyr(tBu)-OH
4-th residue: Fmoc-Ser(tBu)-OH
5-th residue: Fmoc-Trp(Boc)-OH
6-th residue: Fmoc-His(Trt)-OH Example 23: Synthesis of Compound 30 (Pyr-His(Trt)-Trp(Boc)-Ser(tBu)-Tyr(tBu)-dLeu-Leu-Arg(Pbf)—O—Fl (SEQ ID NO: 25))

[Chemical Formula 169]

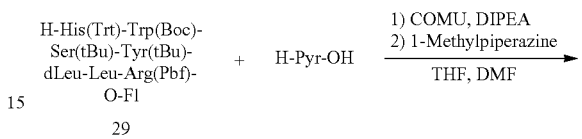

To the resultant compound 29 solution was added DMF so that its proportion was 1.8 v/w with respect to the theoretical yield. H-Pyr-OH (0.097 g, 0.75 mmol), COMU (0.310 g, 0.723 mmol) and DIPEA (0.232 ml, 1.33 mmol) were added. The resultant mixed solution was stirred at room temperature for 30 minutes. To the resultant reaction solution was added 1-methylpiperazine (0.45 equiv.) and the mixture was stirred at room temperature for 5 minutes. The resultant organic layer was distilled under reduced pressure to remove the solvent. To the residue was added acetonitrile and the deposited precipitate was filtrated, and further, suspending and washing with acetonitrile was conducted, and the resultant solid was dried under reduced pressure, to obtain a compound 30 (0.999 g, 0.37 mmol, 64.6%).

Example 24: Synthesis of Compound 23 (Pyr-His-Trp-Ser-Tyr-dLeu-Leu-Arg-OH) (SEQ ID NO: 21)

[Chemical Formula 170]

The compound 30 (5.33 g, 2.78 mmol) was dissolved in 92 ml of a mixed solution of TFA/TIS/water (90/1/9), DTT (3.70 g, 40 mg/ml) was added, and the mixture was stirred at room temperature for 3 hours. The reaction solution was filtrated through Celite, and the filtration residue was washed with methanol and filtrated. To the resultant filtrate was added toluene (same amount as the mixed solution), and the solvent was distilled off under reduced pressure. To the residue was added cold MTBE and the deposited precipitate was filtrated, and further, suspending and washing with MTBE and suspending and washing with hexane were conducted, and the resultant solid was dried under reduced pressure, to obtain a compound 23 (4.21 g, quant, HPLC purity: 76.28%).

Synthesis of Compound 23 (Pyr-His-Trp-Ser-Tyr-dLeu-Leu-Arg-OH) (SEQ ID NO: 21) Using 2,4-di(2',3'-dihydrophytyloxy)benzyl Alcohol

Example 25: Synthesis of Compound 31 (2,3-dihydrophytol ("2,3-dihydrophytyl Group" is Hereinafter Referred to as "Phy" in Some Cases)

[Chemical Formula 171]

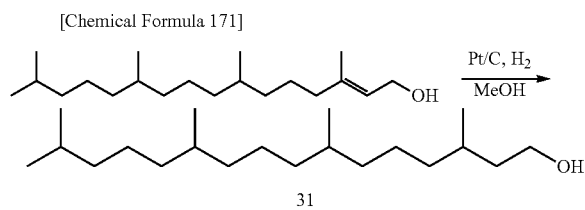

Phytol (10 g, 33.7 mmol) was dissolved in methanol, Pt/C (2%, 1.00 g) was suspended, and the suspension was stirred overnight under a hydrogen atmosphere. After completion of the reaction, the reaction solution was filtrated to remove Pt/C, and the filtrate was concentrated, to obtain a compound 31. This was used in the subsequent reaction without purification.

Example 26: Synthesis of Compound 32 (2,3-dihydrophytyl Bromide)

[Chemical Formula 172]

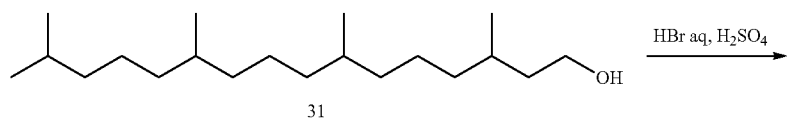

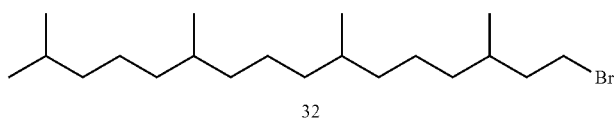

The compound 31 (33.7 mmol) was suspended in 48% hydrobromic acid (100 ml), concentrated sulfuric acid (0.17 ml) was dropped and the mixture was stirred at 100° C. overnight. The reaction mixture was cooled down to room temperature, then, extracted with hexane (200 ml), and washed with a 5% sodium hydrogen carbonate aqueous solution (70 mL) twice, and with 20% saline (25 mL) once. The organic layer was dried over sodium sulfate, the solvent of the filtrate was distilled off to obtain a residue which was then purified by silica gel column chromatography (short column, only hexane), to obtain a compound 32 (10.41 g, 28.8 mmol, 85% vs. phytol).

Example 27: Synthesis of Compound 33 (2,4-di(2',3'-dihydrophytyl)benzyl Alcohol ("2,4-di(2',3'-dihydrophytyl)benzyl Group" is Hereinafter Referred to as "KJ1" in Some Cases))

[Chemical Formula 173]

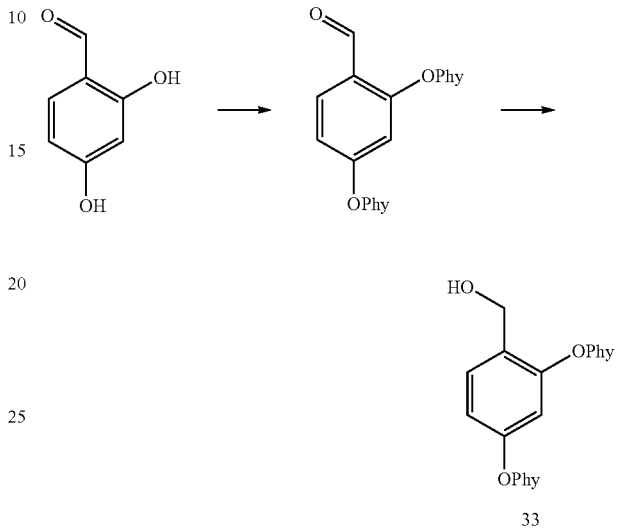

-continued

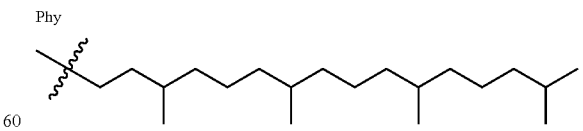

A compound 33 (1.16 g, 1.66 mmol, 96.9%) was obtained in the same manner as in Japanese Patent No. 5929756, Example 1, using 2,4-dihydroxybenzaldehyde (237 mg, 1.716 mmol).

Example 28: Synthesis of Compound 34 (Fmoc-Arg(Pbf)—O—KJ1)

[Chemical Formula 174]

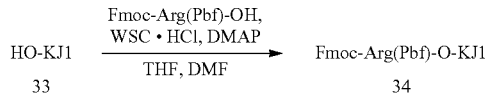

A compound 34 solution was obtained in the same manner as in Japanese Patent No. 5929756, Example 23, using 2,4-di(11'-triisopropylsilyloxyundecyloxybenzyl alcohol (1.76 g, 2.22 mmol), excepting using Fmoc-Arg(Pbf)-OH instead of Fmoc-Ser(tBu)-OH.

The resultant solution was concentrated, to obtain a compound 34 (1.65 g, 2.08 mmol, 93.7%).

Example 29: Synthesis of Compound 35 (H-Arg(Pbf)—O—KJ1)

[Chemical Formula 175]

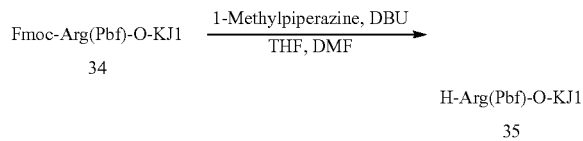

The compound 34 was subjected to the general synthesis method for Fmoc deprotection described above, using 1-methylpiperazine instead of piperidine, then, washed with hydrochloric acid water and with a sodium hydrogen carbonate aqueous solution, to obtain a compound 35 in the form of a solution.

Example 30: Synthesis of Compound 36 (H-His(Trt)-Trp(Boc)-Ser(tBu)-Tyr(tBu)-dLeu-Leu-Arg(Pbf)—O—KJ1 (SEQ ID NO: 26))

[Chemical Formula 176]

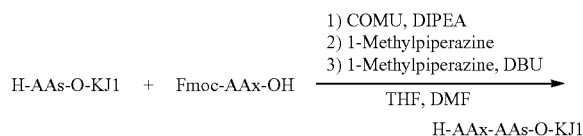

The following amino acids were introduced into the compound 35 by repeating the 1 pot condensation deprotection method using an amine scavenger (water-soluble amine), to obtain a compound 36 in the form of a solution.
1-st residue: Fmoc-Leu-OH
2-nd residue: Fmoc-dLeu-OH
3-rd residue: Fmoc-Tyr(tBu)-OH
4-th residue: Fmoc-Ser(tBu)-OH
5-th residue: Fmoc-Trp(Boc)-OH
6-th residue: Fmoc-His(Trt)-OH

Example 31: Synthesis of Compound 37 (Pyr-His(Trt)-Trp(Boc)-Ser(tBu)-Tyr(tBu)-dLeu-Leu-Arg(Pbf)—O—KJ1 (SEQ ID NO: 27))

[Chemical Formula 177]

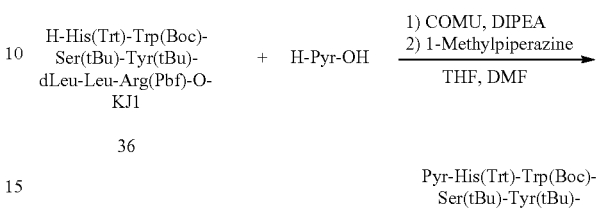

To the resultant compound 36 solution was added DMF so that its proportion was 1.8 v/w with respect to the theoretical yield. H-Pyr-OH (3.30 g, 25.55 mmol), COMU (7.0 g, 16.26 mmol, 1.25 equiv.) and DIPEA (5.10 ml, 29.28 mmol, 2.25 equiv.) were added. The resultant mixed solution was stirred at room temperature for 30 minutes. To the resultant reaction solution was added 1-methylpiperazine (0.45 equiv.) and the mixture was stirred at room temperature for 5 minutes. 0.01 N hydrochloric acid (18 v/w) was added, and the solution was washed, separated, and the aqueous layer was discarded. The resultant organic layer was distilled under reduced pressure to remove the solvent. To the residue was added acetonitrile and the deposited precipitate was filtrated, and further, suspending and washing with acetonitrile was conducted, and the resultant solid was dried under reduced pressure, to obtain a compound 37 (28.78 g, 87.50%).

Example 32: Synthesis of Compound 23 (Pyr-His-Trp-Ser-Tyr-dLeu-Leu-Arg-OH) (SEQ ID NO: 21)

[Chemical Formula 178]

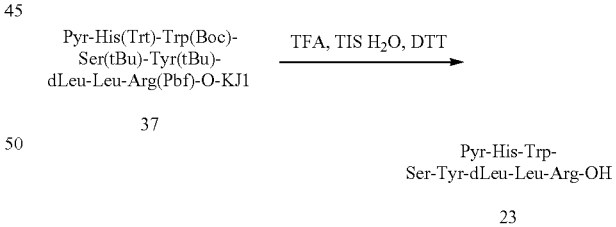

The compound 37 (5.33 g, 2.78 mmol) was dissolved in 92 ml of a mixed solution of TFA/TIS/water (90/1/9), DTT (3.70 g, 40 mg/ml) was added, and the mixture was stirred at room temperature for 3 hours. The reaction solution was filtrated through Celite, and the filtration residue was washed with methanol and filtrated. To the resultant filtrate was added toluene (same amount as the mixed solution), and the solvent was distilled off under reduced pressure. To the residue was added cold MTBE and the deposited precipitate was filtrated, and further, suspending and washing with MTBE was conducted, and suspending and washing with hexane was conducted, and the resultant solid was dried under reduced pressure, to obtain a compound 23 (4.21 g, quant, HPLC purity: 76.28%).

Synthesis of Compound 7 (Pyr-His-Trp-Ser-Tyr-dLeu-Leu-Arg-Pro-NHEt) (SEQ ID NO: 2) Using (N-ethyl-(bis(4-docosyloxyphenyl))methylamine Example 33: Synthesis of Compound 38 (4,4'-didocosyloxybenzophenone)

[Chemical Formula 179]

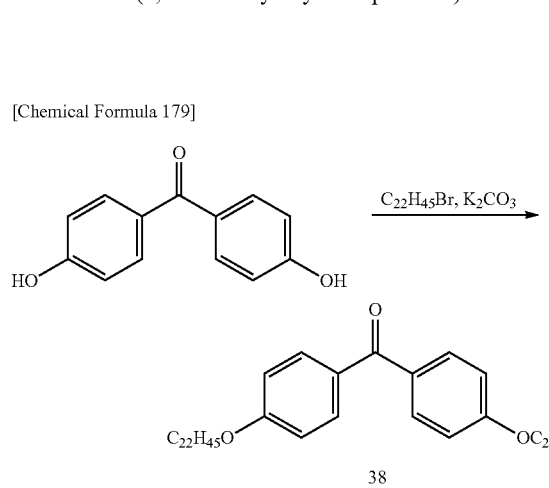

A compound 38 (7.91 g, 95.2%) was obtained in the same manner as in Japanese Patent No. 5768712, Example 4, 4-1, using 4,4'-dihydroxybenzophenone (2.14 g, 10 mmol).

Example 34: Synthesis of Compound 39 (4,4'-didocosyloxyphenylbenzohydrol)

[Chemical Formula 180]

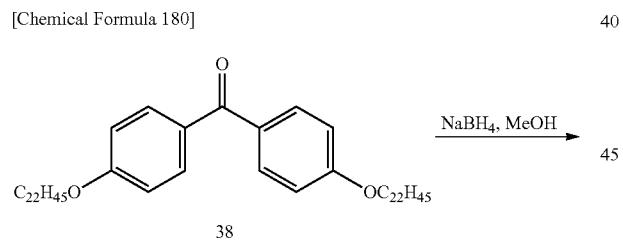

A compound 39 (7.72 g, 9.26 mmol, 97.3%) was obtained in the same manner as in Japanese Patent No. 5768712, Example 4, 4-2, using the compound 38 (7.91 g, 9.52 mmol).

Example 35: Synthesis of Compound 40 (N-ethyl-(bis(4-docosyloxyphenyl))methylamine (N-ethyl-(bis(4-docosyloxyphenyl))methylamino Group is Hereinafter Referred to as "NEt-KJ3" in Some Cases))

[Chemical Formula 181]

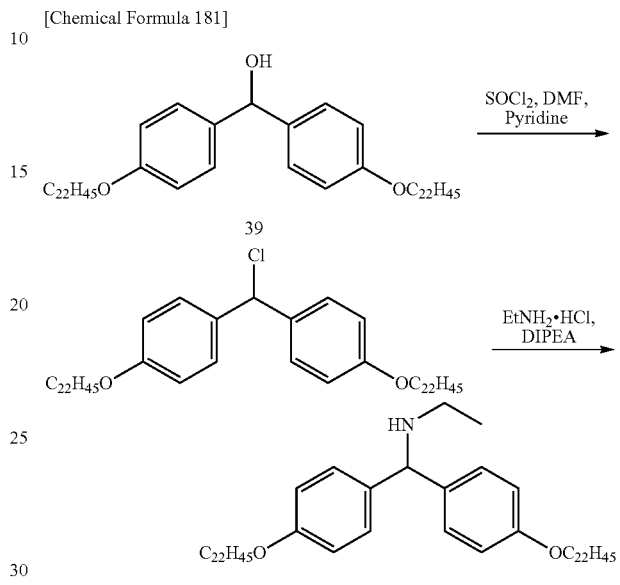

A compound 40 (0.829 g, 96.6%) was obtained in the same manner as in Japanese Patent No. 6283774, Example 9, (1) and (2), using the compound 39 (0.833 g, 1.00 mmol) instead of TIPS4-Dpm-OH ($C_{10}$—CONH—CH($CH_2$)$_2$), and further, using ethylamine hydrochloride (5 mmol) instead of propylamine, and further using DIPEA (8 mmol).

Example 36: Synthesis of Compound 41 (Fmoc-Arg(Pbf)-NEt-Kj3)

[Chemical Formula 182]

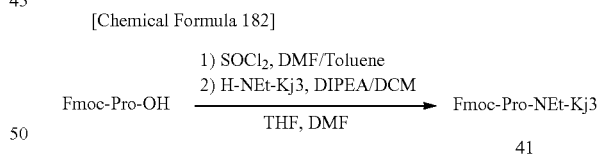

Fmoc-Pro-OH (0.354 g, 1.05 mmol) was dissolved in 14 ml of toluene, DMF (10.8 µL, 0.14 mmol) was added, and then, thionyl chloride (91 µL, 1.26 mmol) was added, and the mixture was heated at 40° C., and stirred for 2 hours. Further, thionyl chloride (45.5 µL, 0.63 mmol) was added and the mixture was stirred for 1 hour. The resultant reaction solution was concentrated under reduced pressure. To the residue was added 7 mL of toluene and the mixture was concentrated under reduced pressure, and this operation was repeated twice. The resultant residue was cooled down to room temperature, then, 14 ml of dichloromethane was added to dissolve it, and DIPEA (244 µL, 1.4 mmol) was added for dissolution. To the resultant mixed solution was added the compound 40 (0.601 g, 0.7 mmol) obtained in Example 35 and the mixture was stirred for 1 hour. The resultant reaction solution was concentrated under reduced pressure, 20 ml of acetonitrile was added, and the resultant slurry solution was filtrated, to obtain a crude compound 41. The resultant crude compound 41 was subjected to silica gel column chromatography (mobile phase: dichloromethane), and the target fractions were collected and concentrated, to obtain a compound 41 (0.58 g, 0.53 mmol, 75.1%).

Example 37: Synthesis of Compound 42 (H-Pro-NEt-KJ3)

[Chemical Formula 183]

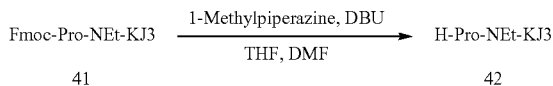

The compound 41 (0.500 g, 0.424 mmol) was subjected to the general synthesis method for Fmoc deprotection described above, using 1-methylpiperazine instead of piperidine, then, washed with hydrochloric acid water and with a sodium hydrogen carbonate aqueous solution, to obtain the compound 42 in the form of a solution.

Example 38: Synthesis of Compound 43 (H-His(Trt)-Trp(Boc)-Ser(tBu)-Tyr(tBu)-dLeu-Leu-Arg(Pbf)-Pro-NEt-KJ3 (SEQ ID NO: 28))

[Chemical Formula 184]

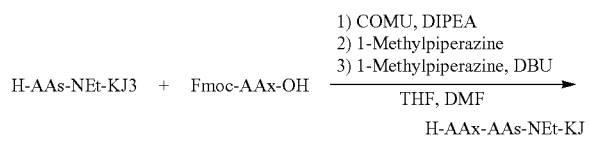

The following amino acids were introduced into the compound 42 by repeating the 1 pot condensation deprotection method using an amine scavenger (water-soluble amine), to obtain a compound 43 in the form of a solution.
1-st residue: Fmoc-Arg(Pbf)-OH
2-nd residue: Fmoc-Leu-OH
3-rd residue: Fmoc-dLeu-OH
4-th residue: Fmoc-Tyr(tBu)-OH
5-th residue: Fmoc-Ser(tBu)-OH
6-th residue: Fmoc-Trp(Boc)-OH
7-th residue: Fmoc-His(Trt)-OH

Example 39: Synthesis of Compound 44 (Pyr-His(Trt)-Trp(Boc)-Ser(tBu)-Tyr(tBu)-dLeu-Leu-Arg(Pbf)-Pro-NEt-KJ3 (SEQ ID NO: 29))

[Chemical Formula 185]

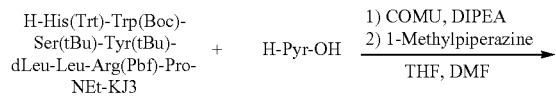

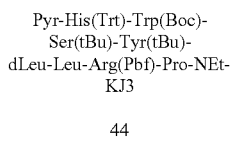

To the resultant compound 43 solution was added DMF so that its proportion was 1.8 v/w with respect to the theoretical yield. H-Pyr-OH (53 mg, 0.41 mmol, 1.45 eq.), COMU (171 mg, 0.40 mmol, 1.40 equiv.) and DIPEA (0.12 ml, 0.69 mmol, 2.5 equiv.) were added. The resultant mixed solution was stirred at room temperature for 30 minutes. To the resultant reaction solution was added 1-methylpiperazine (0.6 equiv.) and the mixture was stirred at room temperature for 5 minutes. 0.1 N hydrochloric acid (18 v/w) was added, and the solution was washed, separated, and the aqueous layer was discarded. The resultant organic layer was distilled under reduced pressure to remove the solvent. To the residue was added acetonitrile and the deposited precipitate was filtrated, and further, suspending and washing with acetonitrile was conducted, and the resultant solid was dried under reduced pressure, to obtain a compound 44 (0.998 g, 64.6%, HPLC purity: 86.10%).

Example 40: Synthesis of Compound 7 (Pyr-His-Trp-Ser-Tyr-dLeu-Leu-Arg-Pro-NHEt) (SEQ ID NO: 2)

[Chemical Formula 186]

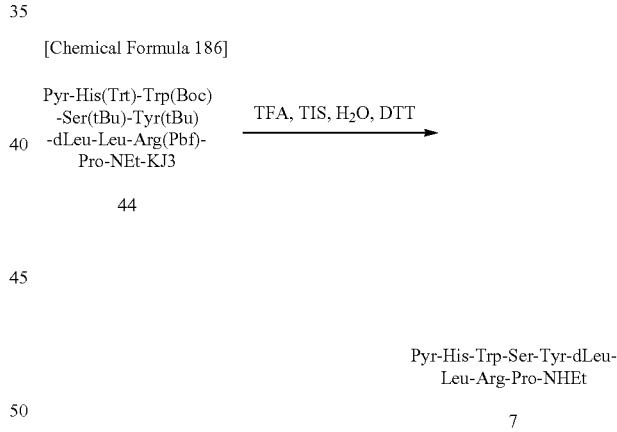

The compound 44 (0.10 g, 0.037 mmol) was dissolved in 1.23 ml of a mixed solution of TFA/TIS/water (90/1/9), DTT (25 mg, 20 mg/ml) was added, and the mixture was stirred at room temperature for 3 hours. The reaction solution was filtrated through Celite, and the filtration residue was washed with methanol and filtrated. To the resultant filtrate was added toluene (same amount as the mixed solution), and the solvent was distilled off under reduced pressure. To the residue was added cold MTBE and the deposited precipitate was filtrated, and further, suspending and washing with MTBE and suspending and washing with hexane were conducted, and the resultant solid was dried under reduced pressure, to obtain a compound 7 (19 mg, 47.5%, HPLC purity: 94.93%).

Example 41: Synthesis of Compound 49 (TFA.H-Ser-Pro-Leu-Gln-OH (SEQ ID NO: 30))

Synthesis of Compound 45 (Fmoc-Gln(Trt)-OKb)

[Chemical Formula 187]

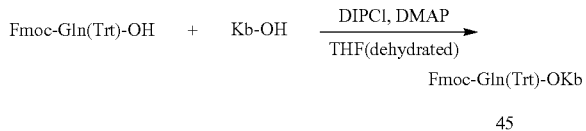

2,4-didocosyloxybenzyl alcohol (expressed as "Kb-OH") (1.0 g, 1.32 mmol) was dissolved in dehydrated THF (13 ml), and Fmoc-Gln(Trt)-OH (1.21 g, 1.98 mmol, 1.5 equiv.), DIPCI (0.307 ml, 1.98 mmol, 1.5 equiv.) and DMAP (8.3 mg, 0.066 mmol, 0.05 equiv.) were added and the mixture was stirred at room temperature for 30 minutes. The reaction solution was subject to distillation off under reduced pressure. To the residue was added methanol and the deposited precipitate was filtrated, suspending and washing with methanol was conducted, and further, suspending and washing with acetonitrile was conducted twice. The resultant solid was dried under reduced pressure, to obtain a compound 45 (1.77 g, 99.5%).

Synthesis of Compound 46 (H-Gln(Trt)-OKb)

[Chemical Formula 188]

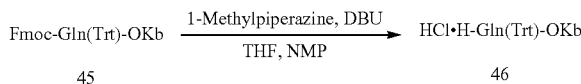

The compound 45 was subjected to the general synthesis method for Fmoc deprotection described above, using NMP instead of DMF and using 1-methylpiperazine instead of piperidine, then, washed with hydrochloric acid water and with a sodium hydrogen carbonate aqueous solution, to obtain a compound 46 in the form of a solution.

Synthesis of Compound 47 (H-Pro-Leu-Gln(Trt)-OKb (SEQ ID NO: 31))

[Chemical Formula 189]

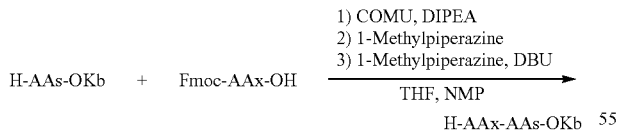

The following amino acids were sequentially condensed with the compound 46, and each time, an amine scavenger was added, followed by the deprotection operation, and washing with hydrochloric acid water and with a sodium hydrogen carbonate aqueous solution were conducted. This 1 pot condensation deprotection method was repeated, to obtain a compound 47 in the form of a solution.

1-st residue: Fmoc-Leu-OH
2-nd residue: Fmoc-Pro-OH

Synthesis of Compound 48 (Boc-Ser(tBu)-Pro-Leu-Gln(Trt)-OKb (SEQ ID NO: 32))

[Chemical Formula 190]

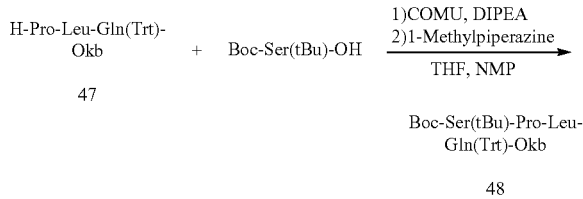

To the solution of the compound 47 were added Boc-Ser(tBu)-OH (0.445 g, 1.70 mmol, 1.30 equiv.), COMU (0.702 g, 1.64 mmol, 1.25 equiv.) and DIPEA (0.571 ml, 3.3 mmol, 2.5 equiv.). The resultant mixed solution was stirred at room temperature for 30 minutes. Washing with a 0.1 N hydrochloric acid water (10 ml), subsequently with a 0.5 N sodium hydrogen carbonate aqueous solution (10 ml) and then liquid-liquid separation operations thereof were performed respectively, and the resultant organic layer was distilled under reduced pressure to remove the solvent. To the residue was added acetonitrile and the deposited precipitate was filtrated, and further, suspending and washing with acetonitrile was conducted, and the resultant solid was dried under reduced pressure, to obtain a compound 48 (1.83 g, 88.4%).

Synthesis of Compound 49 (TFA.H-Ser-Pro-Leu-Gln-OH (SEQ ID NO: 30))

The compound 48 (0.50 g, 0.32 mmol) was dissolved in 15.8 ml of a mixed solution of TFA/TIS/water (95/2.5/2.5), and the mixture was stirred at room temperature for 3 hours. The reaction solution was filtrated through Celite, the residue was washed with TFA, and the filtrate and the washing solution were combined and distilled under reduced pressure to remove the solvent. To the residue was added cold MTBE and the deposited precipitate was collected by filtration, then, suspending and washing with MTBE was performed twice, and the resultant solid was dried under reduced pressure, to obtain a compound 49 (0.14 g, 78.3%, HPLC purity: 84.93%).

The foregoing merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The peptide synthesis method of the present invention can simultaneously solve the problem of an amino acid active ester and the problem of DBF existing in the reaction system and can reduce the solid-liquid separation operation, by a simple means. According to the present invention, the process time of peptide synthesis can be shortened, and use of a solvent can be reduced by reducing the solid-liquid separation operation. Further, the peptide synthesized according to the present invention has few problems of amino acid missing and double hits, and according to the method of the present invention, peptides can be synthesized with high quality and/or at high yield.

The invention claimed is:

1. A liquid phase peptide synthesis method, comprising the following steps a to d:
   a: condensing an amino acid protected with a carrier for liquid phase peptide synthesis (carrier-protected amino acid), a carrier-protected peptide or a carrier-protected amino acid amide, with an amino acid in which an amino group is protected with a 9-fluorenylmethyloxycarbonyl (Fmoc) group (N-Fmoc-protected amino acid) or an N-Fmoc-protected peptide in an organic solvent or a mixed solution of organic solvents, to obtain a reaction solution including an N-Fmoc-carrier-protected peptide,
   b: adding a water-soluble amine having a valency of at least 2 and having at least one primary or secondary amino group to the reaction solution resulting from step (a) after the condensation reaction,
   c: performing deprotection of the Fmoc group from the protected amino group in the presence of a water-soluble amine to obtain a second reaction solution, and
   d: adding an acid to neutralize the second reaction solution resulting from step (c), and further, adding and washing the neutralized solution with an acidic aqueous solution, then, separating the washed solution into an aqueous layer and an organic layer and removing the aqueous layer to obtain the organic layer,
   wherein
   the carrier for liquid phase peptide synthesis is a compound binding to an amino acid, a peptide or an amino acid amide directly or via a linker to make them insoluble in water and having a molecular weight of 300 or more,
   the carrier-protected amino acid, peptide or amino acid amide is an amino acid, a peptide or an amino acid amide in which the carrier is bonded directly or via a linker to any of an amino group, a carboxyl group, a thiol group and a hydroxyl group of the amino acid, peptide or amino acid amide, and the water-soluble amines in the step b and the step c may be the same or different.

2. The peptide synthesis method according to claim 1, wherein the carrier for liquid phase peptide synthesis is a carrier derived from a compound selected from the group consisting of:

a compound having the following structure:

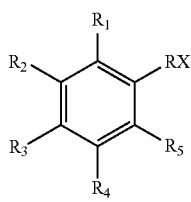

(wherein, $R_1$ and $R_5$ are hydrogen atoms, $R_2$, $R_3$ and $R_4$ are alkoxy groups having 8 to 30 carbon atoms, RX is a group represented by the following formulae and binding to a carboxyl group, an amino group or a hydroxyl group of an amino acid, a peptide or an amino acid amide or to a linker)

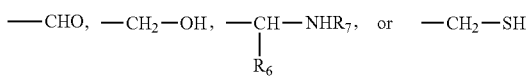

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group), a compound having the following structure:

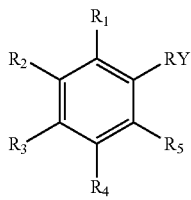

(wherein, $R_2$, $R_4$ and $R_5$ are hydrogen atoms, $R_1$ and $R_3$ are alkoxy groups having 12 to 30 carbon atoms, RY is a group represented by the following formulae and binding to a carboxyl group, an amino group or a hydroxyl group of an amino acid, a peptide or an amino acid amide or to a linker)

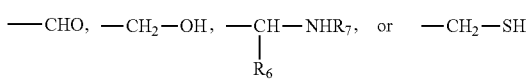

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group)

and a compound having the following structure:

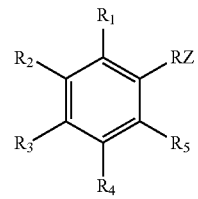

(wherein, $R_1$, $R_3$ and $R_5$ are hydrogen atoms, $R_2$ and $R_4$ are alkoxy groups having 12 to 30 carbon atoms, RZ is a group represented by the following formulae and binding to a carboxyl group, an amino group or a hydroxyl group of an amino acid, a peptide or an amino acid amide or to a linker)

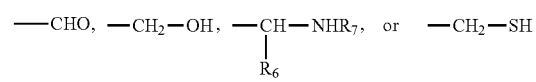

(wherein, $R_7$ represents a hydrogen atom, an alkyl group having 1 to 6 carbon atoms, a benzyl group or an alkoxy-substituted benzyl group, and R6 represents a hydrogen atom, a phenyl group or an alkoxy-substituted phenyl group).

3. The peptide synthesis method according to claim 1, wherein the carrier for liquid phase peptide synthesis is a carrier derived from a compound having the following structure:

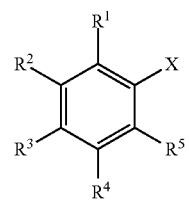

(wherein, X is a group representing —$CH_2$ ORa (wherein, Ra represents a hydrogen atom, a halogenocarbonyl group or an active ester type protective group), —$CH_2$NHRb (wherein, Rb represents a hydrogen atom, a linear or branched alkyl group having 1 to 6 carbon atoms or an aralkyl group), a halogenomethyl group, a methyl azide group, a formyl group or an oxime, and binding to a carboxyl group, an amino group or a hydroxyl group of an amino acid, a peptide or an amino acid amide or to a linker; at least one of $R^1$, $R^2$, $R^3$, $R^4$ an $R^5$ represents a group represented by the following formula:

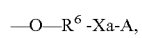

—O—$R^6$-Xa-A, and the residual groups represent a hydrogen atom, a halogen atom, an alkyl group having 1 to 4 carbon atoms or an alkoxy group having 1 to 4 carbon atoms; $R^6$ represents a linear or branched alkylene group having 1 to 16 carbon atoms, Xa represents O or CONRc (wherein, Rc represents a hydrogen atom or an alkyl group having 1 to 4 carbon atoms), A represents any of the formula(1) to the formula (11),

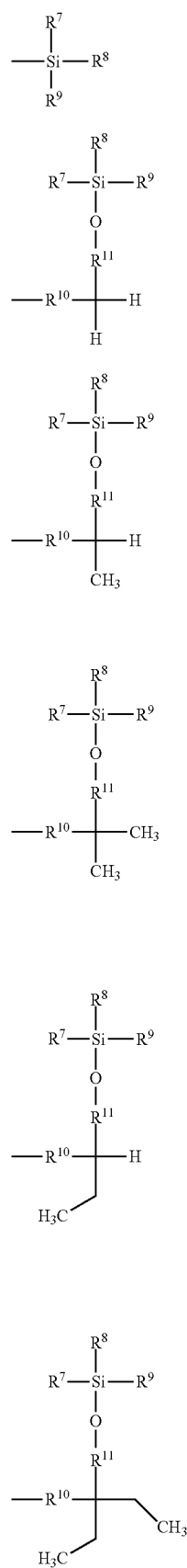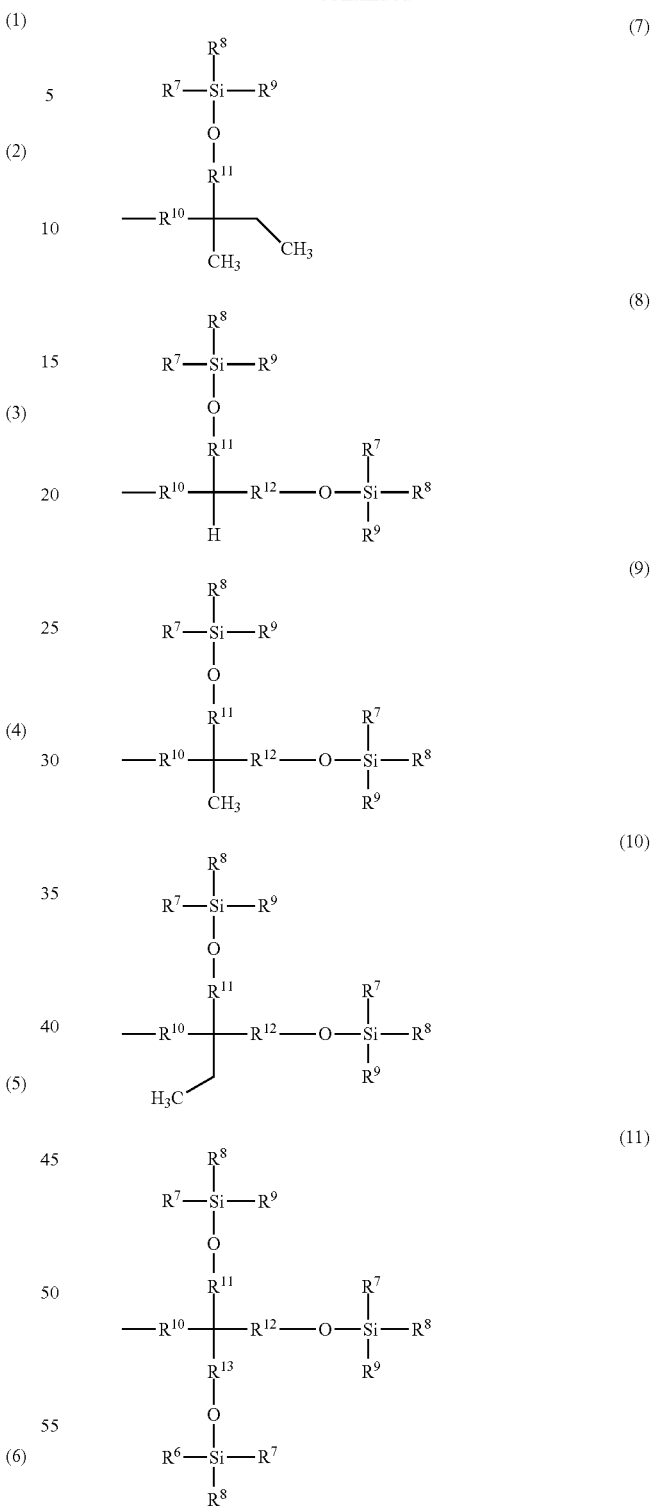

(wherein, $R^7$, $R^8$ and $R^9$ may be the same or different and represent a linear or branched alkyl group having 1 to 6 carbon atoms, or an aryl group optionally having a substituent, $R^{10}$ represents a single bond or a linear or branched alkylene group having 1 to 3 carbon atoms, and $R^{11}$, $R^{12}$ and $R^{13}$ may be the same or different and represent a linear or branched alkylene group having 1 to 3 carbon atoms)

wherein, the formula is shown in the condition before binding to a carboxyl group, an amino group or a hydroxyl group of an amino acid, a peptide or an amino acid amide or to a linker.

4. The peptide synthesis method according to claim 1, wherein the carrier for liquid phase peptide synthesis is a carrier derived from a fluorene compound represented by, the general formula (V):

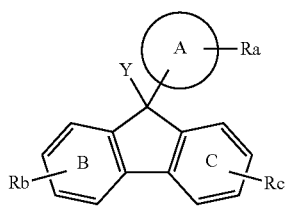

(V)

[wherein, Ring A represents an aromatic ring; Y is a hydroxyl group, a bromo group or a chloro group; Ra, Rb and Rc each independently represent an organic group having an aliphatic hydrocarbon group, a hydrogen atom or an electron withdrawing group, and at least one of Ra, Rb and Rc is an organic group having an aliphatic hydrocarbon group; Rings A, B and C each independently may have an electron withdrawing group], or the general formula (V'):

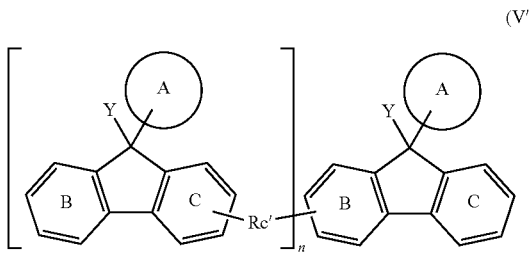

(V')

[wherein, Ring A represents an aromatic ring; Y is a hydroxyl group, a bromo group or a chloro group; n represents an integer of 1 to 19; Rc' is a divalent organic group having an aliphatic hydrocarbon group; Rings A, B and C each independently may have at least one group selected from an organic group having an aliphatic hydrocarbon group and an electron withdrawing group, wherein when Ring B and/or Ring C has at least one organic group having an aliphatic hydrocarbon group, Ring B and/or Ring C of Formula (V') has at least one organic group having an aliphatic hydrocarbon at the 2-position and/or the 7-position of the fluorene compound; when a plurality of Rings A are present, the respective Rings A may be the same or different; when a plurality of groups Y are present, the respective groups Y may be the same or different; when a plurality of groups Rc' are present, the respective groups Rc' may be the same or different, wherein, the divalent organic group having an aliphatic hydrocarbon group in Formula V' is a group represented by the formula (a):

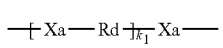

(a)

(wherein, Xa is not present or represents —O—, —S—, —NHCO— or —CONH—; Rd represents an aliphatic hydrocarbon group having 5 or more carbon atoms; $k_1$ represents an integer of 1 to 10; when a plurality of groups Rd are present, the respective groups Rd may be the same or different; and when a plurality of groups Xa are present, the respective groups Xa may be the same or different), wherein, the at least one organic group having an aliphatic hydrocarbon group which exists at the 2-position and/or the 7-position of the fluorene compound for Ring B and/or Ring C of Formula V' is at least one selected from the group consisting of a group represented by the formula (b):

(b)

(wherein, * represents the binding position; $X_1$ is —O—; $R_1$ is an aliphatic hydrocarbon group having 5 to 60 carbon atoms; and $m_1$ is 1), a group represented by the formula (c):

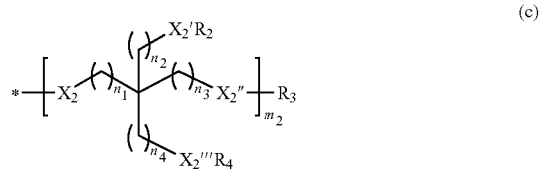

(c)

(wherein, * represents the binding position; $X_2$, $X_2'$, $X_2''$ and $X_2'''$ are —O—; $R_2$ and $R_4$ are each independently aliphatic hydrocarbon groups having 5 to 60 carbon atoms; $R_3$ is an organic group having an aliphatic hydrocarbon group having 5 to 60 carbon atoms; $n_1$, $n_2$, $n_3$ and $n_4$ are 1; and $m_2$ is 1), and a group represented by the formula(d):

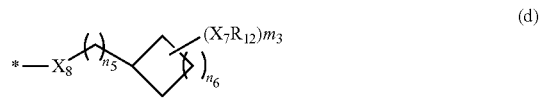

(d)

(wherein, * represents the binding position; $X_8$ represents —O—; $m_3$ is 2 or 3; $n_5$ is 1; no is 3; $X_7$ is —O—; each $R_{12}$ independently represents alkyl groups having 4 to 30 carbon atom s)]

wherein, each of the formula is shown in the condition before binding to a carboxyl group, an amino group or a hydroxyl group of an amino acid, a peptide or an amino acid amide or to a linker.

5. The peptide synthesis method according to claim 1, wherein the carrier for liquid phase peptide synthesis is a carrier derived from a benzyl compound represented by the general formula (W):

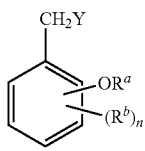

(W)

(wherein, Y represents a hydroxyl group or an —NHR group (R represents a hydrogen atom, an alkyl group or an aralkyl group);

$R^a$ represents an organic group having an aliphatic hydrocarbon group selected from the group consisting of:

a group represented by the formula (e):

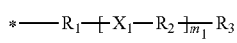

(e)

wherein, * represents the binding position; $m_1$ represents an integer of 1 to 10; $X_1$ each independently represents a single bond or represents —O—, —S—, —COO—, —OCONH—, —NHCO— or —CONH—; $R_1$ and $R_2$ each independently represents a divalent aliphatic hydrocarbon group having 5 or more carbon atoms; and $R_3$ is a hydrogen atom or a group represented by the formula (W'):

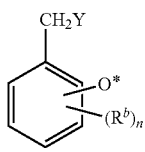

(W')

(wherein, * represents the binding position; $R^b$ each independently represents an alkoxy group having 1 to 6 carbon atoms, a halogen atom, or an alkyl group having 1 to 6 carbon atoms optionally substituted with one or more halogen atoms; and n represents an integer of 0 to 4);

a group represented by the formula (f):

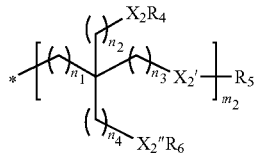

(f)

(wherein, * represents the binding position; $m_2$ represents 1 or 2; $n_1$ $n_2$, $n_3$ and $n_4$ each independently represent an integer of 0 to 2; $X_2$ $X_2$' and $X_2$" each independently represents a single bond or represents —O—, —S—, —COO—, —OCONH—, —NHCO— or —CONH—, $R_4$ and $R_6$ each independently represents an aliphatic hydrocarbon group having 5 or more carbon atoms; $R_5$ represents an aliphatic hydrocarbon group having 5 or more carbon atoms);

a group represented by the formula (g):

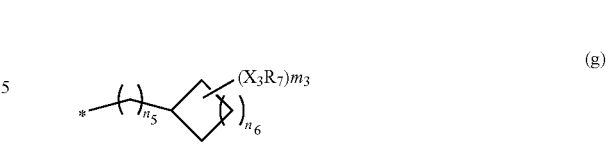

(g)

(wherein, * represents the binding position; $m_3$ represents an integer of 0 to 155; $n_5$ represents an integer of 0 to 11; $n_6$ represents an integer of 0 to 5; $X_3$ each independently represents a single bond or represents —O—, —S—, —COO—, —OCONH—, —NHCO— or —CONH—; and $R_7$ each independently represents a hydrogen atom, a methyl group or an aliphatic hydrocarbon group having 5 or more carbon atoms); and a group represented by the formula (h):

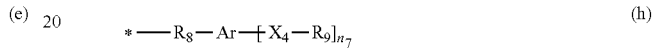

(h)

(wherein, * represents the binding position; $X_4$ each independently represents a single bond or represents —O—, —S—, —COO—, —OCONH—, —NHCO— or —CONH—; $R_8$ represents a divalent aliphatic hydrocarbon group; $R_9$ each independently represents a monovalent aliphatic hydrocarbon group; $n_7$ represents an integer of 1 to 5; and Ar represents an arylene group), wherein the total number of carbon atoms in the organic group of $R^a$ is 30 or more; $R^b$ each independently represents an alkoxy group having 1 to 6 carbon atoms, a halogen atom, or an alkyl group having 1 to 6 carbon atoms optionally substituted with one or more halogen atoms; and n represents an integer of 0 to 4)

wherein; the formula is shown in the condition before binding to a carboxyl group; an amino group or a hydroxyl group of an amino acid, a peptide or an amino acid amide or to a linker.

6. The peptide synthesis method according to claim 1, wherein the carrier for liquid phase peptide synthesis is a carrier derived from a diphenylmethyl compound represented by the general formula (X):

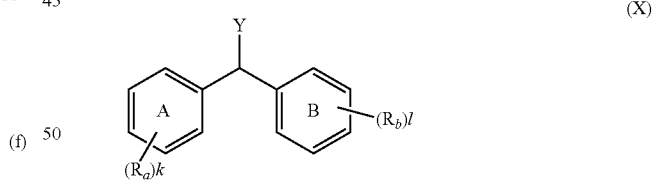

(X)

wherein, Y represents a hydroxyl group or an —NHR group (R represents a hydrogen atom, an alkyl group or an aralkyl group); k and l each independently represent an integer of 0 to 5, providing k+l is not 0; $R_a$ and $R_b$ each independently represents an organic group having an aliphatic hydrocarbon group having 5 or more carbon atoms selected from the group consisting of:

a group represented by the formula (a):

(a)

(wherein, * represents the binding position; $m_1$ represents an integer of 1 to 10; $X_1$ each independently is not present or represents —O—, —S—, —COO—, —OCONH— or —CONH—; $R_1$ each independently represents a divalent aliphatic hydrocarbon group having 5 or more carbon atoms), a group represented by the formula (c)

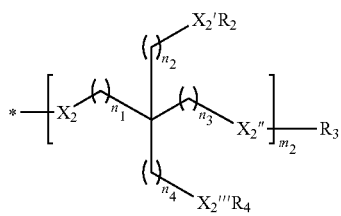

(c)

(wherein, * represents the binding position; $m_2$ represents an integer of 1 to 2; $n_1$, $n_2$, $n_3$ and $n_4$ each independently represents an integer of 0 to 2; $X_2$, $X_2'$, $X_2'''$ and $X_2''$ each independently is not present or represents —O—, —S—, —COO—, —OCONH— or —CONH—; $R_2$ and $R_4$ each independently represents a hydrogen atom, a methyl group or an aliphatic hydrocarbon group having 5 or more carbon atoms; and $R_3$ represents an aliphatic hydrocarbon group having 5 or more carbon atoms), and a group represented by the formula (k):

(k)

(wherein, * represents the binding position; $m_3$ represents an integer of 0 to 5; $n_5$ represents an integer of 0 to 11; $n_6$ represents an integer of 0 to 5; $X_2$ is not present or represents —O—, —S—, —NHCO— or —CONH—, $X_7$ each independently is not present or represents —O—, —S—, —COO—, —OCONH—, —NHCO— or —CONH—; $R_{12}$ each independently represents a hydrogen atom, a methyl group or an aliphatic hydrocarbon group having 5 or more carbon atoms), wherein the total number of carbon atoms of all aliphatic hydrocarbon groups in the organic group having (k+1) aliphatic hydrocarbon groups is 16 or more; Ring A optionally further has a substituent in addition to $R_a$; Ring B optionally further has a substituent in addition to $R_b$ or a branched chain-containing aromatic compound represented by the general formula (Y):

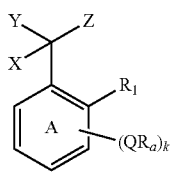

(Y)

wherein, Q each independently represents a single bond or represents —O—, —S—, C(=O)O—, —C(=O)NH— or —NH—; $R_a$ each independently represents an organic group having at least one aliphatic hydrocarbon group having one or more branched chains, having a total number of branched chains of 3 or more and having a total number of carbon atoms from 14 to 300; k represents an integer of 1 to 4; is a hydrogen atom, alternatively, when Z is a group represented by the following formula (a), may represent a single bond together with $R_2$ and may form a fluorene ring together with Ring B; Ring A optionally has at least one substituent selected from the group consisting of a halogen atom, a C1-6 alkoxy group optionally substituted with one or more halogen atoms and a C1-6 alkoxy group optionally substituted with one or more halogen atoms, in addition to $R_1$, k groups $QR_a$ and C(X)(Y)Z; X represents a hydrogen atom or a phenyl group; Y represents a hydroxyl group or an —NHR group (R represents a hydrogen atom, an alkyl group or an aralkyl group);

and Z represents a hydrogen atom or a group represented by the formula (i):

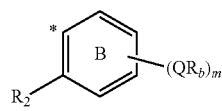

(i)

(wherein, * represents the binding position; m represents an integer of 0 to 4; Q each represents the same meaning as described above; $R_b$ each independently represents an organic group having at least one aliphatic hydrocarbon group having one or more branched chains, having a total number of branched chains of 3 or more and having a total number of carbon atoms from 14 to 300; $R_2$ represents a hydrogen atom, or may represent a single bond together with $R_1$ and may form a fluorene ring together with Ring A; and Ring B optionally has at least one substituent selected from the group consisting of a halogen atom, a $C_{1-6}$ alkyl group optionally substituted with one or more halogen atoms and a $C_{1-6}$ alkoxy group optionally substituted with one or more halogen atoms, in addition to m groups $QR_b$, and $R_2$)

and the organic group having at least one aliphatic hydrocarbon group having one or more branched chains, having a total number of branched chains of 3 or more and having a total number of carbon atoms from 14 to 300 represented by $R_a$ and $R_b$ is a group having 3 or more the same or different divalent groups represented by the formula (j):

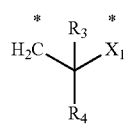

(j)

(wherein, * represents the binding position to an adjacent atom; $R_3$ and $R_4$ each independently represent a hydrogen atom or a C1-4 alkyl group; $X_1$ represents a single bond, a C1-4 alkylene group or an oxygen atom: however, R and $R_4$ are not simultaneously hydrogen atoms)

wherein, each of the formulae is shown in the condition before binding to a carboxyl group, an amino group or a hydroxyl group of an amino acid, a peptide or an amino acid amide or to a linker.

7. The peptide synthesis method according to claim 1, wherein the carrier for liquid phase peptide synthesis is a carrier derived from a compound selected from the group consisting of:

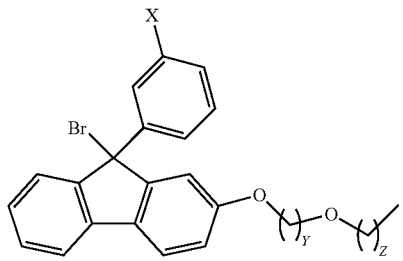

(wherein, X is a halogen, Y is an integer of 8 to 12, Z is an integer of 17 to 29),

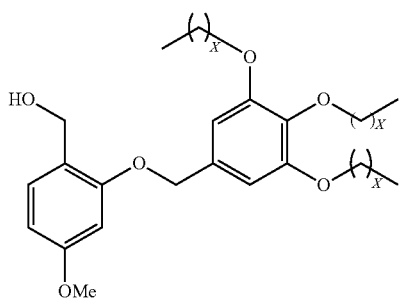

(wherein, each X is independently an integer of 7 to 21),

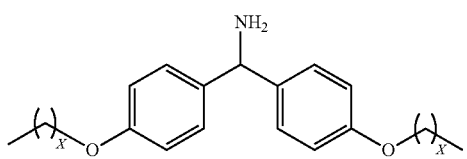

(wherein, each X is independently an integer of 11 to 29), and a branched chain-containing aromatic compound represented by the following formula (Y):

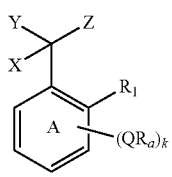

(Y)

(wherein, each independently represent —O—; $R_a$ each independently is the group represented by the following formula (Z):

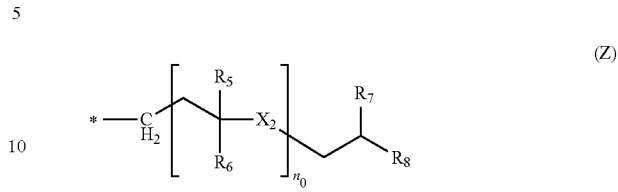

(Z)

(wherein, * represents the binding position to Q; $n_0$ represents an integer of 2 to 40; $R_5$ and $R_6$ each independently represent a hydrogen atom or a $C_{1-4}$ alkyl group (however, they are not simultaneously hydrogen atoms); $X_2$ each independently represents a single bond or a $C_{1-4}$ alkylene group; and $R_7$ represents a hydrogen atom or a $C_{1-4}$ alkyl group; $R_8$ represents a $C_{1-4}$ alkyl group); k represents an integer of 1 to 4; $R_1$ is a hydrogen atom, alternatively, when Z is a group represented by the following formula (a), may represent a single bond together with $R_2$ and may form a fluorene ring together with Ring B; X represents a hydrogen atom or a phenyl group; Y represents a hydroxyl group or an —NHR group (R represents a hydrogen atom, an alkyl group or an aralkyl group); and Z is a hydrogen atom or a group represented by the formula

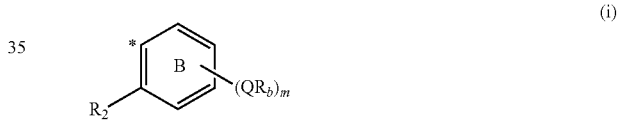

(i)

(wherein, * represents the binding position; m represents an integer of 0 to 4; Q each represents the same meaning as described above; $R_b$ each independently represents a group of the formula (Z); $R_2$ represents a hydrogen atom, or may represent a single bond together with $R_1$ and may form a fluorene ring together with Ring A; and Ring B is optionally further substituted with one or more halogen atoms, in addition to $QR_b$ and $R_2$))

wherein, each of the formula is shown in the condition before binding to a carboxyl group, an amino group, a thiol group or a hydroxyl group of an amino acid, a peptide or an amino acid amide or to a linker.

8. The peptide synthesis method according to claim 1, wherein the carrier for liquid phase peptide synthesis is a carrier derived from a compound having the following structure:

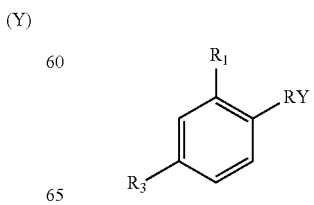

(wherein, $R_1$ and $R_3$ are alkoxy groups having 18 to 22 carbon atoms, and RY is a group represented by the following formulae and binding to a carboxyl group, an amino group or a hydroxyl group of an amino acid, a peptide or an amino acid amide or to a linker, —$CH_2$—OH,  —$CH_2$—$NHR_7$,  or  —CHO (wherein, $R_7$ represents a hydrogen atom or an alkyl group having 1 to 6 carbon atoms))

wherein, the formulae are shown in the condition before binding to a carboxyl group, an amino group or a hydroxyl group of an amino acid, a peptide or an amino acid amide or to a linker.

9. The peptide synthesis method according to claim 1, wherein the carrier for liquid phase peptide synthesis is a carrier derived from a compound selected from the group consisting of:

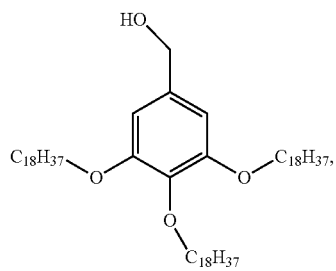
(3,4,5-trioctadecyloxybenzyl alcohol)

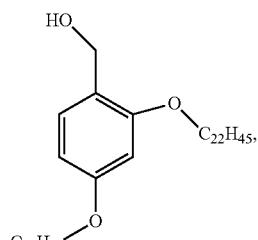
(2,4-didocosyloxybenzyl alcohol)

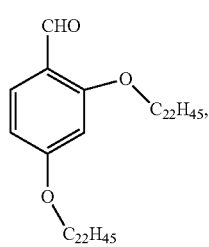
(2,4-didocosyloxy benzaldehyde)

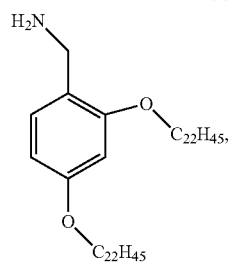
(2,4-didocosyloxy benzylamine)

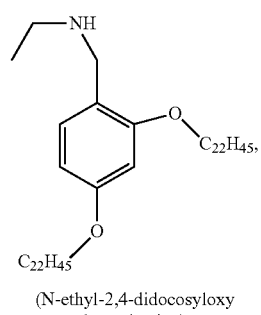
(N-ethyl-2,4-didocosyloxy benzylamine)

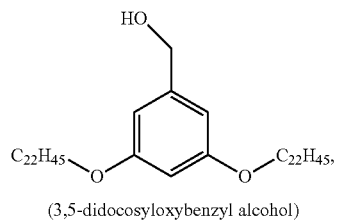
(3,5-didocosyloxybenzyl alcohol)

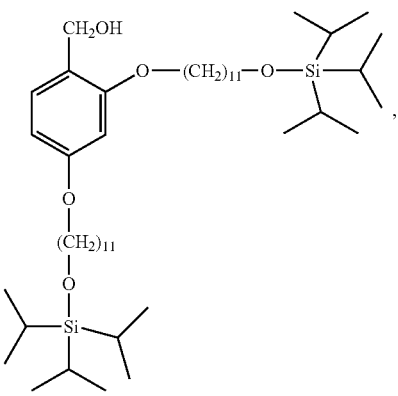
(2,4-di(11'-triisopropylsilyloxyundecyloxy)benzyl alcohol)

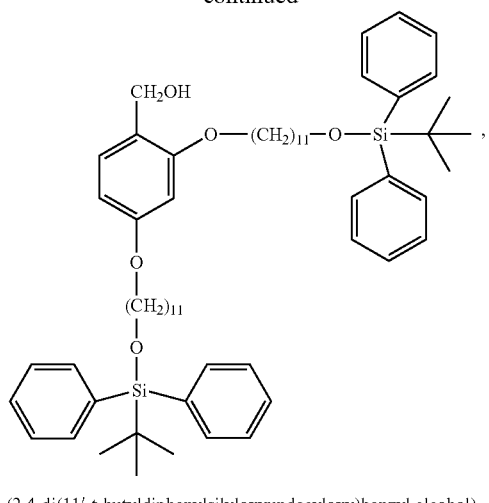

(2,4-di(11'-t-butyldiphenylsilyloxyundecyloxy)benzyl alcohol)

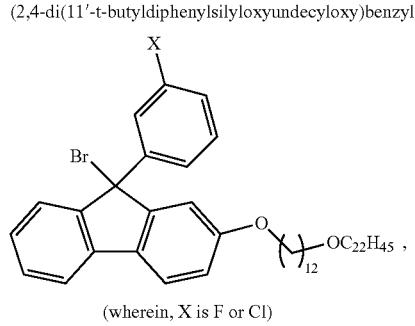

(wherein, X is F or Cl)

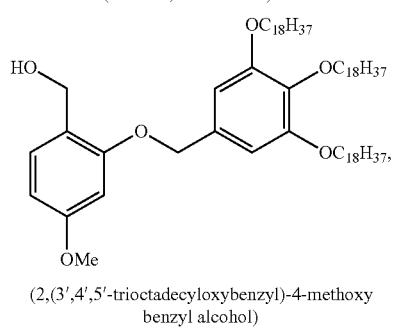

(2,(3',4',5'-trioctadecyloxybenzyl)-4-methoxy benzyl alcohol)

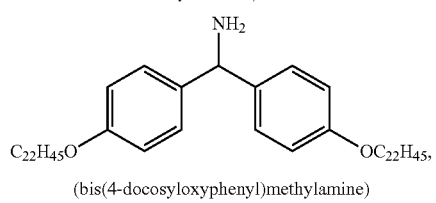

(bis(4-docosyloxyphenyl)methylamine)

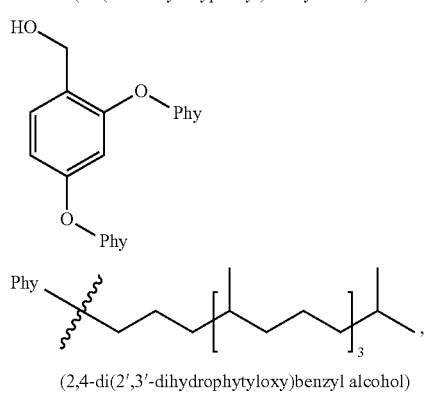

(2,4-di(2',3'-dihydrophytyloxy)benzyl alcohol)

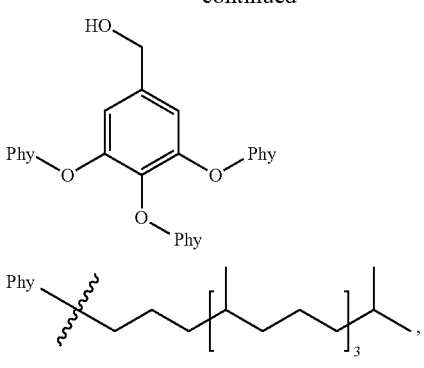

(3,4,5-tri(2',3'-dihydrophytyloxy)benzyl alcohol)

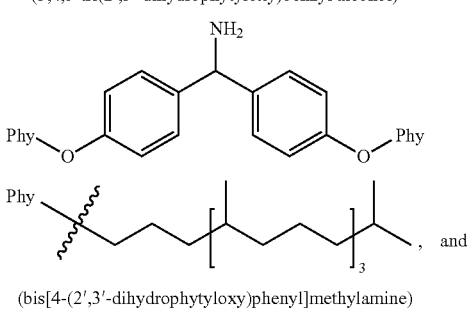

(bis[4-(2',3'-dihydrophytyloxy)phenyl]methylamine)

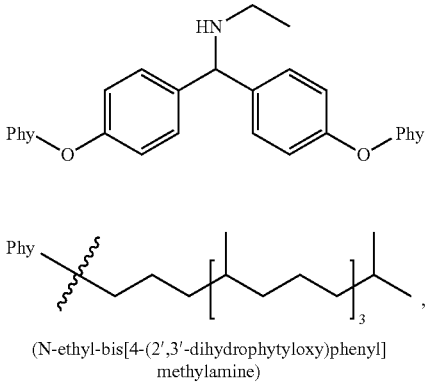

(N-ethyl-bis[4-(2',3'-dihydrophytyloxy)phenyl] methylamine)

wherein, each of the formula is shown in the condition before binding to a carboxyl group, an amino group, a thiol group or a hydroxyl group of an amino acid, a peptide or an amino acid amide or to a linker.

10. The peptide synthesis method according to claim 1, wherein the carrier for liquid phase peptide synthesis is a carrier derived from a compound selected from the group consisting of

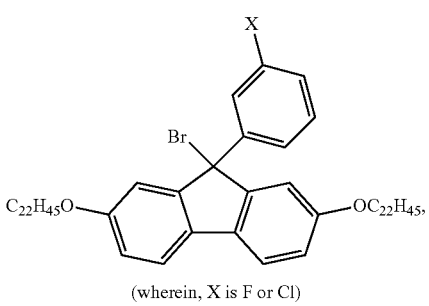

(wherein, X is F or Cl)

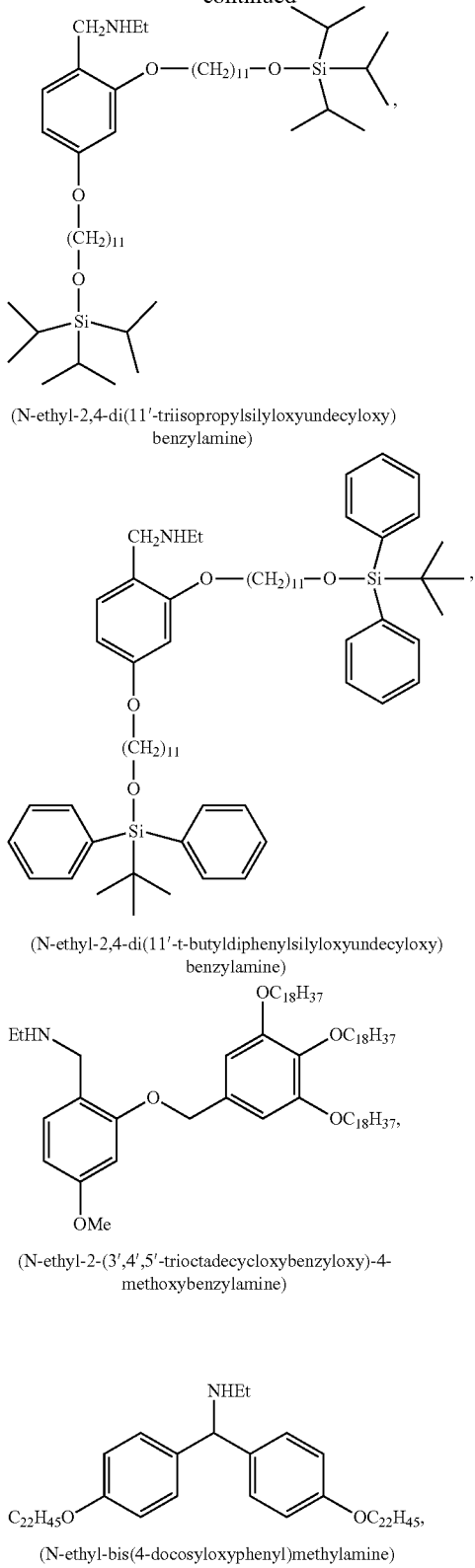

(N-ethyl-2,4-di(11'-triisopropylsilyloxyundecyloxy) benzylamine)

(N-ethyl-2,4-di(11'-t-butyldiphenylsilyloxyundecyloxy) benzylamine)

(N-ethyl-2-(3',4',5'-trioctadecycloxybenzyloxy)-4-methoxybenzylamine)

(N-ethyl-bis(4-docosyloxyphenyl)methylamine)

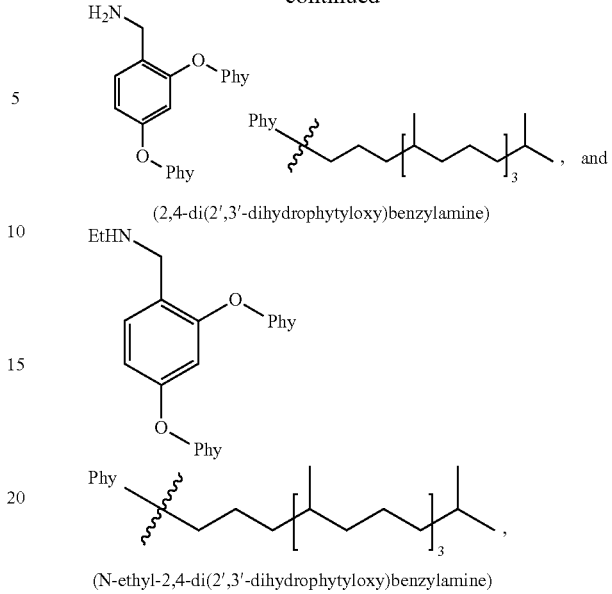

(2,4-di(2',3'-dihydrophytyloxy)benzylamine)

(N-ethyl-2,4-di(2',3'-dihydrophytyloxy)benzylamine)

wherein, each of the formula is shown in the condition before binding to a carboxyl group of an amino acid or a peptide).

11. The peptide synthesis method according to claim 1, wherein the organic solvent or mixed solution of organic solvents is at least one organic solvent selected from the group consisting of THF-DMF, cyclohexane, MTBE, 2-methylTHF, 4-methylTHP, isopropyl acetate, N-methylpyrrolidone and DCM, or a mixed solution composed of two or more of them.

12. The peptide synthesis method according to claim 1, wherein the water-soluble amine in step b is selected from the group consisting of 1-methylpiperazine, 4-aminopiperidine, diethylenetriamine, triaminoethylamine, 1-ethylpiperazine, N,N-dimethylethylenediamine, ethylenediamine and piperazine.

13. The peptide synthesis method according to claim 1, wherein an amine equivalent of the water-soluble amine in the step b is 1 to 10 equivalents with respect to the amino acid equivalent theoretically remaining after the condensation reaction in the step a.

14. The peptide synthesis method according to claim 1, wherein the water-soluble amine in the step c is present in an amount such that the water soluble amine has an amine equivalent of 5 to 30 equivalents with respect to the amount of the Fmoc group existing in the system.

15. The peptide synthesis method according to claim 1, wherein the pH of the acidic aqueous solution in the step d is 1 to 5.

16. The peptide synthesis method according to claim 1, comprising repeating step a through step d one or more times, using the carrier-protected peptide obtained by step d.

17. The peptide synthesis method according to claim 1, wherein the steps are conducted in one pot.

18. The peptide synthesis method according to claim 1, wherein a peptide having the following sequence is prepared: H-dArg-Arg-Pro-Hyp-Gly-Thi-Ser-dTic-Oic-Arg-OH.

* * * * *

UNITED STATES PATENT AND TRADEMARK OFFICE
CERTIFICATE OF CORRECTION

PATENT NO. : 11,420,997 B2
APPLICATION NO. : 17/046682
DATED : August 23, 2022
INVENTOR(S) : Hideaki Suzuki et al.

It is certified that error appears in the above-identified patent and that said Letters Patent is hereby corrected as shown below:

In the Claims

In Claim 3, Column 126, Line 56, delete "$R^6$" and insert -- $R^9$ --.

In Claim 4, Column 128, Line 39, delete "$X_2''$" and insert -- $X_2'''$ --.

In Claim 4, Column 128, Line 55, delete "no" and insert -- $n_6$ --.

In Claim 5, Column 130, Line 10, delete "155" and insert -- 15 --.

In Claim 5, Column 130, Line 29, delete "aryl ene" and insert -- arylene --.

In Claim 6, Column 131, Line 39, delete "5" and insert -- 15 --.

In Claim 7, Column 134, Line 1, delete "wherein, each" and insert -- wherein, Q each --.

In Claim 7, Column 134, Line 14, delete "no" and insert -- $n_0$ --.

In Claim 7, Column 134, Line 30, delete "formula" and insert -- formula (i) --.

In Claim 11, Column 140, Line 32, delete "THF-DMF" and insert -- THF, DMF --.

In Claim 11, Column 140, Line 32, delete "cyclohexane, MTBE" and insert -- cyclohexane, CPME, MTBE --.

Signed and Sealed this
Fifteenth Day of August, 2023

Katherine Kelly Vidal
*Director of the United States Patent and Trademark Office*

SEQUENCE LISTING

<160> NUMBER OF SEQ ID NOS: 32

<210> SEQ ID NO 1
<211> LENGTH: 10
<212> TYPE: PRT
<213> ORGANISM: Artificial Sequence
<220> FEATURE:
<223> OTHER INFORMATION: Icatibant obtained by present peptide synthesis
      method
<220> FEATURE:
<221> NAME/KEY: MISC_FEATURE
<222> LOCATION: (1)..(1)
<223> OTHER INFORMATION: X is D-Arg
<220> FEATURE:
<221> NAME/KEY: MISC_FEATURE
<222> LOCATION: (4)..(4)
<223> OTHER INFORMATION: X is Hyp
<220> FEATURE:
<221> NAME/KEY: MISC_FEATURE
<222> LOCATION: (6)..(6)
<223> OTHER INFORMATION: X is Thi
<220> FEATURE:
<221> NAME/KEY: MISC_FEATURE
<222> LOCATION: (8)..(8)
<223> OTHER INFORMATION: X is D-Tic
<220> FEATURE:
<221> NAME/KEY: MISC_FEATURE
<222> LOCATION: (9)..(9)
<223> OTHER INFORMATION: X is Oic

<400> SEQUENCE: 1

Arg Arg Pro Xaa Gly Xaa Ser Xaa Xaa Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: leuprorelin
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (10)..(10)
<223> OTHER INFORMATION: X is NHEt

<400> SEQUENCE: 2

Xaa His Trp Ser Tyr Leu Leu Arg Pro Xaa
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is His(Trt)
<220> FEATURE:
<221> NAME/KEY: MISC_FEATURE
<222> LOCATION: (2)..(2)
<223> OTHER INFORMATION: X is Trp(Boc)
<220> FEATURE:

```
<221> NAME/KEY: MISC_FEATURE
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
<223> OTHER INFORMATION: X is Tyr(tBu)
<220> FEATURE:
<221> NAME/KEY: MISC_FEATURE
<222> LOCATION: (5)..(5)
<223> OTHER INFORMATION: X is D-Leu
<220> FEATURE:
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (8)..(8)
<223> OTHER INFORMATION: X is OKb

<400> SEQUENCE: 3

His Trp Ser Tyr Leu Leu Arg Xaa
1               5

<210> SEQ ID NO 4
<211> LENGTH: 9
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is OKb

<400> SEQUENCE: 4

Xaa His Trp Ser Tyr Leu Leu Arg Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Peptide obtained by present peptide synthesis
```

```
        method, which is partial peptide of SEQ ID:2 having protective
        groups
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(2)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)

<400> SEQUENCE: 5

Xaa His Trp Ser Tyr Leu Leu Arg
1               5

<210> SEQ ID NO 6
<211> LENGTH: 10
<212> TYPE: PRT
<213> ORGANISM: Artificial Sequence
<220> FEATURE:
<223> OTHER INFORMATION: Peptide obtained by present peptide synthesis
      method, which is peptide of SEQ ID:2 having protective groups
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (10)..(10)
<223> OTHER INFORMATION: X is NHEt

<400> SEQUENCE: 6
```

```
Xaa His Trp Ser Tyr Leu Leu Arg Pro Xaa
1               5                   10
```

<210> SEQ ID NO 7
<211> LENGTH: 10
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:1 having protective
      groups
<220> FEATURE:
<221> NAME/KEY: MISC_FEATURE
<222> LOCATION: (1)..(1)
<223> OTHER INFORMATION: X is Arg(Pbf)
<220> FEATURE:
<221> NAME/KEY: MISC_FEATURE
<222> LOCATION: (3)..(3)
<223> OTHER INFORMATION: X is Hyp
<220> FEATURE:
<221> NAME/KEY: MISC_FEATURE
<222> LOCATION: (5)..(5)
<223> OTHER INFORMATION: X is Thi
<220> FEATURE:
<221> NAME/KEY: MISC_FEATURE
<222> LOCATION: (6)..(6)
<223> OTHER INFORMATION: X is Ser(tBu)
<220> FEATURE:
<221> NAME/KEY: MISC_FEATURE
<222> LOCATION: (7)..(7)
<223> OTHER INFORMATION: X is D-Tic
<220> FEATURE:
<221> NAME/KEY: MISC_FEATURE
<222> LOCATION: (8)..(8)
<223> OTHER INFORMATION: X is Oic
<220> FEATURE:
<221> NAME/KEY: MISC_FEATURE
<222> LOCATION: (9)..(9)
<223> OTHER INFORMATION: X is Arg(Pbf)
<220> FEATURE:
<221> NAME/KEY: MISC_FEATURE
<222> LOCATION: (10)..(10)
<223> OTHER INFORMATION: X is OKb

<400> SEQUENCE: 7

```
Arg Pro Xaa Gly Xaa Ser Xaa Xaa Arg Xaa
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Peptide obtained by present peptide synthesis
      method, which is peptide of SEQ ID:1 having protective groups
<220> FEATURE:
<221> NAME/KEY: MISC_FEATURE
<222> LOCATION: (1)..(1)
<223> OTHER INFORMATION: X is Boc
<220> FEATURE:
<221> NAME/KEY: MISC_FEATURE
<222> LOCATION: (2)..(2)
<223> OTHER INFORMATION: X is D-Arg(Pbf)
<220> FEATURE:
<221> NAME/KEY: MISC_FEATURE
<222> LOCATION: (3)..(3)
<223> OTHER INFORMATION: X is Arg(Pbf)
<220> FEATURE:
<221> NAME/KEY: MISC_FEATURE
<222> LOCATION: (5)..(5)
<223> OTHER INFORMATION: X is Hyp
<220> FEATURE:
<221> NAME/KEY: MISC_FEATURE
<222> LOCATION: (7)..(7)
<223> OTHER INFORMATION: X is Thi
<220> FEATURE:

```
<221> NAME/KEY: MISC_FEATURE
<222> LOCATION: (8)..(8)
<223> OTHER INFORMATION: X is Ser(tBu)
<220> FEATURE:
<221> NAME/KEY: MISC_FEATURE
<222> LOCATION: (9)..(9)
<223> OTHER INFORMATION: X is D-Tic
<220> FEATURE:
<221> NAME/KEY: MISC_FEATURE
<222> LOCATION: (10)..(10)
<223> OTHER INFORMATION: X is Oic
<220> FEATURE:
<221> NAME/KEY: MISC_FEATURE
<222> LOCATION: (11)..(11)
<223> OTHER INFORMATION: X is Arg(Pbf)
<220> FEATURE:
<221> NAME/KEY: MISC_FEATURE
<222> LOCATION: (12)..(12)
<223> OTHER INFORMATION: X is OKb

<400> SEQUENCE: 8

Xaa Arg Arg Pro Xaa Gly Xaa Ser Xaa Xaa Arg Xaa
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is His(Trt)
<220> FEATURE:
<221> NAME/KEY: MISC_FEATURE
<222> LOCATION: (2)..(2)
<223> OTHER INFORMATION: X is Trp(Boc)
<220> FEATURE:
<221> NAME/KEY: MISC_FEATURE
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
<223> OTHER INFORMATION: X is Tyr(tBu)
<220> FEATURE:
<221> NAME/KEY: MISC_FEATURE
<222> LOCATION: (5)..(5)
<223> OTHER INFORMATION: X is D-Leu
<220> FEATURE:
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is EtNKb

<400> SEQUENCE: 9

His Trp Ser Tyr Leu Leu Arg Pro Xaa
1               5

<210> SEQ ID NO 10
<211> LENGTH: 10
<212> TYPE: PRT
<213> ORGANISM: Artificial Sequence
<220> FEATURE:
<223> OTHER INFORMATION: Peptide obtained by present peptide synthesis
      method, which is peptide of SEQ ID:2 having protective groups
<220> FEATURE:
<221> NAME/KEY: MISC_FEATURE
<222> LOCATION: (1)..(1)
```

```
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (10)..(10)
<223> OTHER INFORMATION: X is EtNKb

<400> SEQUENCE: 10

Xaa His Trp Ser Tyr Leu Leu Arg Pro Xaa
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is D-Tic
<220> FEATURE:
<221> NAME/KEY: MISC_FEATURE
<222> LOCATION: (2)..(2)
<223> OTHER INFORMATION: X is Oic
<220> FEATURE:
<221> NAME/KEY: MISC_FEATURE
<222> LOCATION: (3)..(3)
<223> OTHER INFORMATION: X is Arg(Pbf)
<220> FEATURE:
<221> NAME/KEY: MISC_FEATURE
<222> LOCATION: (4)..(4)
<223> OTHER INFORMATION: X is OKa

<400> SEQUENCE: 11

Xaa Xaa Arg Xaa
1

<210> SEQ ID NO 12
<211> LENGTH: 5
<212> TYPE: PRT
<213> ORGANISM: Artificial Sequence
<220> FEATURE:
<223> OTHER INFORMATION: Peptide obtained by known peptide synthesis
      method, which is partial peptide of SEQ ID:1 having protective
      groups
<220> FEATURE:
<221> NAME/KEY: MISC_FEATURE
<222> LOCATION: (1)..(1)
<223> OTHER INFORMATION: X is Ser(tBu)
<220> FEATURE:
<221> NAME/KEY: MISC_FEATURE
```

```
<222> LOCATION: (2)..(2)
<223> OTHER INFORMATION: X is D-Tic
<220> FEATURE:
<221> NAME/KEY: MISC_FEATURE
<222> LOCATION: (3)..(3)
<223> OTHER INFORMATION: X is Oic
<220> FEATURE:
<221> NAME/KEY: MISC_FEATURE
<222> LOCATION: (4)..(4)
<223> OTHER INFORMATION: X is Arg(Pbf)
<220> FEATURE:
<221> NAME/KEY: MISC_FEATURE
<222> LOCATION: (5)..(5)
<223> OTHER INFORMATION: X is OKa

<400> SEQUENCE: 12

Ser Xaa Xaa Arg Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Peptide obtained by known peptide synthesis
      method, which is partial peptide of SEQ ID:1 having protective
      groups
<220> FEATURE:
<221> NAME/KEY: MISC_FEATURE
<222> LOCATION: (1)..(1)
<223> OTHER INFORMATION: X is Thi
<220> FEATURE:
<221> NAME/KEY: MISC_FEATURE
<222> LOCATION: (2)..(2)
<223> OTHER INFORMATION: X is Ser(tBu)
<220> FEATURE:
<221> NAME/KEY: MISC_FEATURE
<222> LOCATION: (3)..(3)
<223> OTHER INFORMATION: X is D-Tic
<220> FEATURE:
<221> NAME/KEY: MISC_FEATURE
<222> LOCATION: (4)..(4)
<223> OTHER INFORMATION: X is Oic
<220> FEATURE:
<221> NAME/KEY: MISC_FEATURE
<222> LOCATION: (5)..(5)
<223> OTHER INFORMATION: X is Arg(Pbf)
<220> FEATURE:
<221> NAME/KEY: MISC_FEATURE
<222> LOCATION: (6)..(6)
<223> OTHER INFORMATION: X is OKa

<400> SEQUENCE: 13

Xaa Ser Xaa Xaa Arg Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Peptide obtained by known peptide synthesis
      method, which is partial peptide of SEQ ID:1 having protective
      groups
<220> FEATURE:
<221> NAME/KEY: MISC_FEATURE
<222> LOCATION: (2)..(2)
<223> OTHER INFORMATION: X is Thi
<220> FEATURE:
<221> NAME/KEY: MISC_FEATURE
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
```

-continued

<223> OTHER INFORMATION: X is D-Tic
<220> FEATURE:
<221> NAME/KEY: MISC_FEATURE
<222> LOCATION: (5)..(5)
<223> OTHER INFORMATION: X is Oic
<220> FEATURE:
<221> NAME/KEY: MISC_FEATURE
<222> LOCATION: (6)..(6)
<223> OTHER INFORMATION: X is Arg(Pbf)
<220> FEATURE:
<221> NAME/KEY: MISC_FEATURE
<222> LOCATION: (7)..(7)
<223> OTHER INFORMATION: X is OKa

<400> SEQUENCE: 14

Gly Xaa Ser Xaa Xaa Arg Xaa
1               5

<210> SEQ ID NO 15
<211> LENGTH: 8
<212> TYPE: PRT
<213> ORGANISM: Artificial Sequence
<220> FEATURE:
<223> OTHER INFORMATION: Peptide obtained by known peptide synthesis
      method, which is partial peptide of SEQ ID:1 having protective
      groups
<220> FEATURE:
<221> NAME/KEY: MISC_FEATURE
<222> LOCATION: (1)..(1)
<223> OTHER INFORMATION: X is Hyp
<220> FEATURE:
<221> NAME/KEY: MISC_FEATURE
<222> LOCATION: (3)..(3)
<223> OTHER INFORMATION: X is Thi
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is D-Tic
<220> FEATURE:
<221> NAME/KEY: MISC_FEATURE
<222> LOCATION: (6)..(6)
<223> OTHER INFORMATION: X is Oic
<220> FEATURE:
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (8)..(8)
<223> OTHER INFORMATION: X is OKa

<400> SEQUENCE: 15

Xaa Gly Xaa Ser Xaa Xaa Arg Xaa
1               5

<210> SEQ ID NO 16
<211> LENGTH: 9
<212> TYPE: PRT
<213> ORGANISM: Artificial Sequence
<220> FEATURE:
<223> OTHER INFORMATION: Peptide obtained by known peptide synthesis
      method, which is partial peptide of SEQ ID:1 having protective
      groups
<220> FEATURE:
<221> NAME/KEY: MISC_FEATURE
<222> LOCATION: (2)..(2)
<223> OTHER INFORMATION: X is Hyp
<220> FEATURE:
<221> NAME/KEY: MISC_FEATURE
<222> LOCATION: (4)..(4)
<223> OTHER INFORMATION: X is Thi

```
<220> FEATURE:
<221> NAME/KEY: MISC_FEATURE
<222> LOCATION: (5)..(5)
<223> OTHER INFORMATION: X is Ser(tBu)
<220> FEATURE:
<221> NAME/KEY: MISC_FEATURE
<222> LOCATION: (6)..(6)
<223> OTHER INFORMATION: X is D-Tic
<220> FEATURE:
<221> NAME/KEY: MISC_FEATURE
<222> LOCATION: (7)..(7)
<223> OTHER INFORMATION: X is Oic
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is OKa

<400> SEQUENCE: 16

Pro Xaa Gly Xaa Ser Xaa Xaa Arg Xaa
1               5

<210> SEQ ID NO 17
<211> LENGTH: 10
<212> TYPE: PRT
<213> ORGANISM: Artificial Sequence
<220> FEATURE:
<223> OTHER INFORMATION: Peptide obtained by known peptide synthesis
      method, which is partial peptide of SEQ ID:1 having protective
      groups
<220> FEATURE:
<221> NAME/KEY: MISC_FEATURE
<222> LOCATION: (1)..(1)
<223> OTHER INFORMATION: X is Arg(Pbf)
<220> FEATURE:
<221> NAME/KEY: MISC_FEATURE
<222> LOCATION: (3)..(3)
<223> OTHER INFORMATION: X is Hyp
<220> FEATURE:
<221> NAME/KEY: MISC_FEATURE
<222> LOCATION: (5)..(5)
<223> OTHER INFORMATION: X is Thi
<220> FEATURE:
<221> NAME/KEY: MISC_FEATURE
<222> LOCATION: (6)..(6)
<223> OTHER INFORMATION: X is Ser(tBu)
<220> FEATURE:
<221> NAME/KEY: MISC_FEATURE
<222> LOCATION: (7)..(7)
<223> OTHER INFORMATION: X is D-Tic
<220> FEATURE:
<221> NAME/KEY: MISC_FEATURE
<222> LOCATION: (8)..(8)
<223> OTHER INFORMATION: X is Oic
<220> FEATURE:
<221> NAME/KEY: MISC_FEATURE
<222> LOCATION: (9)..(9)
<223> OTHER INFORMATION: X is Arg(Pbf)
<220> FEATURE:
<221> NAME/KEY: MISC_FEATURE
<222> LOCATION: (10)..(10)
<223> OTHER INFORMATION: X is OKa

<400> SEQUENCE: 17

Arg Pro Xaa Gly Xaa Ser Xaa Xaa Arg Xaa
1               5                   10

<210> SEQ ID NO 18
<211> LENGTH: 11
<212> TYPE: PRT
<213> ORGANISM: Artificial Sequence
<220> FEATURE:
```

```
<223> OTHER INFORMATION: Peptide obtained by known peptide synthesis
      method, which is peptide of SEQ ID:1 having protective groups
<220> FEATURE:
<221> NAME/KEY: MISC_FEATURE
<222> LOCATION: (1)..(1)
<223> OTHER INFORMATION: X is D-Arg(Pbf)
<220> FEATURE:
<221> NAME/KEY: MISC_FEATURE
<222> LOCATION: (2)..(2)
<223> OTHER INFORMATION: X is Arg(Pbf)
<220> FEATURE:
<221> NAME/KEY: MISC_FEATURE
<222> LOCATION: (4)..(4)
<223> OTHER INFORMATION: X is Hyp
<220> FEATURE:
<221> NAME/KEY: MISC_FEATURE
<222> LOCATION: (6)..(6)
<223> OTHER INFORMATION: X is Thi
<220> FEATURE:
<221> NAME/KEY: MISC_FEATURE
<222> LOCATION: (7)..(7)
<223> OTHER INFORMATION: X is Ser(tBu)
<220> FEATURE:
<221> NAME/KEY: MISC_FEATURE
<222> LOCATION: (8)..(8)
<223> OTHER INFORMATION: X is D-Tic
<220> FEATURE:
<221> NAME/KEY: MISC_FEATURE
<222> LOCATION: (9)..(9)
<223> OTHER INFORMATION: X is Oic
<220> FEATURE:
<221> NAME/KEY: MISC_FEATURE
<222> LOCATION: (10)..(10)
<223> OTHER INFORMATION: X is Arg(Pbf)
<220> FEATURE:
<221> NAME/KEY: MISC_FEATURE
<222> LOCATION: (11)..(11)
<223> OTHER INFORMATION: X is OKa

<400> SEQUENCE: 18

Arg Arg Pro Xaa Gly Xaa Ser Xaa Xaa Arg Xaa
1               5                   10

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide, which is partial peptide of
      SEQ ID:2
<220> FEATURE:
<221> NAME/KEY: MISC_FEATURE
<222> LOCATION: (4)..(4)
<223> OTHER INFORMATION: X is NHEt

<400> SEQUENCE: 19

Leu Arg Pro Xaa
1

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide, which is partial peptide of
      SEQ ID:2 having protective group
<220> FEATURE:
<221> NAME/KEY: MISC_FEATURE
<222> LOCATION: (2)..(2)
<223> OTHER INFORMATION: X is Arg(Pbf)
<220> FEATURE:
<221> NAME/KEY: MISC_FEATURE
<222> LOCATION: (4)..(4)
<223> OTHER INFORMATION: X is NHEt
```

```
<400> SEQUENCE: 20

Leu Arg Pro Xaa
1

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide, which is partial peptide of
      SEQ ID:2
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (6)..(6)
<223> OTHER INFORMATION: X is D-Leu

<400> SEQUENCE: 21

Xaa His Trp Ser Tyr Leu Leu Arg
1               5

<210> SEQ ID NO 22
<211> LENGTH: 8
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is His(Trt)
<220> FEATURE:
<221> NAME/KEY: MISC_FEATURE
<222> LOCATION: (2)..(2)
<223> OTHER INFORMATION: X is Trp(Boc)
<220> FEATURE:
<221> NAME/KEY: MISC_FEATURE
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
<223> OTHER INFORMATION: X is Tyr(tBu)
<220> FEATURE:
<221> NAME/KEY: MISC_FEATURE
<222> LOCATION: (5)..(5)
<223> OTHER INFORMATION: X is D-Leu
<220> FEATURE:
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (8)..(8)
<223> OTHER INFORMATION: X is O-KS1

<400> SEQUENCE: 22

His Trp Ser Tyr Leu Leu Arg Xaa
1               5

<210> SEQ ID NO 23
<211> LENGTH: 9
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
```

```
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is O-KS1

<400> SEQUENCE: 23

Xaa His Trp Ser Tyr Leu Leu Arg Xaa
1               5

<210> SEQ ID NO 24
<211> LENGTH: 8
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is His(Trt)
<220> FEATURE:
<221> NAME/KEY: MISC_FEATURE
<222> LOCATION: (2)..(2)
<223> OTHER INFORMATION: X is Trp(Boc)
<220> FEATURE:
<221> NAME/KEY: MISC_FEATURE
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
<223> OTHER INFORMATION: X is Tyr(tBu)
<220> FEATURE:
<221> NAME/KEY: MISC_FEATURE
<222> LOCATION: (5)..(5)
<223> OTHER INFORMATION: X is D-Leu
<220> FEATURE:
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (8)..(8)
<223> OTHER INFORMATION: X is O-Fl

<400> SEQUENCE: 24

His Trp Ser Tyr Leu Leu Arg Xaa
```

<210> SEQ ID NO 25
<211> LENGTH: 9
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is O-Fl

<400> SEQUENCE: 25

Xaa His Trp Ser Tyr Leu Leu Arg Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is His(Trt)
<220> FEATURE:
<221> NAME/KEY: MISC_FEATURE
<222> LOCATION: (2)..(2)
<223> OTHER INFORMATION: X is Trp(Boc)
<220> FEATURE:
<221> NAME/KEY: MISC_FEATURE
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
<223> OTHER INFORMATION: X is Tyr(tBu)
<220> FEATURE:
<221> NAME/KEY: MISC_FEATURE
<222> LOCATION: (5)..(5)
<223> OTHER INFORMATION: X is D-Leu
<220> FEATURE:

```
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (8)..(8)
<223> OTHER INFORMATION: X is O-KJ1

<400> SEQUENCE: 26

His Trp Ser Tyr Leu Leu Arg Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is O-KJ1

<400> SEQUENCE: 27

Xaa His Trp Ser Tyr Leu Leu Arg Xaa
1               5

<210> SEQ ID NO 28
<211> LENGTH: 9
<212> TYPE: PRT
<213> ORGANISM: Artificial Sequence
<220> FEATURE:
<223> OTHER INFORMATION: Peptide obtained by present peptide synthesis
      method, which is partial peptide of SEQ ID:2 having protective
      groups
<220> FEATURE:
<221> NAME/KEY: MISC_FEATURE
<222> LOCATION: (1)..(1)
<223> OTHER INFORMATION: X is His(Trt)
<220> FEATURE:
<221> NAME/KEY: MISC_FEATURE
<222> LOCATION: (2)..(2)
<223> OTHER INFORMATION: X is Trp(Boc)
<220> FEATURE:
<221> NAME/KEY: MISC_FEATURE
```

```
<222> LOCATION: (3)..(3)
<223> OTHER INFORMATION: X is Ser(tBu)
<220> FEATURE:
<221> NAME/KEY: MISC_FEATURE
<222> LOCATION: (4)..(4)
<223> OTHER INFORMATION: X is Tyr(tBu)
<220> FEATURE:
<221> NAME/KEY: MISC_FEATURE
<222> LOCATION: (5)..(5)
<223> OTHER INFORMATION: X is D-Leu
<220> FEATURE:
<221> NAME/KEY: MISC_FEATURE
<222> LOCATION: (7)..(7)
<223> OTHER INFORMATION: X is Arg(Pbf)
<220> FEATURE:
<221> NAME/KEY: MISC_FEATURE
<222> LOCATION: (9)..(9)
<223> OTHER INFORMATION: X is NEt-KJ3

<400> SEQUENCE: 28

His Trp Ser Tyr Leu Leu Arg Pro Xaa
1               5

<210> SEQ ID NO 29
<211> LENGTH: 10
<212> TYPE: PRT
<213> ORGANISM: Artificial Sequence
<220> FEATURE:
<223> OTHER INFORMATION: Peptide obtained by present peptide synthesis
      method, which is peptide of SEQ ID:2 having protective groups
<220> FEATURE:
<221> NAME/KEY: MISC_FEATURE
<222> LOCATION: (1)..(1)
<223> OTHER INFORMATION: X is Pyr
<220> FEATURE:
<221> NAME/KEY: MISC_FEATURE
<222> LOCATION: (2)..(2)
<223> OTHER INFORMATION: X is His(Trt)
<220> FEATURE:
<221> NAME/KEY: MISC_FEATURE
<222> LOCATION: (3)..(3)
<223> OTHER INFORMATION: X is Trp(Boc)
<220> FEATURE:
<221> NAME/KEY: MISC_FEATURE
<222> LOCATION: (4)..(4)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Tyr(tBu)
<220> FEATURE:
<221> NAME/KEY: MISC_FEATURE
<222> LOCATION: (6)..(6)
<223> OTHER INFORMATION: X is D-Leu
<220> FEATURE:
<221> NAME/KEY: MISC_FEATURE
<222> LOCATION: (8)..(8)
<223> OTHER INFORMATION: X is Arg(Pbf)
<220> FEATURE:
<221> NAME/KEY: MISC_FEATURE
<222> LOCATION: (10)..(10)
<223> OTHER INFORMATION: X is NEt-KJ3

<400> SEQUENCE: 29

Xaa His Trp Ser Tyr Leu Leu Arg Pro Xaa
1               5                   10

<210> SEQ ID NO 30
<211> LENGTH: 4
<212> TYPE: PRT
<213> ORGANISM: Artificial Sequence
<220> FEATURE:
<223> OTHER INFORMATION: Peptide obtained by present pepetide synthesis
      method, which is can be used in various fields
```

```
<400> SEQUENCE: 30

Ser Pro Leu Gln
1

<210> SEQ ID NO 31
<211> LENGTH: 4
<212> TYPE: PRT
<213> ORGANISM: Artificial Sequence
<220> FEATURE:
<223> OTHER INFORMATION: Peptide obtained by present peptide synthesis
      method, which is can be used in various fields
<220> FEATURE:
<221> NAME/KEY: MISC_FEATURE
<222> LOCATION: (3)..(3)
<223> OTHER INFORMATION: X is Gln(Trt)
<220> FEATURE:
<221> NAME/KEY: MISC_FEATURE
<222> LOCATION: (4)..(4)
<223> OTHER INFORMATION: X is OKb

<400> SEQUENCE: 31

Pro Leu Gln Xaa
1

<210> SEQ ID NO 32
<211> LENGTH: 6
<212> TYPE: PRT
<213> ORGANISM: Artificial Sequence
<220> FEATURE:
<223> OTHER INFORMATION: Peptide obtained by present peptide synthesis
      method, which is can be used in various fields
<220> FEATURE:
<221> NAME/KEY: MISC_FEATURE
<222> LOCATION: (1)..(1)
<223> OTHER INFORMATION: X is Boc
<220> FEATURE:
<221> NAME/KEY: MISC_FEATURE
<222> LOCATION: (2)..(2)
<223> OTHER INFORMATION: X is Ser(tBu)
<220> FEATURE:
<221> NAME/KEY: MISC_FEATURE
<222> LOCATION: (5)..(5)
<223> OTHER INFORMATION: X is Gln(Trt)
<220> FEATURE:
<221> NAME/KEY: MISC_FEATURE
<222> LOCATION: (6)..(6)
<223> OTHER INFORMATION: X is OKb

<400> SEQUENCE: 32

Xaa Ser Pro Leu Gln Xaa
1               5
```